(12) United States Patent
Srivastava et al.

(10) Patent No.: US 12,311,017 B2
(45) Date of Patent: *May 27, 2025

(54) IDENTIFICATION OF IMMUNOLOGICALLY PROTECTIVE NEO-EPITOPES FOR THE TREATMENT OF CANCERS

(71) Applicants: University of Connecticut, Farmington, CT (US); University of Notre Dame du Lac, Notre Dame, IN (US)

(72) Inventors: Pramod K. Srivastava, Avon, CT (US); Brian M. Baker, Granger, IN (US)

(73) Assignees: UNIVERSITY OF CONNECTICUT, Farmington, CT (US); UNIVERSITY OF NOTRE DAME DU LAC, Notre Dame, IN (US)

( * ) Notice: Subject to any disclaimer, the term of this patent is extended or adjusted under 35 U.S.C. 154(b) by 511 days.

This patent is subject to a terminal disclaimer.

(21) Appl. No.: 17/725,932

(22) Filed: Apr. 21, 2022

(65) Prior Publication Data

US 2022/0249634 A1 Aug. 11, 2022

Related U.S. Application Data

(60) Division of application No. 16/560,336, filed on Sep. 4, 2019, now Pat. No. 11,338,026, which is a continuation of application No. 15/501,919, filed as application No. PCT/US2015/048345 on Sep. 3, 2015, now abandoned.

(60) Provisional application No. 62/048,561, filed on Sep. 10, 2014.

(51) Int. Cl.
  *A61K 39/395* (2006.01)
  *A61K 39/00* (2006.01)
  *C12Q 1/6869* (2018.01)

(52) U.S. Cl.
  CPC ........ *A61K 39/0011* (2013.01); *A61K 39/395* (2013.01); *C12Q 1/6869* (2013.01); *C07K 2317/92* (2013.01)

(58) Field of Classification Search
  CPC .............. A61K 39/0011; A61K 39/395; C12Q 1/6869; C07K 2317/92; A61P 35/00
  USPC ...................................................... 435/7.23
  See application file for complete search history.

(56) References Cited

U.S. PATENT DOCUMENTS

| | | | |
|---|---|---|---|
| 8,140,270 B2 | 3/2012 | Kingsmore et al. | |
| 10,055,540 B2 | 8/2018 | Yelensky et al. | |
| 10,155,031 B2 | 12/2018 | Sahin et al. | |
| 10,426,824 B1 | 10/2019 | Hacohen et al. | |
| 10,501,801 B2 | 12/2019 | Srivastava et al. | |
| 11,920,202 B2 * | 3/2024 | Srivastava | G16B 45/00 |
| 2009/0098533 A1 | 4/2009 | Munnes et al. | |
| 2011/0257890 A1 | 10/2011 | Weinschenk et al. | |
| 2011/0293637 A1 | 12/2011 | Hacohen et al. | |
| 2012/0093845 A1 | 4/2012 | Tsunoda et al. | |
| 2015/0252427 A1 | 9/2015 | Srivastava et al. | |
| 2015/0297695 A1 | 10/2015 | Bae et al. | |
| 2017/0224799 A1 | 8/2017 | Srivastava et al. | |
| 2020/0017922 A1 | 1/2020 | Srivastava et al. | |
| 2020/0061168 A1 | 2/2020 | Srivastava et al. | |
| 2021/0317533 A1 | 10/2021 | Srivastava et al. | |

FOREIGN PATENT DOCUMENTS

| | | |
|---|---|---|
| AU | 2017268822 B2 | 3/2020 |
| WO | 2011143656 A2 | 11/2011 |
| WO | 2014052707 A2 | 4/2014 |
| WO | 2014523406 | 9/2014 |
| WO | 2012159754 A2 | 11/2016 |

OTHER PUBLICATIONS

Assarsson et al.; "A Quantitative Analysis of the Variables Affecting the Repertoire of T Cell Specificities Recognized after Vaccinia Virus Infection"; J Immunol/ 178; pp. 7890-7901; (2007).

Borbulevych, Oleg Y., et al., "Structures of MART-1 26/27~35 Peptide/HLA-A2 Complexes Reveal a Remarkable Disconnect between Antigen Structural Homology and T Cell Recognition", J. Mol. Biol., 2007, and vol. 372, No. 5 and pp. 1123-1136.

Brennick, C. et al.; "An unbiased approach to defining bona fide cancer neoepitopes that elicit immune-mediated cancer rejection"; The Journal of Clinical Investigation, vol. 131, Issue No. 3; 2021; 16 pages; doi: 10.1172/JCI142823.

Castle et al.; "Exploiting the Mutanome for Tumor Vaccination"; Cancer Research; 72(5); pp. 1081-1091; (2012).

Duan et al.; "A mutation in Transportin3 (Tnpo3) leads to generation of an individually distinct tumor-specific Kd-restricted epitope in the Meth A fibrosarcoma (TUM2P.899)"; The Journal of Immunology, vol. 192, Supplement 1, 71.32; 2014; 1 page.

(Continued)

*Primary Examiner* — Yan Xiao
(74) *Attorney, Agent, or Firm* — CANTOR COLBURN LLP

(57) ABSTRACT

Described herein are methods of identifying immunologically protective neo-epitopes from the cancer tissue DNA of cancer patients using biophysical principles as well as bioinformatics techniques. The identification of immunologically protective neo-epitopes provides pharmaceutical compositions with a limited number of tumor-specific peptides suitable for personalized genomics-driven immunotherapy of human cancer. Specifically disclosed herein is a method of using the conformational stability of an epitope in an MHC protein-binding groove to predict immunogenicity of peptides in a putative neo-peptide set from a tumor from a cancer patient. Pharmaceutical compositions and methods of administration are also included.

18 Claims, 16 Drawing Sheets

Specification includes a Sequence Listing.

(56) References Cited

OTHER PUBLICATIONS

Duan et al.; "Genomic and Bioinformatic Profiling of Mutational Neoepitopes Reveals New Rules to Predict Anticancer Immunogenicity"; J. Exp Med; 211; pp. 2231-2248; (2014).

Ebrahimi-Nik, H. et al.; "CD11c+ MHCIIlo GM-CSF-bone marrow-derived dendritic cells act as antigen donor cells and as antigen presenting cells in neoepitope-elicited tumor immunity against a mouse fibrosarcoma"; Cancer Immunology, Immunotherapy, vol. 67; 2018; pp. 1449-1459.

EP Application 13840946.1 Extended Search Report Issued on Sep. 2, 2016; 11 pages.

Fortier et al.; "The MHC Class I Peptide Repertoire is Molded by the Transcriptome"; The Journal of Experimental Medicine; 205(3); pp. 595-610; (2008).

Fritsch et al; "HLA-Binding Properties of Tumor Neoepitopes in Humans"; Cancer Immunology Res.; 2(6); pp. 522-529; (2014).

Ghorani et al.; "Differential Binding Affinity of Mutated Peptides for MHC Class I is a Predictor of Survival in Advanced Lung Cancer and Melanoma"; Annals of Oncology, vol. 29: pp. 271-279; (2017).

Hos, B. et al.; "Identification of a neo-epitope dominating endogenous CD8 T cell responses to MC-38 colorectal cancer"; Oncoimmunology, vol. 9, Issue No. 1; 2020; https://doi.org/10.1080/2162402X.2019.1673125; 11 pages.

International Search Report and Written Opinion; International Application No. PCT/US13/62100; International Filing Date Sep. 27, 2013; Date of Mailing Jan. 8, 2014; 18 pages.

Intrnational Search Report and Written Opinion; International Application No. PCT/US2015/048345; International Filing Date Sep. 3, 2015; Date of Mailing Dec. 15, 2015; 13 pages.

Jorgensen et al.; "NetMHCstab [ Predicting Stability of Peptide-MHC-1 Complexes; Impacts for Cytotoxic T Lymphocyte Epitope Discovery"; Immunology; 141; pp. 18-26 (2013).

Keskin, et al.; "Neoantigen vaccine generates intratumoral T cell responses in phase Ib glioblastoma trial"; Nature, vol. 565, Issue No. 7738; 2019; pp. 234-239.

Knapp, Bernhard, "3-Layer-based analysis of peptide-MHC interaction: In silico prediction, peptide binding affinity and T cell activation in a relevant allergen-specific model", Molecular Immunology, 2009, and vol. 46 and pp. 1839-1844.

Kreiter et al.; "Targeting the Tumor Mutanome for Personalized Vaccinatio Therapy"; OncoImmunology; 1:5; pp. 768-769; (2012).

Martin, S. et al.; "Low Mutation Burden in Ovarian Cancer May Limit the Utility of Neoantigen-Targeted Vaccines"; PLOS One, vol. 11, Issue No. 5; 2016; doi:10.1371/journal.pone.0155189; 22 pages.

Massive Parallel Sequencing from Wikipedia; available under the Creative Commons Attribution_ShareAlike License; 7 pages; https://en.wikipedia.org/w/index.php?title=Massive_parallel_sequencing&oldid=853277093; printed Sep. 2018.

Philip, M. et al.; "Chromatin states define tumor-specific T cell dysfunction and reprogramming"; Nature, vol. 545, Issue 7655; 2017; pp. 452-456.

Priyadarshini, Vani et al., "Genome-based approaches to develop epitope-driven subunit vaccines against pathogens of infective endocarditis", Journal of BiomolecularStructure and Dynamics, Apr. 2014, vol. 32, No. 6, pp. 876-889.

Rech et al.; "Tumor Immunity and Survival as a Function of Alternative Neopeptides in Human Cancer"; Cancer Immunology Research, vol. 6, Issue No. 3; pp. 1-12 (2018); Published OnlineFirst Jan. 16, 2018.

Search Report for EP Application 15839204.3; Extended Search Report Issued on Mar. 27, 2018; 9 pages.

Segal et al.; "Epitope Landscape in Breast and Colorectal Cancer"; Cancer Res; 68(3); pp. 889-892; (2008).

Srivastava et al.; "Modeling the Repertoire of True Tumor-Specific MHC 1 Epitopes in a Human Tumor"; PLoS One; 4; e6094; pp. 1-7 (2009).

Stephens et al.; "The Landscape of Cancer Genes and Mutational Processes in Breast Cancer"; Nature; 486; pp. 400-404; (2012).

Li, L. et al.; "Preclinical and clinical development of neoantigen vaccines"; Annals of Oncology, vol. 28, Supplement 12; 2017; pp. xii11-xii17; DOI: 10.1093/annonc/mdx681.

* cited by examiner

SEQUENCE LISTING

```
<160> NUMBER OF SEQ ID NOS: 138

<210> SEQ ID NO 1
<211> LENGTH: 8
<212> TYPE: PRT
<213> ORGANISM: Gallus gallus

<400> SEQUENCE: 1

Ser Ile Ile Asn Phe Glu Lys Leu
1               5

<210> SEQ ID NO 2
<211> LENGTH: 9
<212> TYPE: PRT
<213> ORGANISM: Mus musculus

<400> SEQUENCE: 2

Ser Tyr Met Leu Gln Ala Leu Cys Ile
1               5

<210> SEQ ID NO 3
<211> LENGTH: 9
<212> TYPE: PRT
<213> ORGANISM: Mus musculus

<400> SEQUENCE: 3

Gly Tyr Ser Val Leu His Leu Ala Ile
1               5

<210> SEQ ID NO 4
<211> LENGTH: 10
<212> TYPE: PRT
<213> ORGANISM: Mus musculus

<400> SEQUENCE: 4

Gly Tyr Ser Val Leu His Leu Ala Ile Ile
1               5                   10
```

```
<210> SEQ ID NO 5
<211> LENGTH: 10
<212> TYPE: PRT
<213> ORGANISM: Mus musculus

<400> SEQUENCE: 5

Gly Asp Ser Val Leu His Leu Ala Ile Ile
1               5                   10

<210> SEQ ID NO 6
<211> LENGTH: 9
<212> TYPE: PRT
<213> ORGANISM: Mus musculus

<400> SEQUENCE: 6

Cys Tyr Ala Lys Val Lys Glu Gln Leu
1               5

<210> SEQ ID NO 7
<211> LENGTH: 9
<212> TYPE: PRT
<213> ORGANISM: Mus musculus

<400> SEQUENCE: 7

Cys Tyr Ala Lys Leu Lys Glu Gln Leu
1               5

<210> SEQ ID NO 8
<211> LENGTH: 9
<212> TYPE: PRT
<213> ORGANISM: Mus musculus

<400> SEQUENCE: 8

Gln Tyr Ile His Ser Ala Asn Val Leu
1               5

<210> SEQ ID NO 9
<211> LENGTH: 9
<212> TYPE: PRT
<213> ORGANISM: Mus musculus

<400> SEQUENCE: 9

Lys Tyr Ile His Ser Ala Asn Val Leu
1               5

<210> SEQ ID NO 10
<211> LENGTH: 11
<212> TYPE: PRT
<213> ORGANISM: Mus musculus

<400> SEQUENCE: 10

His Tyr Val His Ile Ile Glu Ser Lys Pro Leu
1               5                   10

<210> SEQ ID NO 11
<211> LENGTH: 11
<212> TYPE: PRT
<213> ORGANISM: Mus musculus

<400> SEQUENCE: 11

His Tyr Leu His Ile Ile Glu Ser Lys Pro Leu
1               5                   10

<210> SEQ ID NO 12
<211> LENGTH: 10
```

```
<212> TYPE: PRT
<213> ORGANISM: Mus musculus

<400> SEQUENCE: 12

His Tyr Leu Gln Tyr Lys Gln Glu Asp Leu
1               5                   10

<210> SEQ ID NO 13
<211> LENGTH: 10
<212> TYPE: PRT
<213> ORGANISM: Mus musculus

<400> SEQUENCE: 13

Gln Tyr Leu Gln Tyr Lys Gln Glu Asp Leu
1               5                   10

<210> SEQ ID NO 14
<211> LENGTH: 8
<212> TYPE: PRT
<213> ORGANISM: Mus musculus

<400> SEQUENCE: 14

Gln Tyr Ile His Ser Ala Asn Val
1               5

<210> SEQ ID NO 15
<211> LENGTH: 8
<212> TYPE: PRT
<213> ORGANISM: Mus musculus

<400> SEQUENCE: 15

Lys Tyr Ile His Ser Ala Asn Val
1               5

<210> SEQ ID NO 16
<211> LENGTH: 11
<212> TYPE: PRT
<213> ORGANISM: Mus musculus

<400> SEQUENCE: 16

Leu Tyr Gln Ile Leu Arg Gly Leu Gln Tyr Ile
1               5                   10

<210> SEQ ID NO 17
<211> LENGTH: 11
<212> TYPE: PRT
<213> ORGANISM: Mus musculus

<400> SEQUENCE: 17

Leu Tyr Gln Ile Leu Arg Gly Leu Lys Tyr Ile
1               5                   10

<210> SEQ ID NO 18
<211> LENGTH: 11
<212> TYPE: PRT
<213> ORGANISM: Mus musculus

<400> SEQUENCE: 18

Asn Tyr Leu Leu Ser Leu Val Ala Val Met Leu
1               5                   10

<210> SEQ ID NO 19
<211> LENGTH: 11
<212> TYPE: PRT
<213> ORGANISM: Mus musculus
```

<400> SEQUENCE: 19

Asn Tyr Leu Leu Ser Leu Val Ala Val Val Leu
1               5                   10

<210> SEQ ID NO 20
<211> LENGTH: 8
<212> TYPE: PRT
<213> ORGANISM: Mus musculus

<400> SEQUENCE: 20

Ser Tyr Leu Val Val Phe Pro Leu
1               5

<210> SEQ ID NO 21
<211> LENGTH: 8
<212> TYPE: PRT
<213> ORGANISM: Mus musculus

<400> SEQUENCE: 21

Ser Tyr Arg Val Val Phe Pro Leu
1               5

<210> SEQ ID NO 22
<211> LENGTH: 11
<212> TYPE: PRT
<213> ORGANISM: Mus musculus

<400> SEQUENCE: 22

Gln Tyr Ser Gly Ser Trp Val Glu Thr Pro Val
1               5                   10

<210> SEQ ID NO 23
<211> LENGTH: 11
<212> TYPE: PRT
<213> ORGANISM: Mus musculus

<400> SEQUENCE: 23

Gln Tyr Ser Gly Ser Arg Val Glu Thr Pro Val
1               5                   10

<210> SEQ ID NO 24
<211> LENGTH: 9
<212> TYPE: PRT
<213> ORGANISM: Mus musculus

<400> SEQUENCE: 24

His Tyr Ile Asn Met Ile Leu Pro Ile
1               5

<210> SEQ ID NO 25
<211> LENGTH: 9
<212> TYPE: PRT
<213> ORGANISM: Mus musculus

<400> SEQUENCE: 25

His Tyr Ile Asn Met Ser Leu Pro Ile
1               5

<210> SEQ ID NO 26
<211> LENGTH: 9
<212> TYPE: PRT
<213> ORGANISM: Mus musculus

<400> SEQUENCE: 26

Ala Tyr Cys Glu Thr Cys Trp Glu Leu
1               5

<210> SEQ ID NO 27
<211> LENGTH: 9
<212> TYPE: PRT
<213> ORGANISM: Mus musculus

<400> SEQUENCE: 27

Ala Tyr Cys Glu Thr Cys Trp Glu Trp
1               5

<210> SEQ ID NO 28
<211> LENGTH: 11
<212> TYPE: PRT
<213> ORGANISM: Mus musculus

<400> SEQUENCE: 28

Ser Tyr Leu Leu Gly Ser Gly Glu Ala Arg Leu
1               5                   10

<210> SEQ ID NO 29
<211> LENGTH: 11
<212> TYPE: PRT
<213> ORGANISM: Mus musculus

<400> SEQUENCE: 29

Ser Tyr Gln Leu Gly Ser Gly Glu Ala Arg Leu
1               5                   10

<210> SEQ ID NO 30
<211> LENGTH: 10
<212> TYPE: PRT
<213> ORGANISM: Mus musculus

<400> SEQUENCE: 30

Thr Tyr Ile Arg Pro Phe Glu Thr Lys Val
1               5                   10

<210> SEQ ID NO 31
<211> LENGTH: 10
<212> TYPE: PRT
<213> ORGANISM: Mus musculus

<400> SEQUENCE: 31

Thr Tyr Ile Arg Pro Leu Glu Thr Lys Val
1               5                   10

<210> SEQ ID NO 32
<211> LENGTH: 9
<212> TYPE: PRT
<213> ORGANISM: Mus musculus

<400> SEQUENCE: 32

His Tyr Leu Ser Ser Ile Leu Arg Leu
1               5

<210> SEQ ID NO 33
<211> LENGTH: 9
<212> TYPE: PRT
<213> ORGANISM: Mus musculus

<400> SEQUENCE: 33

His Tyr Leu Ser Ala Ile Leu Arg Leu

-continued

```
<210> SEQ ID NO 34
<211> LENGTH: 11
<212> TYPE: PRT
<213> ORGANISM: Mus musculus

<400> SEQUENCE: 34

Leu Tyr Leu Asp Ser Lys Ser Asp Thr Thr Val
1               5                   10

<210> SEQ ID NO 35
<211> LENGTH: 11
<212> TYPE: PRT
<213> ORGANISM: Mus musculus

<400> SEQUENCE: 35

Ser Tyr Leu Asp Ser Lys Ser Asp Thr Thr Val
1               5                   10

<210> SEQ ID NO 36
<211> LENGTH: 11
<212> TYPE: PRT
<213> ORGANISM: Mus musculus

<400> SEQUENCE: 36

Tyr Tyr Val Pro Leu Leu Lys Arg Val Pro Leu
1               5                   10

<210> SEQ ID NO 37
<211> LENGTH: 11
<212> TYPE: PRT
<213> ORGANISM: Mus musculus

<400> SEQUENCE: 37

Tyr Tyr Val Pro Leu Leu Lys Arg Val Pro Ser
1               5                   10

<210> SEQ ID NO 38
<211> LENGTH: 10
<212> TYPE: PRT
<213> ORGANISM: Mus musculus

<400> SEQUENCE: 38

Lys Tyr Met Ser Met Leu Glu Glu Arg Ile
1               5                   10

<210> SEQ ID NO 39
<211> LENGTH: 10
<212> TYPE: PRT
<213> ORGANISM: Mus musculus

<400> SEQUENCE: 39

Lys Asp Met Ser Met Leu Glu Glu Arg Ile
1               5                   10

<210> SEQ ID NO 40
<211> LENGTH: 11
<212> TYPE: PRT
<213> ORGANISM: Mus musculus

<400> SEQUENCE: 40

Gly Tyr Phe Val Ser Lys Ala Lys Thr Ser Val
1               5                   10
```

<210> SEQ ID NO 41
<211> LENGTH: 11
<212> TYPE: PRT
<213> ORGANISM: Mus musculus

<400> SEQUENCE: 41

Gly Tyr Phe Val Ser Lys Ala Lys Thr Arg Val
1               5                   10

<210> SEQ ID NO 42
<211> LENGTH: 11
<212> TYPE: PRT
<213> ORGANISM: Mus musculus

<400> SEQUENCE: 42

Pro Tyr Leu Thr Gln Tyr Ala Ile Ile Met Leu
1               5                   10

<210> SEQ ID NO 43
<211> LENGTH: 11
<212> TYPE: PRT
<213> ORGANISM: Mus musculus

<400> SEQUENCE: 43

Pro Asp Leu Thr Gln Tyr Ala Ile Ile Met Leu
1               5                   10

<210> SEQ ID NO 44
<211> LENGTH: 8
<212> TYPE: PRT
<213> ORGANISM: Mus musculus

<400> SEQUENCE: 44

Asp Tyr Val Pro Met Glu Gln Pro
1               5

<210> SEQ ID NO 45
<211> LENGTH: 8
<212> TYPE: PRT
<213> ORGANISM: Mus musculus

<400> SEQUENCE: 45

Asp Asp Val Pro Met Glu Gln Pro
1               5

<210> SEQ ID NO 46
<211> LENGTH: 8
<212> TYPE: PRT
<213> ORGANISM: Mus musculus

<400> SEQUENCE: 46

Pro Tyr Leu Thr Gln Tyr Ala Ile
1               5

<210> SEQ ID NO 47
<211> LENGTH: 8
<212> TYPE: PRT
<213> ORGANISM: Mus musculus

<400> SEQUENCE: 47

Pro Asp Leu Thr Gln Tyr Ala Ile
1               5

<210> SEQ ID NO 48

```
<211> LENGTH: 9
<212> TYPE: PRT
<213> ORGANISM: Mus musculus

<400> SEQUENCE: 48

Pro Tyr Leu Thr Gln Tyr Ala Ile Ile
1               5

<210> SEQ ID NO 49
<211> LENGTH: 9
<212> TYPE: PRT
<213> ORGANISM: Mus musculus

<400> SEQUENCE: 49

Pro Asp Leu Thr Gln Tyr Ala Ile Ile
1               5

<210> SEQ ID NO 50
<211> LENGTH: 9
<212> TYPE: PRT
<213> ORGANISM: Mus musculus

<400> SEQUENCE: 50

Asp Tyr Val Pro Met Glu Gln Pro Arg
1               5

<210> SEQ ID NO 51
<211> LENGTH: 9
<212> TYPE: PRT
<213> ORGANISM: Mus musculus

<400> SEQUENCE: 51

Asp Asp Val Pro Met Glu Gln Pro Arg
1               5

<210> SEQ ID NO 52
<211> LENGTH: 10
<212> TYPE: PRT
<213> ORGANISM: Mus musculus

<400> SEQUENCE: 52

Pro Tyr Leu Thr Gln Tyr Ala Ile Ile Met
1               5                   10

<210> SEQ ID NO 53
<211> LENGTH: 10
<212> TYPE: PRT
<213> ORGANISM: Mus musculus

<400> SEQUENCE: 53

Pro Asp Leu Thr Gln Tyr Ala Ile Ile Met
1               5                   10

<210> SEQ ID NO 54
<211> LENGTH: 10
<212> TYPE: PRT
<213> ORGANISM: Mus musculus

<400> SEQUENCE: 54

Asp Tyr Val Pro Met Glu Gln Pro Arg Pro
1               5                   10

<210> SEQ ID NO 55
<211> LENGTH: 10
<212> TYPE: PRT
```

<213> ORGANISM: Mus musculus

<400> SEQUENCE: 55

Asp Asp Val Pro Met Glu Gln Pro Arg Pro
1               5                   10

<210> SEQ ID NO 56
<211> LENGTH: 11
<212> TYPE: PRT
<213> ORGANISM: Mus musculus

<400> SEQUENCE: 56

Asp Tyr Val Pro Met Glu Gln Pro Arg Pro Pro
1               5                   10

<210> SEQ ID NO 57
<211> LENGTH: 11
<212> TYPE: PRT
<213> ORGANISM: Mus musculus

<400> SEQUENCE: 57

Asp Asp Val Pro Met Glu Gln Pro Arg Pro Pro
1               5                   10

<210> SEQ ID NO 58
<211> LENGTH: 9
<212> TYPE: PRT
<213> ORGANISM: Mus musculus

<400> SEQUENCE: 58

Ser Glu Asp Lys Ile Lys Ala Ile Leu
1               5

<210> SEQ ID NO 59
<211> LENGTH: 9
<212> TYPE: PRT
<213> ORGANISM: Mus musculus

<400> SEQUENCE: 59

Ser Glu Asp Lys Ile Lys Ala Ile Pro
1               5

<210> SEQ ID NO 60
<211> LENGTH: 8
<212> TYPE: PRT
<213> ORGANISM: Mus musculus

<400> SEQUENCE: 60

Leu Lys Ser Glu Glu Lys Thr Leu
1               5

<210> SEQ ID NO 61
<211> LENGTH: 8
<212> TYPE: PRT
<213> ORGANISM: Mus musculus

<400> SEQUENCE: 61

Leu Lys Ser Glu Glu Lys Thr Pro
1               5

<210> SEQ ID NO 62
<211> LENGTH: 11
<212> TYPE: PRT
<213> ORGANISM: Mus musculus

```
<400> SEQUENCE: 62

Lys Pro Ala Leu Lys Ser Glu Glu Lys Thr Leu
1               5                   10

<210> SEQ ID NO 63
<211> LENGTH: 11
<212> TYPE: PRT
<213> ORGANISM: Mus musculus

<400> SEQUENCE: 63

Lys Pro Ala Leu Lys Ser Glu Glu Lys Thr Pro
1               5                   10

<210> SEQ ID NO 64
<211> LENGTH: 10
<212> TYPE: PRT
<213> ORGANISM: Mus musculus

<400> SEQUENCE: 64

Pro Ala Leu Lys Ser Glu Glu Lys Thr Leu
1               5                   10

<210> SEQ ID NO 65
<211> LENGTH: 10
<212> TYPE: PRT
<213> ORGANISM: Mus musculus

<400> SEQUENCE: 65

Pro Ala Leu Lys Ser Glu Glu Lys Thr Pro
1               5                   10

<210> SEQ ID NO 66
<211> LENGTH: 9
<212> TYPE: PRT
<213> ORGANISM: Mus musculus

<400> SEQUENCE: 66

Ala Leu Lys Ser Glu Glu Lys Thr Leu
1               5

<210> SEQ ID NO 67
<211> LENGTH: 9
<212> TYPE: PRT
<213> ORGANISM: Mus musculus

<400> SEQUENCE: 67

Ala Leu Lys Ser Glu Glu Lys Thr Pro
1               5

<210> SEQ ID NO 68
<211> LENGTH: 11
<212> TYPE: PRT
<213> ORGANISM: Mus musculus

<400> SEQUENCE: 68

Ser Trp Ser Ser Arg Arg Ser Leu Leu Gly Leu
1               5                   10

<210> SEQ ID NO 69
<211> LENGTH: 11
<212> TYPE: PRT
<213> ORGANISM: Mus musculus

<400> SEQUENCE: 69
```

Ser Trp Ser Ser Arg Arg Ser Leu Leu Gly Arg
1               5                   10

<210> SEQ ID NO 70
<211> LENGTH: 10
<212> TYPE: PRT
<213> ORGANISM: Mus musculus

<400> SEQUENCE: 70

Gly Phe His Gly Cys Ile His Glu Val Leu
1               5                   10

<210> SEQ ID NO 71
<211> LENGTH: 10
<212> TYPE: PRT
<213> ORGANISM: Mus musculus

<400> SEQUENCE: 71

Gly Phe His Gly Cys Ile His Glu Val Arg
1               5                   10

<210> SEQ ID NO 72
<211> LENGTH: 9
<212> TYPE: PRT
<213> ORGANISM: Mus musculus

<400> SEQUENCE: 72

Gln Val Phe Pro Gly Leu Met Glu Leu
1               5

<210> SEQ ID NO 73
<211> LENGTH: 9
<212> TYPE: PRT
<213> ORGANISM: Mus musculus

<400> SEQUENCE: 73

Gln Val Phe Pro Gly Leu Met Glu Arg
1               5

<210> SEQ ID NO 74
<211> LENGTH: 11
<212> TYPE: PRT
<213> ORGANISM: Mus musculus

<400> SEQUENCE: 74

Thr Thr Thr Pro Gly Gly Arg Pro Pro Tyr Leu
1               5                   10

<210> SEQ ID NO 75
<211> LENGTH: 11
<212> TYPE: PRT
<213> ORGANISM: Mus musculus

<400> SEQUENCE: 75

Thr Thr Thr Pro Gly Gly Arg Pro Pro Tyr Arg
1               5                   10

<210> SEQ ID NO 76
<211> LENGTH: 8
<212> TYPE: PRT
<213> ORGANISM: Mus musculus

<400> SEQUENCE: 76

Val Phe Pro Gly Leu Met Glu Leu
1               5

```
<210> SEQ ID NO 77
<211> LENGTH: 8
<212> TYPE: PRT
<213> ORGANISM: Mus musculus

<400> SEQUENCE: 77

Val Phe Pro Gly Leu Met Glu Arg
1               5

<210> SEQ ID NO 78
<211> LENGTH: 10
<212> TYPE: PRT
<213> ORGANISM: Mus musculus

<400> SEQUENCE: 78

Glu Leu Gln Gly Leu Leu Glu Asp Glu Leu
1               5                   10

<210> SEQ ID NO 79
<211> LENGTH: 10
<212> TYPE: PRT
<213> ORGANISM: Mus musculus

<400> SEQUENCE: 79

Glu Leu Gln Gly Leu Leu Glu Asp Glu Arg
1               5                   10

<210> SEQ ID NO 80
<211> LENGTH: 11
<212> TYPE: PRT
<213> ORGANISM: Mus musculus

<400> SEQUENCE: 80

Lys Leu Gln Arg Gln Tyr Arg Ser Pro Arg Leu
1               5                   10

<210> SEQ ID NO 81
<211> LENGTH: 11
<212> TYPE: PRT
<213> ORGANISM: Mus musculus

<400> SEQUENCE: 81

Lys Leu Gln Arg Gln Tyr Arg Ser Pro Arg Arg
1               5                   10

<210> SEQ ID NO 82
<211> LENGTH: 9
<212> TYPE: PRT
<213> ORGANISM: Mus musculus

<400> SEQUENCE: 82

Ser Tyr Met Leu Gln Ala Leu Cys Ile
1               5

<210> SEQ ID NO 83
<211> LENGTH: 9
<212> TYPE: PRT
<213> ORGANISM: Mus musculus

<400> SEQUENCE: 83

Leu Asp Met Leu Gln Ala Leu Cys Ile
1               5
```

```
<210> SEQ ID NO 84
<211> LENGTH: 11
<212> TYPE: PRT
<213> ORGANISM: Mus musculus

<400> SEQUENCE: 84

Ser Tyr Met Leu Gln Ala Leu Cys Ile Pro Thr
1               5                   10

<210> SEQ ID NO 85
<211> LENGTH: 11
<212> TYPE: PRT
<213> ORGANISM: Mus musculus

<400> SEQUENCE: 85

Leu Asp Met Leu Gln Ala Leu Cys Ile Pro Thr
1               5                   10

<210> SEQ ID NO 86
<211> LENGTH: 10
<212> TYPE: PRT
<213> ORGANISM: Mus musculus

<400> SEQUENCE: 86

Ser Tyr Met Leu Gln Ala Leu Cys Ile Pro
1               5                   10

<210> SEQ ID NO 87
<211> LENGTH: 10
<212> TYPE: PRT
<213> ORGANISM: Mus musculus

<400> SEQUENCE: 87

Leu Asp Met Leu Gln Ala Leu Cys Ile Pro
1               5                   10

<210> SEQ ID NO 88
<211> LENGTH: 8
<212> TYPE: PRT
<213> ORGANISM: Mus musculus

<400> SEQUENCE: 88

Ser Tyr Met Leu Gln Ala Leu Cys
1               5

<210> SEQ ID NO 89
<211> LENGTH: 8
<212> TYPE: PRT
<213> ORGANISM: Mus musculus

<400> SEQUENCE: 89

Leu Asp Met Leu Gln Ala Leu Cys
1               5

<210> SEQ ID NO 90
<211> LENGTH: 10
<212> TYPE: PRT
<213> ORGANISM: Mus musculus

<400> SEQUENCE: 90

Ala Tyr Ile Leu Ala Ala Leu Thr Lys Leu
1               5                   10

<210> SEQ ID NO 91
<211> LENGTH: 10
```

```
<212> TYPE: PRT
<213> ORGANISM: Mus musculus

<400> SEQUENCE: 91

Ala Asp Ile Leu Ala Ala Leu Thr Lys Leu
1               5                   10

<210> SEQ ID NO 92
<211> LENGTH: 10
<212> TYPE: PRT
<213> ORGANISM: Mus musculus

<400> SEQUENCE: 92

Pro Tyr Leu Val Leu Lys Phe Gly Pro Val
1               5                   10

<210> SEQ ID NO 93
<211> LENGTH: 10
<212> TYPE: PRT
<213> ORGANISM: Mus musculus

<400> SEQUENCE: 93

Pro Asp Leu Val Leu Lys Phe Gly Pro Val
1               5                   10

<210> SEQ ID NO 94
<211> LENGTH: 10
<212> TYPE: PRT
<213> ORGANISM: Mus musculus

<400> SEQUENCE: 94

Leu Tyr Glu Ala Gly Val Thr Asp Glu Val
1               5                   10

<210> SEQ ID NO 95
<211> LENGTH: 10
<212> TYPE: PRT
<213> ORGANISM: Mus musculus

<400> SEQUENCE: 95

Leu Asp Glu Ala Gly Val Thr Asp Glu Val
1               5                   10

<210> SEQ ID NO 96
<211> LENGTH: 8
<212> TYPE: PRT
<213> ORGANISM: Mus musculus

<400> SEQUENCE: 96

His Tyr Leu Gln Gly Ser Asn Ala
1               5

<210> SEQ ID NO 97
<211> LENGTH: 8
<212> TYPE: PRT
<213> ORGANISM: Mus musculus

<400> SEQUENCE: 97

His Asp Leu Gln Gly Ser Asn Ala
1               5

<210> SEQ ID NO 98
<211> LENGTH: 9
<212> TYPE: PRT
<213> ORGANISM: Mus musculus
```

```
<400> SEQUENCE: 98

Leu Tyr His Thr Arg Pro Thr Ala Leu
1               5

<210> SEQ ID NO 99
<211> LENGTH: 9
<212> TYPE: PRT
<213> ORGANISM: Mus musculus

<400> SEQUENCE: 99

Leu Asp His Thr Arg Pro Thr Ala Leu
1               5

<210> SEQ ID NO 100
<211> LENGTH: 11
<212> TYPE: PRT
<213> ORGANISM: Mus musculus

<400> SEQUENCE: 100

Ile Tyr Gly Val Val Ala Arg Asn Arg Ala Leu
1               5                   10

<210> SEQ ID NO 101
<211> LENGTH: 11
<212> TYPE: PRT
<213> ORGANISM: Mus musculus

<400> SEQUENCE: 101

Ile Asp Gly Val Val Ala Arg Asn Arg Ala Leu
1               5                   10

<210> SEQ ID NO 102
<211> LENGTH: 9
<212> TYPE: PRT
<213> ORGANISM: Mus musculus

<400> SEQUENCE: 102

Ala Tyr Ala Lys Gln Phe Ala Ala Ile
1               5

<210> SEQ ID NO 103
<211> LENGTH: 9
<212> TYPE: PRT
<213> ORGANISM: Mus musculus

<400> SEQUENCE: 103

Ala Asp Ala Lys Gln Phe Ala Ala Ile
1               5

<210> SEQ ID NO 104
<211> LENGTH: 10
<212> TYPE: PRT
<213> ORGANISM: Mus musculus

<400> SEQUENCE: 104

Ser Tyr Cys Glu Pro Ala Leu Asn Gln Ala
1               5                   10

<210> SEQ ID NO 105
<211> LENGTH: 10
<212> TYPE: PRT
<213> ORGANISM: Mus musculus

<400> SEQUENCE: 105
```

Ser Asp Cys Glu Pro Ala Leu Asn Gln Ala
1               5                   10

<210> SEQ ID NO 106
<211> LENGTH: 11
<212> TYPE: PRT
<213> ORGANISM: Mus musculus

<400> SEQUENCE: 106

Val Tyr Leu Thr Cys Arg Leu Glu Lys Pro Ala
1               5                   10

<210> SEQ ID NO 107
<211> LENGTH: 11
<212> TYPE: PRT
<213> ORGANISM: Mus musculus

<400> SEQUENCE: 107

Val Asp Leu Thr Cys Arg Leu Glu Lys Pro Ala
1               5                   10

<210> SEQ ID NO 108
<211> LENGTH: 9
<212> TYPE: PRT
<213> ORGANISM: Mus musculus

<400> SEQUENCE: 108

Lys Tyr Met Ser Met Leu Glu Glu Arg
1               5

<210> SEQ ID NO 109
<211> LENGTH: 9
<212> TYPE: PRT
<213> ORGANISM: Mus musculus

<400> SEQUENCE: 109

Lys Asp Met Ser Met Leu Glu Glu Arg
1               5

<210> SEQ ID NO 110
<211> LENGTH: 10
<212> TYPE: PRT
<213> ORGANISM: Mus musculus

<400> SEQUENCE: 110

Pro Tyr Lys Arg Leu Lys Ala Glu Pro Ala
1               5                   10

<210> SEQ ID NO 111
<211> LENGTH: 10
<212> TYPE: PRT
<213> ORGANISM: Mus musculus

<400> SEQUENCE: 111

Pro Asp Lys Arg Leu Lys Ala Glu Pro Ala
1               5                   10

<210> SEQ ID NO 112
<211> LENGTH: 10
<212> TYPE: PRT
<213> ORGANISM: Mus musculus

<400> SEQUENCE: 112

Asp Tyr Ile Ile Glu Phe Ala His Arg Val

```
1               5                   10
```

<210> SEQ ID NO 113
<211> LENGTH: 10
<212> TYPE: PRT
<213> ORGANISM: Mus musculus

<400> SEQUENCE: 113

```
Asp Asp Ile Ile Glu Phe Ala His Arg Val
1               5                   10
```

<210> SEQ ID NO 114
<211> LENGTH: 9
<212> TYPE: PRT
<213> ORGANISM: Mus musculus

<400> SEQUENCE: 114

```
Gly Tyr Ser Val Leu His Leu Ala Ile
1               5
```

<210> SEQ ID NO 115
<211> LENGTH: 9
<212> TYPE: PRT
<213> ORGANISM: Mus musculus

<400> SEQUENCE: 115

```
Gly Asp Ser Val Leu His Leu Ala Ile
1               5
```

<210> SEQ ID NO 116
<211> LENGTH: 10
<212> TYPE: PRT
<213> ORGANISM: Mus musculus

<400> SEQUENCE: 116

```
Ile Tyr Gly Val Val Ala Arg Asn Arg Ala
1               5                   10
```

<210> SEQ ID NO 117
<211> LENGTH: 10
<212> TYPE: PRT
<213> ORGANISM: Mus musculus

<400> SEQUENCE: 117

```
Ile Asp Gly Val Val Ala Arg Asn Arg Ala
1               5                   10
```

<210> SEQ ID NO 118
<211> LENGTH: 11
<212> TYPE: PRT
<213> ORGANISM: Mus musculus

<400> SEQUENCE: 118

```
Leu Tyr Tyr Glu Arg Ile His Lys Lys Met Leu
1               5                   10
```

<210> SEQ ID NO 119
<211> LENGTH: 11
<212> TYPE: PRT
<213> ORGANISM: Mus musculus

<400> SEQUENCE: 119

```
Leu Asp Tyr Glu Arg Ile His Lys Lys Met Leu
1               5                   10
```

```
<210> SEQ ID NO 120
<211> LENGTH: 10
<212> TYPE: PRT
<213> ORGANISM: Mus musculus

<400> SEQUENCE: 120

Ser Tyr Arg Leu Pro Ser Ser Arg Lys Lys
1               5                   10

<210> SEQ ID NO 121
<211> LENGTH: 10
<212> TYPE: PRT
<213> ORGANISM: Mus musculus

<400> SEQUENCE: 121

Ser Asp Arg Leu Pro Ser Ser Arg Lys Lys
1               5                   10

<210> SEQ ID NO 122
<211> LENGTH: 9
<212> TYPE: PRT
<213> ORGANISM: Mus musculus

<400> SEQUENCE: 122

Leu Tyr Val Ser Lys Leu Asn Gly Pro
1               5

<210> SEQ ID NO 123
<211> LENGTH: 9
<212> TYPE: PRT
<213> ORGANISM: Mus musculus

<400> SEQUENCE: 123

Leu Asp Val Ser Lys Leu Asn Gly Pro
1               5

<210> SEQ ID NO 124
<211> LENGTH: 9
<212> TYPE: PRT
<213> ORGANISM: Mus musculus

<400> SEQUENCE: 124

Leu Tyr Glu Ala Gly Val Thr Asp Glu
1               5

<210> SEQ ID NO 125
<211> LENGTH: 9
<212> TYPE: PRT
<213> ORGANISM: Mus musculus

<400> SEQUENCE: 125

Leu Asp Glu Ala Gly Val Thr Asp Glu
1               5

<210> SEQ ID NO 126
<211> LENGTH: 8
<212> TYPE: PRT
<213> ORGANISM: Mus musculus

<400> SEQUENCE: 126

Leu Tyr Asp Val Asp Ala Ala Phe
1               5

<210> SEQ ID NO 127
```

```
<211> LENGTH: 8
<212> TYPE: PRT
<213> ORGANISM: Mus musculus

<400> SEQUENCE: 127

Leu Asp Asp Val Asp Ala Ala Phe
1               5

<210> SEQ ID NO 128
<211> LENGTH: 8
<212> TYPE: PRT
<213> ORGANISM: Mus musculus

<400> SEQUENCE: 128

Glu Tyr Leu Asp Leu Gln Thr Gln
1               5

<210> SEQ ID NO 129
<211> LENGTH: 8
<212> TYPE: PRT
<213> ORGANISM: Mus musculus

<400> SEQUENCE: 129

Glu Asp Leu Asp Leu Gln Thr Gln
1               5

<210> SEQ ID NO 130
<211> LENGTH: 11
<212> TYPE: PRT
<213> ORGANISM: Mus musculus

<400> SEQUENCE: 130

Ala Tyr Ile Leu Ala Ala Leu Thr Lys Leu Gln
1               5                   10

<210> SEQ ID NO 131
<211> LENGTH: 11
<212> TYPE: PRT
<213> ORGANISM: Mus musculus

<400> SEQUENCE: 131

Ala Asp Ile Leu Ala Ala Leu Thr Lys Leu Gln
1               5                   10

<210> SEQ ID NO 132
<211> LENGTH: 9
<212> TYPE: PRT
<213> ORGANISM: Mus musculus

<400> SEQUENCE: 132

Glu Tyr Leu Asp Leu Gln Thr Gln Gly
1               5

<210> SEQ ID NO 133
<211> LENGTH: 9
<212> TYPE: PRT
<213> ORGANISM: Mus musculus

<400> SEQUENCE: 133

Glu Asp Leu Asp Leu Gln Thr Gln Gly
1               5

<210> SEQ ID NO 134
<211> LENGTH: 8
<212> TYPE: PRT
```

```
<213> ORGANISM: Mus musculus

<400> SEQUENCE: 134

Ala Tyr Ala Lys Gln Phe Ala Ala
1               5

<210> SEQ ID NO 135
<211> LENGTH: 8
<212> TYPE: PRT
<213> ORGANISM: Mus musculus

<400> SEQUENCE: 135

Ala Asp Ala Lys Gln Phe Ala Ala
1               5

<210> SEQ ID NO 136
<211> LENGTH: 9
<212> TYPE: PRT
<213> ORGANISM: Mus musculus

<400> SEQUENCE: 136

Ala Tyr Arg Leu Glu Gly Asp Arg Ser
1               5

<210> SEQ ID NO 137
<211> LENGTH: 9
<212> TYPE: PRT
<213> ORGANISM: Mus musculus

<400> SEQUENCE: 137

Ala Asp Arg Leu Glu Gly Asp Arg Ser
1               5

<210> SEQ ID NO 138
<211> LENGTH: 9
<212> TYPE: PRT
<213> ORGANISM: Mus musculus

<400> SEQUENCE: 138

Leu Asp Met Leu Gln Ala Leu Cys Ile
1               5
```

IDENTIFICATION OF IMMUNOLOGICALLY PROTECTIVE NEO-EPITOPES FOR THE TREATMENT OF CANCERS

CROSS REFERENCE TO RELATED APPLICATIONS

This application is a divisional of U.S. application Ser. No. 16/560,336 filed on Sep. 4, 2019, which is a continuation of U.S. application Ser. No. 15/501,919, filed on Feb. 16, 2017, which is a National Stage application of PCT/US2015/048345, filed on Sep. 3, 2015, which claims the benefit of U.S. Provisional Application No. 62/048,561, filed on Sep. 10, 2014, each of which is incorporated by reference in their entirety herein.

FIELD OF THE DISCLOSURE

The present disclosure relates to methods of identifying immunologically protective tumor-specific epitopes, pharmaceutical compositions such as vaccine compositions comprising immunologically protective tumor-specific epitope peptides, nucleic acid molecules encoding such peptides, and the use of such peptides or nucleic acids in immunotherapy of cancer.

BACKGROUND

Despite profound advances in the understanding the biology of cancer, the treatment of the most common cancers of adults, such as those of the breast, prostate, lung, colon, ovaries, etc., remains far from satisfactory. Without a doubt, there have been major advances; equally without a doubt, a very large medical need remains unmet. Successful treatment of any disease requires a clear understanding of that which is unique about the disease, followed by finding a way to attack the disease at the point of its uniqueness. This principle has been the basis of all major successes in medicine.

Cancers, in contrast to bacterial infections, for example, are not foreign entities; they are derived from our own self. Because of the overwhelming commonality between cancers and our healthy tissues, cancer has been approached by trying to find biological pathways which the cancers use, and which our normal bodies use less, i.e., to aim for selectivity as opposed to specificity. This approach, illustrated by chemotherapy, is the major nonsurgical approach to cancer therapy today. It is somewhat effective, but since the efficacy is not based on specificity but on selectivity, chemotherapy attacks the normal tissues as well, leading to the well-known side effects of the treatment, which also limit its use.

Recent years have seen increasingly sophisticated tools of chemotherapy, but the fundamental problem that chemotherapy is not specific to cancer but only selective for it remains, and thus it has been for several decades.

An exception that proves the rule is imatinib, a treatment for a common adult leukemia. This kind of leukemia, chronic myelogenous leukemia or CML, results from a very specific change in the blood cells. The change is known and it is also known that the change is only in the leukemia cells. The drug imatinib specifically targets this change and is enormously effective against CML. Unfortunately, CML remains a rather unique example where the specificity can be and has been defined; fortunately, it is also a prime example of the fact that the definition of specificity can lead to highly effective cancer therapy.

What is needed are methods of determining the basis of cancer specificity and then applying this specificity to develop successful, non-toxic therapies.

BRIEF SUMMARY

In one aspect, a method of identifying immunologically protective neo-epitopes in a cancer patient, comprises:
providing a putative neo-epitope set,
determining the conformational stability of at least a portion of each putative neo-epitope in the putative neo-epitope set bound to an MHC I or MHC II protein,
selecting from the putative neo-epitope set the immunologically protective neo-epitopes, wherein the immunologically protective neo-epitopes have higher conformational stability compared to the corresponding wild type epitope when bound to the MHC I or MHC II protein,
optionally producing a pharmaceutical composition comprising a pharmaceutically acceptable carrier and one or more immunologically protective neo-epitope peptides, one or more polypeptides containing the immunologically protective neo-epitopes, or one or more polynucleotides encoding the one or more immunologically protective neo-epitopes, and
optionally administering the pharmaceutical composition to the cancer patient.

In a specific aspect, the putative neo-epitope set is determined using the Differential Agretopic Index as described herein.

In another specific aspect, determining the conformational stability of at least a portion of each putative neo-epitope in the putative neo-epitope set bound to an MHC I or MHC II protein comprises determining the conformational fluctuations of each epitope in the putative neo-epitope set bound to an MHC I or MHC II protein.

In another aspect, a pharmaceutical composition comprises a pharmaceutically acceptable carrier and one or more immunologically protective neo-epitopes peptides, one or more polypeptides containing the immunologically protective neo-epitopes, or one or more polynucleotides encoding the one or more immunologically protective neo-epitopes, wherein the one or more immunologically protective neo-epitopes are selected from a putative neo-epitope set, wherein the putative neo-epitope set does not include epitopes from known cancer-causing pathways, wherein the putative neo-epitope set is specific to a tumor from a cancer patient, and wherein the conformational stability of each immunologically protective neo-epitope bound to an MHC I or MHC II protein as determined by molecular modeling or by experiment is higher compared each corresponding wild type epitope.

tetramer. Tetramer positive cells were counted in CD8+ gate. (C) Mice were immunized with irradiated Meth A cells. Left, six days later, inguinal LN cells were stimulated overnight without peptide, irrelevant Prpf31 peptide or Tnpo3 peptide. % activated effector CD8+ cells are shown. Right, splenocytes were stimulated in vitro in multiple rounds with 1 μM of indicated peptides for a total of 19 days. Irrelevant peptide from Prpf31 was used as a control. Five days after stimulation, cells were tested for the responsiveness to indicated peptides. Typically, for each sample, 150,000 lymphocytes, or at least 19,000 CD8+CD4− cells, were acquired. Although <0.1% Tnpo3-specific CD8+ T cells are truly small responses, we consider it real because ex vivo responses are bound to be weak, the response is statistically significant, and the enhanced Tnpo3-specific responses (>1.2%) were detected after weekly in vitro stimulation with Tnpo3 peptide (right panel). See FIG. 10 for FACS gating strategy and representative primary data. (D) Mice were injected with 200,000 Meth A cells on the right flank. Twenty-one days later, tumor-draining LNs and contralateral LNs were harvested and stained with anti-CD8 antibody and Tnpo3 and Nfkb1 tetramers $K^d$/SYMLQALCI (SEQ ID NO: 2) and $K^d$/GYSVLHLAI (SEQ ID NO: 3) respectively (left and middle panels). Splenocytes were used to purify CD8+ cells to assess the responsiveness to mutant Tnpo3-pulsed cells (Tnpo3) or Meth A cells (Meth A) by ELISPOT assay with no peptide (No pep) stimulation as negative control (right panel). (E) Naïve mice or Tnpo3-mutant peptide-immunized mice were challenged with Meth A cells. Additionally, naïve and immunized mice were treated with anti-CD25 antibody or anti-CTLA-4 antibody as indicated. AUC for each group is plotted, and complete tumor growth curves for all the mice in all groups are shown. Between four and six mice per group were used in each experiment, and each experiment was repeated between three and five times.

Figure 1:
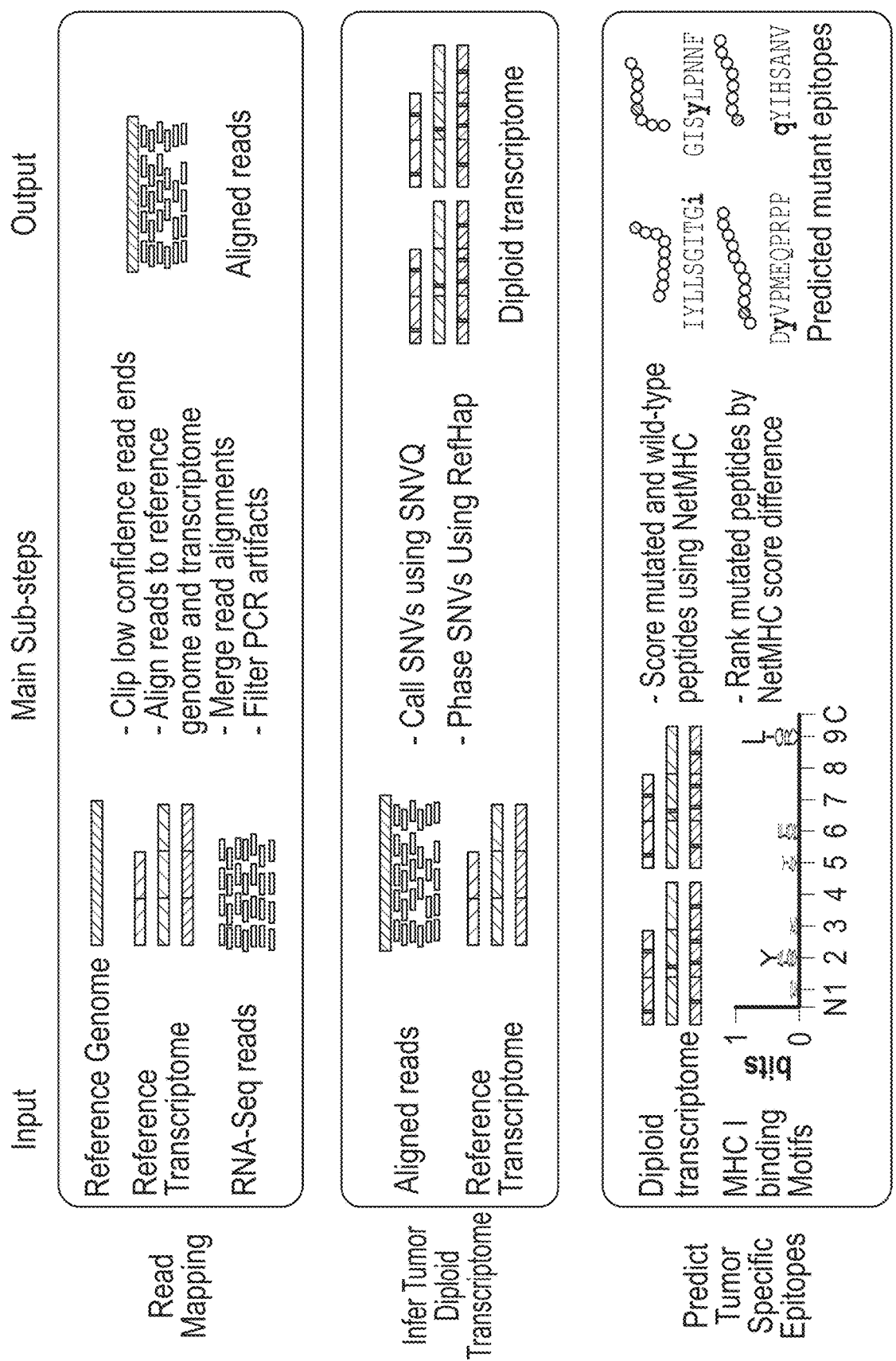
FIG. 1 shows a schematic representation of the Epi-Seq bioinformatics pipeline used to identify tumor specific epitopes from RNA-Seq reads.
Figure 9:
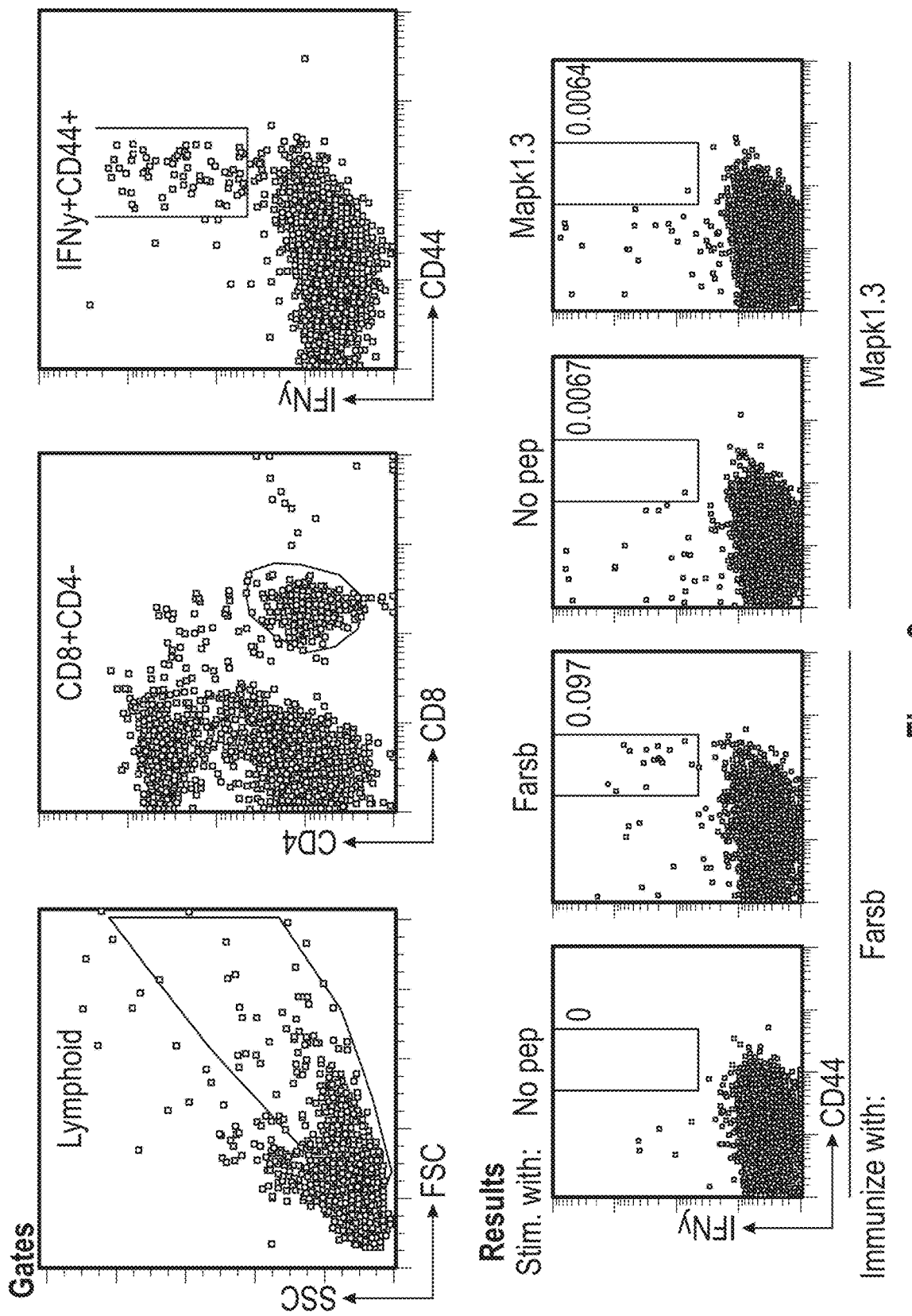

FIG. 9 shows FACS gating strategy and representative primary data for FIG. 1. Gating strategy for lymphoid cells, CD8+CD4− cells and IFNγ+CD44+ cells stimulated with a cognate peptide, is shown. Also shown are the examples of an immunogenic peptide (Farsb) with a specific response of 0.097% and a non-immunogenic peptide (Mapk1.3) with a 10-fold less background of 0.0064%. In both cases, cells without peptide stimulation were used as a negative control. For each sample, total 95,000-129,000 lymphocytes, or 14,500-17,000 CD8+CD4− cells, were acquired.

Figure 10:
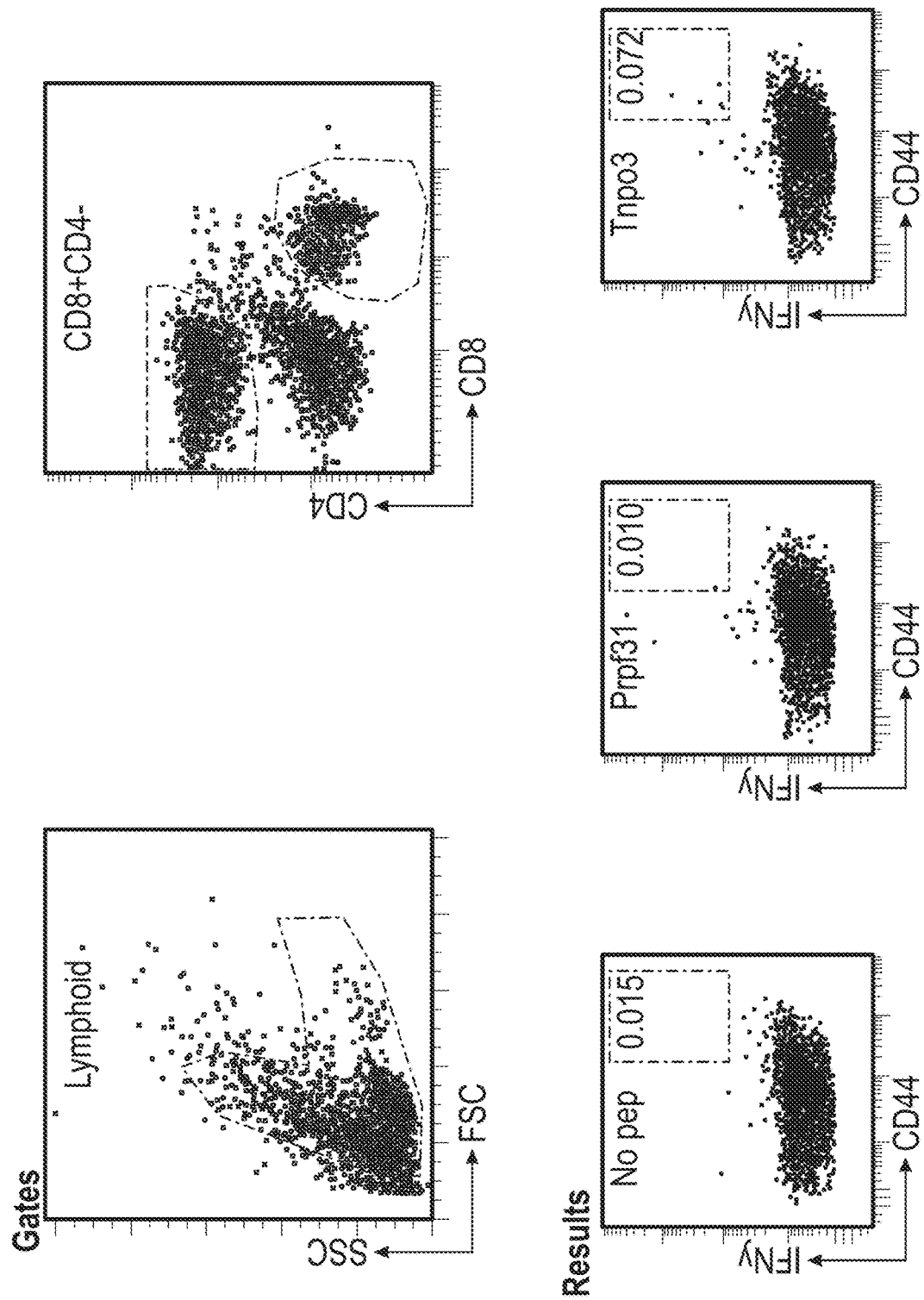

FIG. 10 shows that FACS gating strategy and representative primary data for FIG. 8C (left panel). Gating strategy for lymphoid and CD8+CD4− cells (top two panels) and representative FACS plots for responses against no-pep, control peptide Prpf31 and Tnpo3 peptide (bottom three panels). Note that the response in lack of stimulation, and in response to stimulation by irrelevant peptide control is identical, and that the response to Tnpo3 is 5-7 times higher than background. For each sample, total 150,000 lymphocytes, or a minimum of 19,000 CD8+CD4− cells, were acquired.

DETAILED DESCRIPTION

The idea that neo-epitopes created by random mutations in tumor cells, termed as individually specific tumor antigens or unique antigens, are responsible for the immunogenicity of tumors has been around for over 20 years. Neo-epitopes are defined herein as mutated regions of an antigen generated by modification of the original antigen. There has been strong experimental evidence for their existence and activity in murine and human tumors, and mathematic modeling has predicted the existence of tens to hundreds of neo-epitopes in individual human tumors. The recent revolution in high throughput DNA sequencing and accompanying bio-informatics approaches has finally made it possible to actually identify the individually specific neo-epitopes in individual cancers. Using this methodology, it has been shown that human breast and colon cancers as well as chronic myelogenous leukemia harbor tens of putative mutational neo-epitopes. A genomic/bioinformatic approach to identify such neo-epitopes in a mouse melanoma also led to identification of hundreds of neo-epitopes. A similar approach led to identification of a neo-epitope in a methylcholanthrene-induced sarcoma in an immuno-compromised mouse; transplantation of this tumor into an immune-competent animal led to epitope-dependent tumor regression. In human studies, association of favorable clinical course of disease with a dominant immune response to mutated neo-epitopes has been demonstrated. These growing numbers of studies suggest strongly that the host immune response to mutant neo-epitopes plays the dominant role in protection of the host from tumor growth.

The opportunity to identify a vast number of putative neo-epitopes from individual human tumors creates a corresponding problem: how does one differentiate and identify actual tumor protective neo-epitopes from among the large number of putative neo-epitopes identified in silico? The problem is daunting in scale because an examination of the tumor transcriptomes and their comparison with normal exomes in the TCGA database shows that many tumors harbor hundreds of putative neo-epitopes. Presumably, only a small fraction of these virtual neo-epitopes is immuno-protective against cancer.

This question has been addressed before in viral systems wherein a systematic analysis of the putative and real epitopes of the vaccinia virus has been performed. This study revealed the magnitude of the problem: starting from all possible 9-10 amino acid peptides encoded by the vaccinia genome, only 2.5% are high affinity binders to a given HLA allele. Of the high affinity binders, half elicit a CD8 response. Of these, only 15% are naturally processed and presented. Finally, observed little correlation was observed between the dominance of an epitope with HLA-peptide affinity, HLA-peptide stability, TCR avidity, or the quantity of processed epitope. Thus, without the benefit of information from T cell responses, one would be unable to start from the vaccinia genome and identify useful epitopes.

The problem is orders of magnitude more complex for identifying useful epitopes from cancer genomes because the mammalian genome is considerably larger than that of vaccinia. Moreover, viral genomes are entirely non-self, while the cancer genomes are mutated-self; hence the neo-epitopes may be cross-reactive with self, and tolerance or suppression mechanisms are highly likely to come into play.

Described herein is a systematic analysis of the transcriptomes and CD8 immunomes of tumors, and the rules that govern the immunogenicity and tumor-protective ability of mutation-generated neo-epitopes. This effort has led to surprising observations regarding MHC I-peptide interactions that distinguish the recognition of neo-epitopes from that of viral epitopes, and a recognition that the proportion of putative mutational neo-epitopes that is translatable in vivo is far smaller than the corresponding proportion for viral systems.

Specifically, in WO2014/052707, incorporated herein by reference for its teaching of the determination of tumor-specific epitopes, a novel index called the Differential Agretopic Index (DAI) was described. The DAI is an improvement over algorithms such as NetMHC in the selection of tumor-specific epitopes, however, it was found that many of the selected tumor-specific epitopes have lower immunogenicity than expected. The inventors of the present application have found that conformational stability of the peptides when the peptide is bound to an MHC protein was a strong predictor of immunological outcome. Specifically, the immunogenic neo-epitopes were unexpectedly found to have higher conformational stability than the corresponding wild type sequence. That is, the mutations that result in higher conformational stability of the peptide relative to the wild type peptide are more likely to be immunogenic.

The results presented herein reveal a plurality of tumor-specific antigenic epitopes. Using novel tools reported herein, the small number of neo-epitopes (among the vast numbers of potential neo-epitopes) that truly elicit immunological protection against tumor growth were identified. The application of the method is described herein for two independent tumors. It is noted that while the selection of the putative neo-epitope set is illustrated using the DAI algorithm, the methods disclosed herein are not limited to epitope sets identified using this algorithm. In actuality, the pipeline, including the DAI algorithm, was first derived empirically on the data from the Meth A tumor, and was then tested on CMS5. The anti-tumor activity predicted from the DAI algorithm is significantly stronger in CMS5 than in Meth A; this variation is most likely a reflection of the immuno-suppressive mechanisms unique to the Meth A tumor, and thus un-related to the merits of the DAI algorithm per se. The DAI algorithm has since been tested in yet another mouse tumor, the B16 melanoma, and data on T cell responses in this line as well, are consistent with significant superiority of DAI over NetMHC alone. Although the present study is focused on identification of MHC I-restricted epitopes of CD8 T cells, the analysis can also be extended to MHC II-restricted epitopes of CD4 T cells.

Although T cells play an unambiguously central role in cancer immunity, they have been poor probes for identification of immuno-protective epitopes thus far. Extensive and laborious analyses of T cell-defined tumor-specific antigens of Meth A and CMS5 sarcomas over the years managed to yield a total of five epitopes, none of which elicit particularly robust tumor rejection; in contrast, this single study has un-covered nearly a dozen, potent tumor-protective epitopes of these two tumors. It is instructive to ponder the reason for this discrepancy. The use of T cells as probes inherently requires generation of T cell lines or clones, which itself is a highly selective process. Without being held to theory it is believed that the diversity of effector T cells in vivo is not readily captured by the T cell lines or clones generated in vitro, leading to a distorted, and sparse, view of the T cell immunomes of tumors. The genomics-driven analysis of the immunome described here cuts through the bias in selection of T cells and thus illuminates the entire field of neo-epitopes.

In one aspect, as specifically described herein, the DAI score (the numerical difference between the NetMHC scores of the mutated epitope and its un-mutated counterpart) allows significant enrichment for the extremely small number of truly immuno-protective neo-epitopes from among the hundreds of putative neo-epitopes identified by the NetMHC algorithm. The demonstrated utility of the DAI score underscores the validity of its premise: a tumor-protective immune response requires neo-epitopes that differ from their wild type counterparts, and the DAI score is a means to quantify and rank such differences. Understandably, since existing ideas about immunogenicity are derived entirely from the study of viral and model antigens, which have no self-counterparts, there was no necessity to devise a DAI for their studies. As follows from the design of the NetMHC algorithm, amino acid substitutions at primary anchor residues make for the biggest contributions to the DAI. Indeed, every neo-epitope with a high DAI ranking replaces aspartic acid with tyrosine at position 2 or proline/arginine at the C-terminus with leucine. From structural considerations, these substitutions would be expected to significantly impact peptide binding, as tyrosine at P2 and leucine at the peptide C-terminus are the most optimal $K^d$ anchor residues (indeed, aspartic acid at P2 or arginine at the C-terminus would be expected to be considerably unfavorable due to substantial charge repulsion). Peptide conformational stability, expressed as the fluctuations observed during molecular dynamics simulations, but also determinable via other computational and experimental techniques, is another tool that suggests a novel correlate with immunogenicity. The majority of the neo-epitopes with high DAI rankings are predicted to interact with the MHC in a more stable fashion than their wild-type counterparts; in these cases, alteration of the anchor residues yields a more rigidly bound peptide. The effect of anchor modification on peptide conformational stability has been noted previously, and notably, increased peptide flexibility correlates with a loss of immunogenicity. This may occur by reducing the opportunities for productive interactions with T cell receptors or increasing the lifetime of the MHC-bound peptide. Of course, methods other than the DAI can be used to determine putative neo-epitope sets, and other methods than fluctuations observed during molecular dynamics simulations can be used to assess the conformational stability of the neo-epitopes.

A most surprising observation that emerges from the study presented herein is that 10/10 neo-epitopes that elicit protective immunity are classified as non-binders of $K^d$ by NetMHC (cut-off value of 8.72). Correspondingly, the affinity of 9/10 neo-epitopes for $K^d$ is well over, 100 nM or over 500 nM, the traditional threshold for fruitful interaction of viral epitopes with MHC I molecules. In three of three instances tested, these presumed "non-binders" elicit classical CD8 T cell-dependent tumor immunity. This observation challenges some of our basic assumptions about MHC I-peptide-T cell receptor interactions and exposes a far wider universe of potential neo-antigens than assumed thus far.

Figure 5:
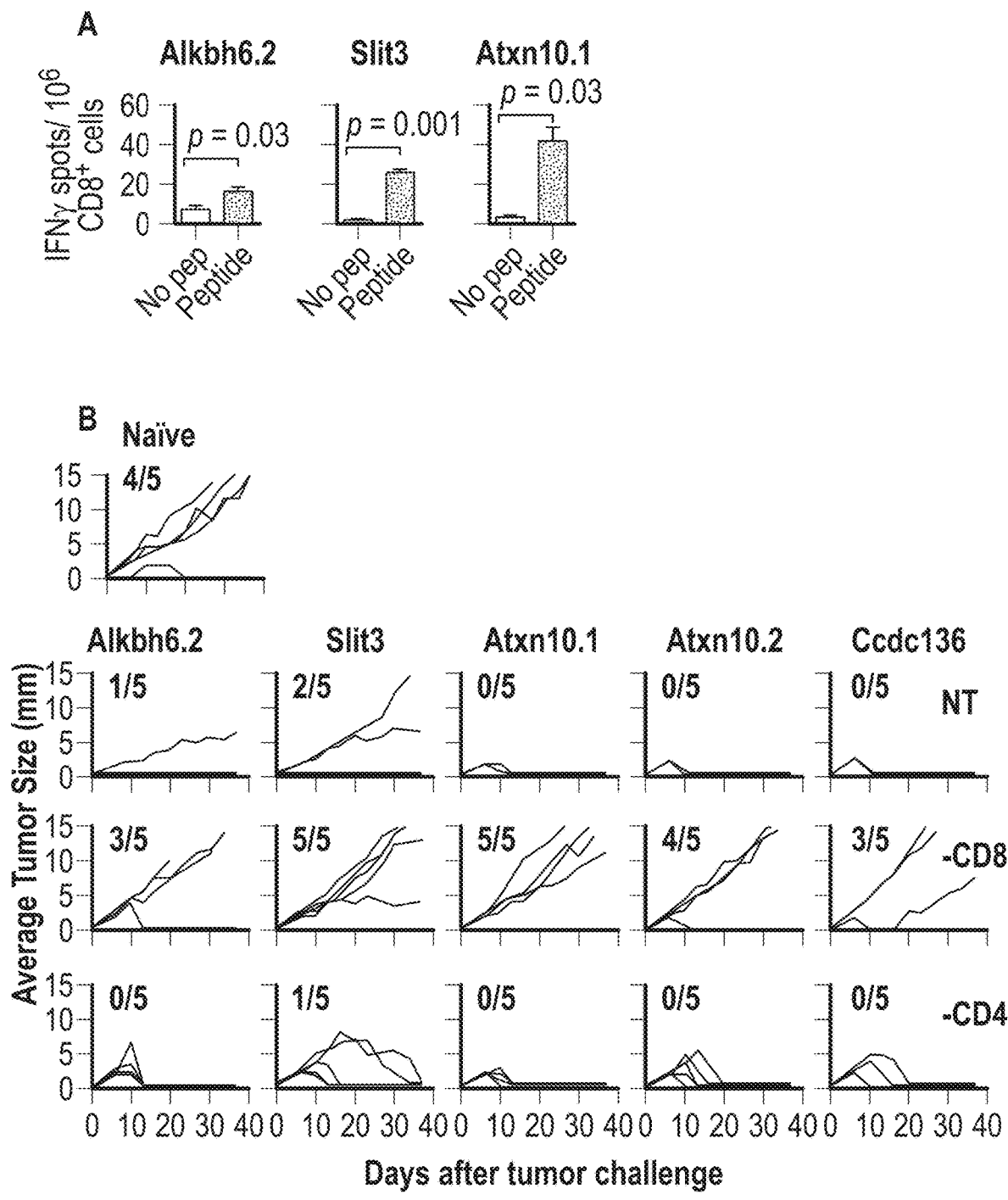
FIG. 5 shows that protective tumor immunity elicited by tumor-specific peptides is CD8-dependent. (A) Mice were immunized with mutant peptides Alkbh6.2, Slit3 and Atxn10.1, Atxn 10.2 and cdc136 as listed in Table 5. The dLNs were not stimulated or stimulated in vitro with the cognate peptides for 20 h and were analyzed by ELISPOT. Data for mice immunized with Alkbh6.2, Slit3 and Atxn10.1 peptides are shown. Mice immunized with Atxn 10.2 and cdc136 did not elicit a detectable CD8 response as also indicated in Table 6. (B) Naïve mice or mice immunized twice with indicated peptides (Alkbh6.2, Slit3, Atxn10.1, Atxn 10.2 and cdc136) were challenged intradermally with 300,000 live CMS5 tumor cells, and tumor growth was monitored. Immunized mice were not depleted (NT), depleted of CD8 or CD4 cells, as indicated, and as described in Experimental Procedures. Each line shows the kinetics of tumor growth in a single mouse. The experiments were carried out three times.

The observed dissociation between detectable CD8 responses and immuno-protection (Table 6) from tumor growth merits comment. The neo-epitopes that elicit immuno-protection and a CD8 response are straightforward and require no comment. The neo-epitopes that elicit immuno-protection but not a detectable CD8 response (FIG. 5) may also be understood with the explanation that the CD8 response elicited is too weak to be detected by the ELISPOT assay, thus highlighting the need for developing more sensitive assays for CD8 cells and their activities. It is, however, the epitopes that elicit potent CD8 responses but not immuno-protection that are difficult to understand. However, some data in Table 6 may provide guidance in thinking about this dissociation. Note the neo-epitopes Tnpo3.1, 3.2, 3.3 and 3.4 for Meth A in Table 6. They share the same N terminal mutations (sy/LD) but differ in the extent of their extension on the C termini. While the first three elicit strong CD8 responses, Tnpo3.4 does not. More interestingly, of the three neo-epitopes that are immunogenic, only one, Tnpo3.1 elicits protection from tumor growth. It is conceivable that Tnpo3.1 is the only neo-epitope that is naturally presented, while the others are not. This entirely testable hypothesis provides a framework for testing the dissociation between T cell responses and immuno-protection.

Unexpectedly, not a single WT epitope among the more than 100 tested (66 epitopes listed in Tables 5 and 6, and over 35 additional epitopes) elicited a measurable, amplifiable CD8 immune response. The immune responses, when detected after a first immunization, were abrogated, rather than enhanced, after a second immunization, consistent with them being peripherally tolerized responses. This study represents perhaps the largest in which the immune responses to such a large number of self-epitopes have been systematically tested and testifies strongly to the powerful scope of mechanisms of negative selection and peripheral tolerance.

With the advent of high throughput and inexpensive DNA sequencing, it is now possible to routinely sequence the exomes of cancers and normal tissues of each cancer patient and compare the two to identify cancer-specific mis-sense mutations. The NetMHC or other such commonly available algorithms can then be used to identify the potential neo-epitopes generated by the mis-sense mutations, for each of the three to six HLA I alleles of each patient. Peptides corresponding to the neo-epitopes can then be chemically synthesized and used to immunize patients. However, the numbers of potential neo-epitopes can be vast, and it is impractical to immunize patients with such vast numbers of peptides. The combination of the NetMHC algorithm with the DAI and the C-terminal stability algorithms, as identified here, now makes it possible to reduce the large numbers of potential neo-epitopes to a much smaller number of truly immunogenic epitopes, which can now be used to immunize patients in a realistic manner.

In an embodiment, a method of identifying immunologically protective neo-epitopes in a cancer patient comprises
  providing a putative neo-epitope set,
  determining the conformational stability of at least a portion of each putative neo-epitope in the putative neo-epitope set bound to an MHC I or MHC II protein,
  selecting from the putative neo-epitope set the immunologically protective neo-epitopes, wherein the immunologically protective neo-epitopes have higher conformational stability compared to the corresponding wild type epitopes when bound to the MHC I or MHC II protein,
  optionally producing a pharmaceutical composition comprising a pharmaceutically acceptable carrier and one or more immunologically protective neo-epitope peptides, one or more polypeptides containing the immunologically protective neo-epitopes, or one or more polynucleotides encoding the one or more immunologically protective neo-epitopes, and
  optionally administering the pharmaceutical composition to the cancer patient.

The putative neo-epitope set can be identified using the DAI as described herein, or can be determined using the NetMHC scores, a peptide-MHC protein on-rate, a peptide-MHC protein off-rate, peptide solubility and/or other physical and/or chemical properties of the peptides.

T cell immune responses are dependent upon T cell receptor (TCR) recognition of a peptide presented by a class I or class II MHC protein. As used herein, an MHC protein is one or more polypeptides that make up the MHC heavy chain and $\beta$2-microglobulin for class I MHC, or the polypeptides that make up the $\alpha$ and $\beta$ chain for class II MHC, or an active fragment thereof. As explained herein, the conformational stability of an epitope in a MHC peptide-binding groove can be used to help predict immunogenicity.

For a peptide in a class I or class II MHC binding groove, the conformation is the structure the peptide adopts within the groove, as commonly although not exclusively determined via X-ray crystallography or examined by computational modeling (see, for example pmid 17719062). Stability is defined as the extent to which the conformation fluctuates (or moves) around this conformation, which can be measured or estimated using thermodynamic, spectroscopic, computational, crystallographic, or hydrogen exchange techniques. Stability can also include entropy as well as other dynamic processes. Thermodynamic techniques include, but are not limited to, measurements of peptide binding entropy changes by calorimetry, van't Hoff analyses, or Eyring analyses (see, for example, pmid 12718537). Spectroscopic techniques include, but are not limited to, examination of peptide motion by nuclear magnetic resonance, fluorescence, or infra-red spectroscopy (see, for example, pmid 19772349). Computational techniques include, but are not limited to, molecular dynamics simulations or Monte Carlo sampling (see, for example, pmid 21937447). Crystallographic techniques include, but are not limited to, comparison of multiple X-ray structures of the same peptide-MHC complex, examination of electron density, examination of crystallographic temperature factors, or examination of alternate peptide conformations present in one X-ray structure (see, for example, pmid 17719062). Hydrogen exchange techniques include, but are not limited to, measurements of the rates of hydrogen exchange or the extent of exchange at a given time point by NMR or mass spectrometry.

As used herein, the term conformational fluctuations refers to either amplitude or frequency of motion around a structure. Therefore, with higher conformational stability, an epitope has fewer fluctuations around a structure. An equivalent way of describing conformational fluctuations is that with higher conformational stability, there is less motion of the peptide. The term fluctuations can be used interchangeably with motion, entropy or other terms that describe dynamic motion in a peptide.

It is well established that conformational stability influences biomolecular recognition (pmid 20383153). Lower conformational stability results in higher entropy. If there is higher entropy at a recognition site (e.g., at a peptide in an MHC binding groove), this opposes biomolecular recognition as it increases the entropic penalty for binding. This principle has been demonstrated in T cell receptor recognition of peptide/MHC (pmid 20064447). Therefore, raising conformational stability is a means to strengthen T cell receptor binding to peptide/MHC (i.e., increase the magnitude of the T cell receptor binding equilibrium constant or lower the Gibbs free energy of binding). In many cases, stronger T cell receptor binding to peptide/MHC results in stronger immune responses (see for example pmid 10435578). Thus, the present inventors have discovered that increasing mutant peptide conformational stability compared to the wild type peptide improves immunogenicity of the putative epitope.

The amino acid sequence variability in peptides, T cell receptor (TCR) complementarity determining region loops, and MHC proteins means that TCRs bind peptide/MHC complexes with varying affinities, thermodynamics, and kinetics (pmid 18496839, 9597140). This in turn is because the contributions of the fundamental chemical and physical principles that govern biomolecular recognition (hydrogen bonds and other electrostatics, hydrophobicity, van der Waals interactions, and configurational entropy) will vary with TCR, peptide, and MHC chemical and structural properties. Therefore, the exact impact of a change conformational stability will differ with different neo-epitopes and epitope pairs. However, based on literature examples of the effects of conformational stability on biomolecular recognition, examples of meaningful reductions in conformational stability are:

For thermodynamic measurements, reduction of the entropy of peptide binding (ΔS°) by 3 cal/K/mol or more.

For crystallographic analyses, elimination of alternate conformations in a refined structure, elimination of electron density gaps in a $2F_o$-$F_c$ electron density map, or reductions of temperature factors for atoms of the peptide by 10% or more.

For measurements using nuclear magnetic resonance, increases in order parameters for atoms of the peptide by 10% or more.

For measurements using fluorescence anisotropy, increases in steady state anisotropy values for a fluorescently labeled or intrinsically fluorescent peptide of 20% or more or decreases in correlation times of 20% or more.

For computational analyses, decreases in the root mean square fluctuations of atoms of the peptide by 0.5 Å or more.

For analyses of hydrogen exchange by NMR or mass spectrometry, decreases in the rates of hydrogen exchange at individual amides or of amino acid fragments of 15% or more, or decreases in the extent of exchange at a particular time point of 15% or more.

Any one of the above measures of higher conformational stability can be used to determine that a mutant peptide has a higher conformational stability than the wild type peptide. The quantification of higher conformational stability for a neo-epitope compared to the wild-type sequence is thus dependent upon the technique used to determine the conformational stability. However, such techniques are well-known in the art and one of ordinary skill in the art could readily determine if the mutant epitope has higher conformational stability than a wild-type epitope using a specified technique.

Thus, in order to determine which neo-epitopes in the putative neo-epitope set have the highest probability of being immunogenic, the conformational stability of the putative neo-epitopes is compared to the corresponding wild-type epitope. The premise is that the greater the peptide conformational stability (or equivalently, the greater the rigidity), the higher the probability for productive interactions with TCRs. This premise is grounded in fundamental structural and biophysical principles that underlie biomolecular interactions (e.g., binding entropy changes and shape/chemical complementarity). Comparative assessments of conformational stability between wild type and neo-epitopes can thus be used to predict those neo-epitopes that are more likely to be productively engaged by TCRs and initiate immune responses. Conformational stability of a putative epitope set may be assessed experimentally via experimental techniques such as, but not limited to, calorimetry, NMR, fluorescence, IR spectroscopy, or mass spectrometry, or computationally via techniques such as, but not limited to, molecular dynamics simulations or Monte Carlo sampling.

Conformational stability may be determined for the entire epitope or specific regions (e.g., the peptide center, N- or C-terminus, etc.).

In a specific embodiment, once the putative neo-epitope set has been selected, the root mean squared fluctuations (RMSF) of at least a portion of each epitope in the putative neo-epitope set bound to an MHC I or MHC II protein are determined as a measure of the conformational stability of the peptides. The root mean squared fluctuations are determined for the C-terminal portion of the peptide, the central portion of the peptide, the N-terminal portion of the peptide, or the entire peptide. It was unexpectedly found that mutant peptides which fail to elicit an immunological response have a high instability, particularly C-terminal instability. In the studies presented herein, the average C-terminal RMSF was 0.9 Å, and peptides with a C-terminal RMSF below this value were immunogenic. In specific embodiments, it is preferred that root mean squared fluctuations of at least a portion of the α-carbons of each epitope in the putative neo-epitope set bound to an MHC I or MHC II protein is less than 2 Å, less than 1.5 Å less than 1.2 Å, or less than 0.9 Å. Thus, C-terminal stability is a predictor of immunogenicity. Immunologically protective neo-epitopes are selected from the putative epitope set as epitopes having a root mean squared fluctuation of less than 2 Å, less than 1.5 Å less than 1.2 Å, or less than 0.9 Å.

In one aspect, the MHC protein is an MHC I protein and the immune response is a CD8+ response. Exemplary MHC I proteins include the mouse H-2k$^d$, H-2k$^b$ and H-2D$^d$ peptides and the human HLA protein, such as HLA-A, HLA-B and HLA-C, specifically HLA-A*0201. Thus, in one aspect, the method further comprises assaying the CD8 T-cell response of the neo-epitopes.

In another aspect, the MHC peptide is an MHC II protein, and the response is a CD4+ response. Exemplary MHC II proteins include HLA-DR, HLA-DP, HLA-DQ. Thus, in one aspect the method further comprises assaying the CD4 T-cell response of the neo-epitopes.

In yet another aspect, the immunologically protective neo-epitopes have a measured IC50 for H-2K$^d$ or HLA of greater than 100 nM or greater than 500 nM.

In one embodiment, the putative neo-epitope set is determined using the DAI determined by the following method:

sequencing at least a portion of the cancer patient's RNA or DNA in both a healthy tissue and a cancer tissue, to produce a healthy tissue RNA or DNA sequence and a cancer tissue RNA or DNA sequence, comparing the healthy tissue RNA or DNA sequence and the cancer tissue RNA or DNA sequence and identifying differences between the healthy tissue RNA or DNA sequence and the cancer tissue RNA or DNA sequence to produce a difference DNA marker set, analyzing the difference DNA marker set to produce a tumor-specific epitope set, wherein the tumor-specific epitope set comprises one or more tumor-specific epitopes, providing a numerical score called the Differential Agretopic Index for each epitope in the tumor-specific epitope set, wherein the Differential Agretopic Index is calculated by subtracting a score for a normal epitope from a score for the tumor-specific epitope, and ranking the tumor-specific epitope set according to the Differential Agretopic Index and selecting a putative neo-epitope set from the tumor-specific epitope set based on the ranking.

In the method described herein the tumor-specific epitope set is ranked according to the Differential Agretopic Index and a putative neo-epitope set is selected from the tumor-specific epitope set based on the ranking. In one aspect, the top 50%, 40%, 30%, 20% or 10% of epitopes is selected.

The pharmaceutical compositions optionally further comprise an adjuvant or immune-modulating agent.

In one embodiment, sequencing at least a portion of the cancer patient's RNA or DNA in both a healthy tissue and a cancer tissue comprises transcriptome sequencing, genome sequencing, or exome sequencing. Transcriptome sequencing is sequencing the messenger RNA or transcripts from a cell. The transcriptome is the small percentage of the genome (less than 5% in humans) that is transcribed into RNA. Genome sequencing is sequencing the complete DNA sequence of an organism's genome. Exome sequencing is sequencing the protein-encoding parts of the genome. In a specific embodiment, sequencing is transcriptome sequencing, which allows for identification of the mutations that are expressed in tumors.

In another aspect, the depth of sequencing can be varied. In next-generation sequencing, overlapping fragments of the DNA sample of interest are produced and sequenced. The overlapping sequences are then aligned to produce the full set of aligned sequence reads. Depth of sequencing, also called coverage of sequencing, refers to the number of nucleotides contributing to a portion of an assembly. On a genome basis, sequencing depth refers to the number of times each base has been sequenced. For example, a genome sequenced to 30× means that each base in the sequence was covered by 30 sequencing reads. On a nucleotide basis, depth of sequencing refers to the number of sequences that added information about a single nucleotide.

In one aspect RNA or DNA is isolated from tumor and healthy tissue by isolating polyA+ RNA from each tissue, preparing cDNA and sequencing the cDNA using standard primers. Such techniques are well-known in the art. Also, sequencing of all or a portion of a patient's genome is well-known in the art. High-throughput DNA sequencing methods are known in the art and include, for example, the HiSeq™2000 system by Illumina® Sequencing Technology, which uses a large parallel sequencing-by-synthesis approach to generate billions of bases of high-quality DNA sequence per run.

In certain embodiments, particular portions of the cancer patient's genome are sequenced, depending on the tumor, for example. In most cases, sequencing the entire genome/transcriptome is preferred; the genome may be sequenced to a shallow depth or a deep depth, allowing coverage or less or more portions of the genome/transcriptome.

In a specific embodiment, analyzing the difference DNA or RNA marker set to produce a tumor-specific epitope set comprises using a predictive algorithm that determines the binding of epitope peptides to MHC molecules. Optionally, the tumor-specific epitope set is refined to provide an MHC-restricted tumor-specific epitope set. For example, MHC I-restricted epitopes of the K, D or L alleles can be provided. MHC-restricted epitope sets can be produced by determining binding of a peptide containing the epitope to an MHC-allele-specific protein. One example of such an algorithm is NetMHC-3.2 which predicts the binding of peptides to a number of different HLA alleles using artificial neural networks (ANNs) and weight matrices.

Specifically, the DNA (or RNA) sequence differences between the healthy and cancer tissues, in combination with a mammal's MHC composition, are analyzed by an epitope predictive algorithm such as NetMHC. This algorithm produces a list of potential tumor-specific epitopes for this individual mammal and gives each epitope a numerical score. In the current state of the art, a high score implies a good probability of the epitope being able to immunize, and a low (including a negative) score implies a poor probability of the epitope being able to immunize.

The method further comprises providing a numerical score for each epitope in the tumor-specific epitope set or the MHC-restricted tumor-specific epitope set, wherein the numerical score is calculated by subtracting a score for the normal epitope (non-mutated) from a score for the tumor-specific epitope (mutated). The numerical score for the normal epitope is subtracted from the numerical score for the mutant cancer epitope, and a numerical value for the difference is obtained—the Differential Agretopic Index (DAI) for the epitope. The putative epitopes can be ranked on basis of the DAI. In this ranking, broadly speaking, the higher the difference for a given epitope, the higher the probability that immunization with it shall be protective against the tumor. In a specific embodiment, the highest ranked epitopes are used to immunize an individual. Further, the method can comprise ranking the tumor specific-epitope set or the MHC-restricted tumor-specific epitope set by the Differential Agretopic Index for each epitope in the set. In one aspect, the method further comprises using the ranking by Differential Agretopic Index (DAI) to identify a subset of 10 to 50 top-ranked tumor specific-epitopes. Top-ranked means the epitopes with the most favorable DAI.

As an example, if the mutated DNA in the cancer, at a given site, codes for an amino acid sequence of GYSVLHLAII (SEQ ID NO. 4), and the corresponding non-mutated sequence in the normal tissue is GDSVLHLAII (SEQ ID NO: 5). The predictive algorithm (NetMHC in this case) gives a numerical score of +7.3 for the cancer sequence and a score of −4.3 for the normal sequence. The DAI is 11.6. This DAI is used to rank this epitope.

In the current state of art, the numerical score of a mutated epitope given by the predictive algorithm such as NetMHC is the major or sole guide for immunization; the higher the score given by such traditional algorithm, the better a peptide is expected to be. In our analysis, this is not a good method of prediction for tumor-protection. Advantageously, by the methods disclosed herein, (a) the traditional algorithms (like NetMHC) for predicting the score for the non-mutated counterpart, and (b) the difference between the mutated and non-mutated epitope, are used as the guide to predict the anti-tumor immunogenicity of a peptide epitope.

In a specific embodiment, analyzing the difference DNA marker set to produce a tumor-specific epitope set is independent of whether one or more tumor-specific epitopes are related to cancer-causing pathways. Prior methods for analyzing the DNA of cancer patients focused on the genetic mechanisms that cause cancer or that drive cancer, while the present approach is agnostic about that issue. The approach described herein is aimed to attack cancer at any point where it is different from the normal, regardless of whether that difference is responsible for causing cancer or not. A major consequence of this difference is that the other approaches rely mostly on deciding which existing (or future) medicines to use for each patient, and not on designing a medicine for each patient. The present method focuses on designing a medicine to treat a particular tumor.

An advantage of the method described herein is the focus on the differences in the DNA sequences that are specific to cancer. In contrast, with a small number of notable exceptions (ras, p53, bcr-abl translocations, etc.), most of the genetic mechanisms that cause cancer are not truly cancer-specific; instead, normal cells under some normal circumstances also use them. Thus, they are cancer-selective, preferably binding cancer cells over normal cells, but are not cancer-specific, binding both cancer cells and normal cells. The approach described herein is focused on epitopes that are cancer-specific. A distinct benefit of using cancer-specific rather than cancer-selective markers is reduced toxicity of the vaccines that are produced. Further advantages include using immune therapy as opposed to drug therapy which allows for the creation of vaccines having specificity for the actual cancer in the patient.

Identifying differences between the healthy tissue RNA or DNA sequence and a cancer tissue RNA or DNA sequence to produce a difference DNA marker set can be done using bioinformatics technologies known in the art. In one embodiment, the initial screen includes all identifiable changes in the cancer patient's genome. Changes include both synonymous changes (which do not change the encoded amino acid) and non-synonymous changes (which change the encoded amino acid). As explained in the examples, immunoediting results in a reduction in the number of non-synonymous mutations compared to the predicted percentage. In one aspect, a change in a DNA marker is a single nucleotide variant (SNV).

As used herein, a tumor epitope or tumor antigen is a peptide antigen that is produced in tumor cells. Many tumor antigens have been identified in humans as well as mice, for example, various abnormal products of ras and p53 are found in a variety of tumors. In addition to the tumor antigens that are commonly found in different types of tumors, the present inventors have recognized that, depending on the tumor size and the degree of genetic instability, human tumors can have tens to hundreds of truly tumor-specific epitopes. As used herein, a tumor-specific epitope is an epitope that is specific for a particular tumor and is not generally recognized as a tumor antigen.

Also included herein are isolated immunologically protective neo-epitope peptides identified by the methods disclosed herein. An "isolated" or "purified" peptide is substantially free of cellular material or other contaminating polypeptide from the cell or tissue source from which the protein is derived, or substantially free of chemical precursors or other chemicals when chemically synthesized. The language "substantially free of cellular material" includes preparations of polypeptide in which the polypeptide is separated from cellular components of the cells from which it is isolated or recombinantly produced. Immunologically protective neo-epitope peptides generally have lengths of 7 to 25 amino acids, specifically 8 to 15 amino acids, and more specifically 8 to 10 amino acids.

The individual peptides identified as immunologically protective neo-epitopes can be tested for immunogenicity using methods known in the art.

In one embodiment, a peptide corresponding to each immunologically protective neo-epitope is employed. In another embodiment, a polypeptide containing two or more immunologically protective neo-epitopes is employed. One polypeptide containing multiple immunologically protective neo-epitopes optionally separated by non-epitope linkers can be employed. Such polypeptides can be readily designed by one of ordinary skill in the art.

In certain embodiment, instead of immunologically protective neo-epitope peptides, a pharmaceutical composition comprises one or more polynucleotides encoding the peptides. The peptides can all be expressed from the same polynucleotide molecule, or from multiple polynucleotide molecules.

In one aspect, the neo-epitope peptides contain at least one substitution modification relative to the neo-epitope or one or more nucleotides at the 5'3 or 3' end of the peptide that is not found in the neo-epitope. In another aspect, a detectable label is attached to the neo-epitope.

"Polynucleotide" or "nucleic acid sequence" refers to a polymeric form of nucleotides at least 5 bases in length. The nucleotides can be ribonucleotides, deoxyribonucleotides, or modified forms of either nucleotide. Polynucleotides can be inserted into a recombinant expression vector or vectors. The term "recombinant expression vector" refers to a plasmid, virus, or other means known in the art that has been manipulated by insertion or incorporation of the peptide genetic sequence. The term "plasmids" generally is designated herein by a lower case "p" preceded and/or followed by capital letters and/or numbers, in accordance with standard naming conventions that are familiar to those of skill in the art. Plasmids disclosed herein are either commercially available, publicly available on an unrestricted basis, or can be constructed from available plasmids by routine application of well-known, published procedures. Many plasmids and other cloning and expression vectors are well known and readily available, or those of ordinary skill in the art may readily construct any number of other plasmids suitable for use. These vectors may be transformed into a suitable host cell to form a host cell vector system for the production of a polypeptide.

The peptide-encoding polynucleotides can be inserted into a vector adapted for expression in a bacterial, yeast, insect, amphibian, or mammalian cell that further comprises the regulatory elements necessary for expression of the nucleic acid molecule in the bacterial, yeast, insect, amphibian, or mammalian cell operatively linked to the nucleic acid molecule encoding the peptides. "Operatively linked" refers to a juxtaposition wherein the components so described are in a relationship permitting them to function in their intended manner. An expression control sequence operatively linked to a coding sequence is ligated such that expression of the coding sequence is achieved under conditions compatible with the expression control sequences. As used herein, the term "expression control sequences" refers to nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcription terminators, a start codon (i.e., ATG) in front of a protein-encoding gene, splicing signals for introns (if introns are present), maintenance of the correct reading frame of that gene to permit proper translation of the mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter. By "promoter" is meant minimal sequence sufficient to direct transcription. Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters are included.

A pharmaceutical composition (e.g., a vaccine) comprises at least one isolated immunologically protective neo-epitope peptide (or RNA or DNA encoding such epitope peptides) and a pharmaceutically acceptable carrier. Pharmaceutically acceptable excipients include, for example, diluents, preservatives, solubilizers, emulsifiers, and adjuvants. As used herein "pharmaceutically acceptable excipients" are well known to those skilled in the art. In one embodiment, a pharmaceutical composition allows for local delivery of the active ingredient, e.g., delivery directly to the location of a tumor.

In specific embodiment, a pharmaceutical composition comprises 1 to 100 immunologically protective neo-epitope peptides, specifically 3 to 20 immunologically protective neo-epitope peptides. In another embodiment, a pharmaceutical composition comprises a polypeptide containing 1 to 100 immunologically protective neo-epitopes, specifically 3 to 20 immunologically protective neo-epitopes. In another aspect, a pharmaceutical composition comprises a polynucleotide encoding 1 to 100 immunologically protective neo-epitopes, specifically 3 to 20 tumor-specific immunologically protective neo-epitopes.

In one embodiment, pharmaceutical compositions suitable for intravenous, intramuscular, subcutaneous, intradermal, nasal, oral, rectal, vaginal, or intraperitoneal administration conveniently comprise sterile aqueous solutions of the active ingredient with solutions which are preferably isotonic with the blood of the recipient. Such formulations can be conveniently prepared by dissolving the peptide in water containing physiologically compatible substances, such as sodium chloride (e.g., 0.1-2.0 M), glycine, and the like, and having a buffered pH compatible with physiological conditions to produce an aqueous solution, and rendering said solution sterile. These can be present in unit or multi-dose containers, for example, sealed ampoules or vials.

Additional pharmaceutical methods can be employed to control the duration of action. Controlled release preparations can be achieved through the use of polymer to complex or absorb the peptides or nucleic acids. The controlled delivery can be exercised by selecting appropriate macromolecules (for example polyester, polyamino acids, polyvinyl, pyrrolidone, ethylenevinylacetate, methylcellulose, carboxymethylcellulose, or protamine sulfate) and the concentration of macromolecules as well as the methods of incorporation in order to control release. Another possible method to control the duration of action by controlled-release preparations is to incorporate a protein, peptides and analogs thereof into particles of a polymeric material, such as polyesters, polyamino acids, hydrogels, polylactic acid) or ethylene vinylacetate copolymers. Alternatively, instead of incorporating these agents into polymeric particles, it is possible to entrap these materials in microcapsules prepared, for example, by coacervation techniques or by interfacial polymerization, for example, hydroxy-methylcellulose or gelatin-microcapsules and poly(methylmethacylate) microcapsules, respectively, or in colloidal drug delivery systems, for example, liposomes, albumin microspheres, microemulsions, nanoparticles, and nanocapsules or in macroemulsions.

Local administration to the afflicted site can be accomplished through means known in the art, including, but not limited to, topical application, injection, and implantation of a porous device containing cells recombinantly expressing the peptides, implantation of a porous device in which the peptides are contained.

In one embodiment, the immunologically protective neo-epitope peptides or polynucleotides are mixed with the cells of the cancer patient, for example, by mixing or pulsing, and then administering the mixed or pulsed cells to the cancer patient.

In one embodiment, a vaccine composition further comprises an immune-modulating agent. Exemplary immune-modulating agents include TLR ligands such, for example, CpG oligonucleotide DNA (a TLR9 ligand), lipopeptides and lipoproteins (TLR1 and TLR2 ligands), poly I:C and double stranded RNA (TLR3 ligands), lipopolysaccharide (TLR4 ligand), diacyl lipopeptide (TLR6 ligands), imiquimod (a TLR7 ligand), and combinations of TLR ligands. Another exemplary immune-modulating agent is an antibody such as anti-cytotoxic T-lymphocyte antigen-4 antibody (anti-CTLA-4), or an antibody blocking Programmed Death 1 (PD1) or a PD1 ligand.

Combinations of immune-modulating agents are also contemplated. Examples are: combination of the vaccine with a TLR ligand and anti-CTLA4 antibody, or with CpG and an antibody blocking PD1.

The immunogenic composition optionally comprises an adjuvant. Adjuvants in general comprise substances that boost the immune response of the host in a non-specific manner. Selection of an adjuvant depends on the subject to be vaccinated. Preferably, a pharmaceutically acceptable adjuvant is used. For example, a vaccine for a human should avoid oil or hydrocarbon emulsion adjuvants, including complete and incomplete Freund's adjuvant. One example of an adjuvant suitable for use with humans is alum (alumina gel).

In one embodiment a pharmaceutical composition comprises one or more immunologically protective neo-epitope peptides, one or more polypeptides containing the immunologically protective neo-epitopes, or one or more polynucleotides encoding the one or more immunologically protective neo-epitopes, and a pharmaceutically acceptable carrier, wherein the putative neo-epitope set does not include epitopes from known cancer-causing pathways, wherein the putative neo-epitope set is specific to a tumor from a cancer patient, and wherein the conformational stability of each immunologically protective neo-epitope bound to an MHC I or MHC II protein as determined by computation or experiment are higher compared to each corresponding wild type epitope.

As used herein, a patient is a mammal, such as a mouse or a human, specifically a human patient.

The compositions and methods described herein are applicable to all cancers including solid tumor cancers, e.g., those of the breast, prostate, ovaries, lungs and brain, and liquid cancers such as leukemias and lymphomas.

The methods described herein can be further combined with additional cancer therapies such as radiation therapy, chemotherapy, surgery, and combinations thereof.

The invention is further illustrated by the following non-limiting examples.

Examples

Materials and Methods

Mice and tumors. The BALB/cJ mice (6-8-week-old females) were purchased from the Jackson Laboratory (Bar Harbor, ME). Mice were maintained in the virus-free mouse facilities at the University of Connecticut Health Center.

Sample Preparation. Samples were prepared using the Illumina® protocol outlined in "Preparing Samples for Sequencing of mRNA" (Part #1004898 Rev. A September 2008). The protocol consists of two parts: cDNA synthesis and paired-end library preparation. First, mRNA was purified from total RNA using magnetic oligo(dT) beads, then fragmented using divalent cations under elevated temperature. cDNA was synthesized from the fragmented mRNA using Superscript™ II (Invitrogen), followed by $2^{nd}$ strand synthesis. cDNA fragment ends were repaired and phosphorylated using Klenow, T4 DNA Polymerase and T4 Polynucleotide Kinase. Next, an 'A' base was added to the 3' end of the blunted fragments, followed by ligation of Illumina® Paired-End adapters via T-A mediated ligation. The ligated products were size selected by gel purification and then PCR amplified using Illumina® Paired-End primers. The library size and concentration were determined using an Agilent Bioanalyzer.

GAII run conditions. The RNA-seq library was seeded onto the flowcell at 8 pM, yielding approximately 282K to 384K clusters per tile. The library was sequenced using 61 cycles of chemistry and imaging.

Analysis of sequencing data. Initial data processing and base calling, including extraction of cluster intensities, was done using RTA (SCS version 2.6 and SCS version 2.61). Sequence quality filtering script was executed in the Illumina® CASAVA software (ver 1.6.0, Illumina®, Hayward, CA).

Figure 2:
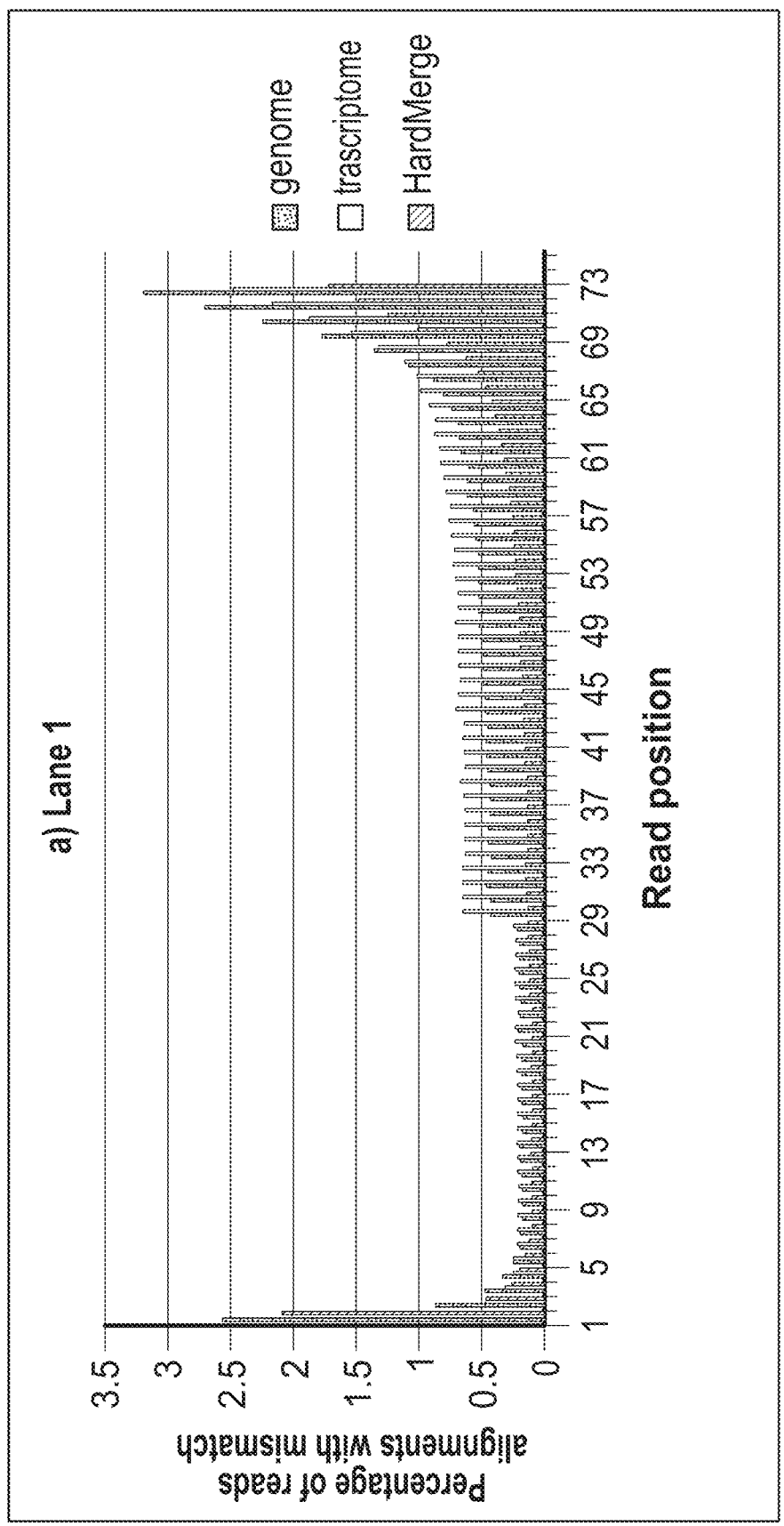
FIG. 2 shows a read position mismatch analysis for the three Meth A RNA-Seq lanes. After mapping reads to the BALB/c genome and transcriptome, the number of mismatches is counted at each read position across all alignments. The statistics are collected for alignments resulting from HardMerge. a-c: mismatch statistics for Meth A sequencing lanes 1-3; right histograms: genome alignments, middle: transcriptome, and left: HardMerge. High mismatch rates at the ends of the reads are caused by systematic errors introduced during library preparation and sequencing. The high mismatch rate at 5' end of reads is likely the result of using random hexamers to prime cDNA synthesis in library preparation, while the increasing mismatch rate towards the 3' end is caused by diminishing signal-to-noise ratio due to de-phasing effects in sequencing-by-synthesis of clonally amplified template molecules. The increase in mismatch rate at position 29 results from using a seed length of 28 bases for read mapping and upper-bounding the number of mismatches in the seed. Similar mismatch patterns were observed for the CMS5. Clipping first two and last ten bases from each aligned read results in a mismatch rate of <1% across all bases for HardMerge alignments.
Figure 2:
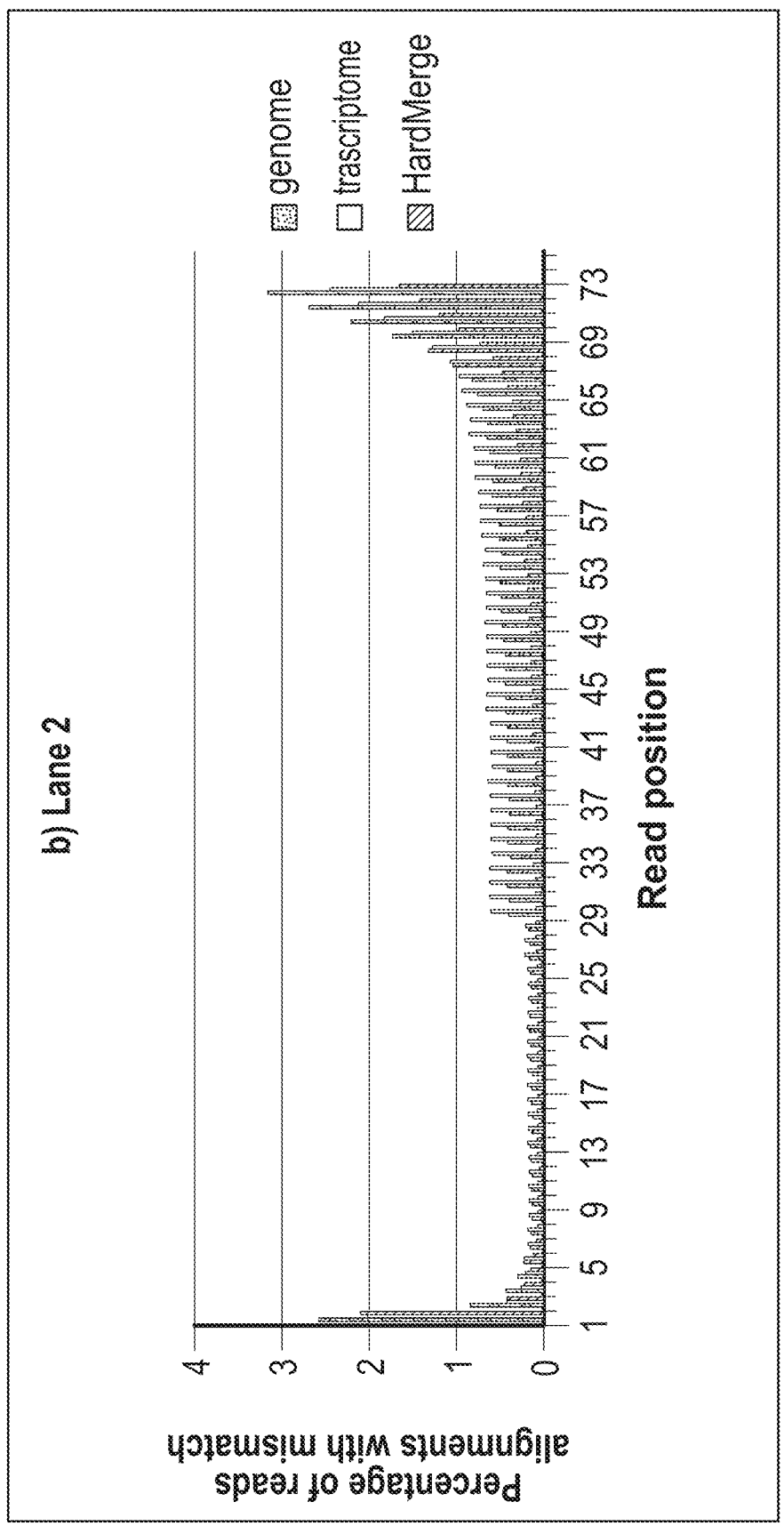
Figure 2:
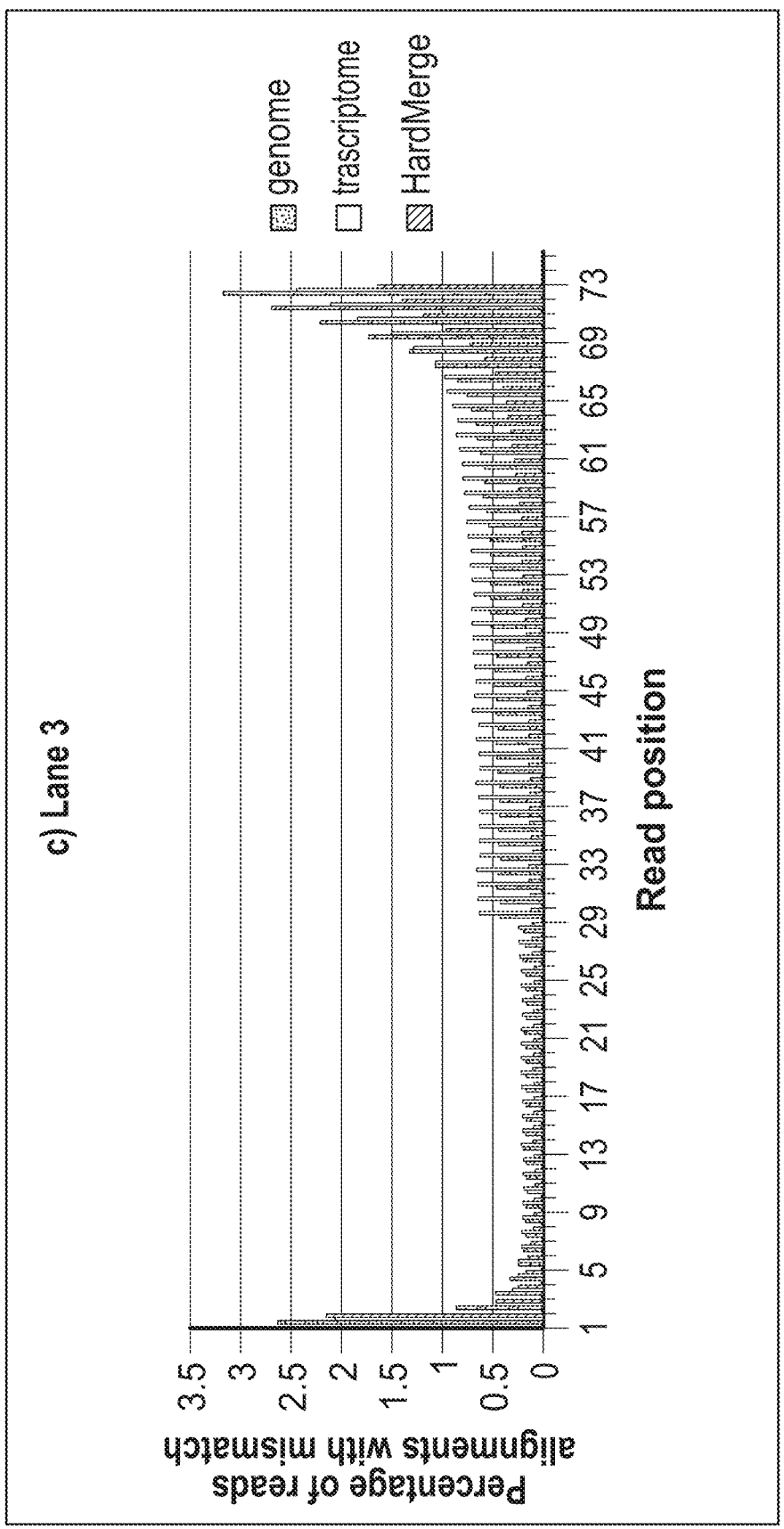

Epi-Seq Bio-informatics pipeline. A high-level representation of the bioinformatics pipeline used for identifying tumor specific epitopes from high throughput mRNA sequencing data (RNA-Seq) is given in FIG. 1. The pipeline starts by mapping RNA-Seq reads against the strain-specific genome sequences downloaded from the Sanger Mouse Genomes Project and a strain-specific haploid transcript library derived from CCDS annotations. BALB/c genome/transcriptome sequences for CMS5 and Meth A cell lines were used. DatabaseSNP polymorphisms were removed. Instead of comparing to the mm9 reference genome, then excluding SNPs in dbSNP, we created a strain specific genome by applying strain SNVs to the mm9 reference genome. The SNVs were downloaded from the Mouse Genomes. The created genome was used to map the reads and call the mutations. Reads were mapped using Bowtie with the default seed length of 28, maximum of 2 mismatches in the seed, and maximum sum of phred quality scores at mismatch positions of 125. Following an initial round of mapping, mismatch statistics were calculated for each read position and each sample (FIG. 2 for the Meth A sample). Based on this analysis, 2 bases from the 5' end and 10 bases from the 3' end were clipped from all aligned reads. The resulting read alignments were merged using the HardMerge algorithm. HardMerge discards reads that align to multiple locations in the genome and/or transcriptome, as well as reads that align uniquely to both, but at discordant locations. To reduce the effect of bias introduced by PCR amplification during library preparation, multiple reads were replaced with alignments starting at the same genomic location with their consensus. The SNVQ algorithm was then used to call single nucleotide variants (SNVs) from the filtered set of aligned reads. SNVQ uses Bayes' rule to call the genotype with the highest probability while taking base quality scores into account. High confidence SNVs were selected by requiring a minimum phred quality score of 50 for each called genotype, a minimum of 3 reads supporting the alternative allele, with at least one read mapping on each strand. Haplotype inference over called SNV genotypes was performed using the RefHap Single Individual Haplotyping algorithm that uses read evidence to phase blocks of proximal SNVs. Since residual heterozygosity in the inbred mice used in these experiments is predicted to be low, unique heterozygous SNVs were considered to be novel somatic mutations. Homozygous SNVs as well as heterozygous SNVs shared by more than one tumor with the same genome background were assumed to be germ-line mutations and were not used for epitope prediction unless located near a unique heterozygous SNV. For each unique heterozygous SNV, reference and alternative peptide sequences were generated based on the two inferred haplotypes for each CCDS transcript. Generated amino acid sequences were then run through the NetMHC 3.0 epitope prediction program and scored using the Profile Weight Matrix (PWM) algorithm with default detection thresholds.

Binding assays. Binding of peptides to H-2 $K^d$ was determined using quantitative assays based on the inhibition of binding of a radiolabeled standard peptide to purified MHC molecules essentially as described previously. Peptides were typically tested at six different concentrations covering a 100,000-fold dose range, and in three or more independent assays. Under the conditions utilized, where [label]<[MHC] and $IC_{50}$≥[MHC], the measured IC50 values are reasonable approximations of the dissociation constant values.

Intracellular IFN-γ assay by FACS and ELISPOT. Lymphocytes were incubated either with or without 1-10 μg/ml peptide. GolgiPlug™ (BD Biosciences, San Jose, CA) was added 1 h later. After incubation of 12 to 16 h, cells were stained for CD44 (clone IM7), CD4 (clone GK1.5) and CD8 (clone 53-6.7) (BD Biosciences, San Jose, CA), fixed and permeabilized using the Cytofix/Cytoperm™ kit (BD Biosciences, San Jose, CA), and stained for intracellular IFN-γ using Phycoerythrin-conjugated anti-mouse IFN-γ (clone XMG1.2, BD Biosciences, San Jose, CA). Cells were stained with 1 μl antibody/million cells in 50 μl staining buffer (PBS with 1% bovine serum albumin) and incubated for 20 min at 4° C. in the dark, or according to the manufacturer's instructions. Cells without peptide stimulation were used as a negative control, and the values for these controls was very close to the values seen with the negative control peptide. Typically, 95,000-129,000 lymphocytes (14,500-17,000 CD8+CD4– cells) were acquired. The background is consistently very low (10% of the signal).

For the ELISPOT assays, the negative controls were CD8+ cells from immunized mice without peptide stimulation. The peptides were considered to be positive or immunogenic when spots from peptide-stimulated wells are significantly higher by Mann-Whitney test, compared to wells without cognate peptide stimulation. The magnitude of responses was rated by mean spot numbers per million CD8+ cells: 5-10 (+); 11-20 (++); 21-50 (+++); 51-100 (++++) and >100 (+++++).

Tumor challenge and representation of tumor growth. AUC as a tool to measure tumor growth has been described previously. Briefly, AUC was calculated by selecting "Curves & Regression" and then "Area under curve" from the "analyze" tool, using the Prism 5.0 (GraphPad Software, Inc., La Jolla, CA). Grubb' test was used to remove up to one outlier from each group.

Depletion of T cell subsets. Immunized mice were depleted of CD8 cells using anti-CD8 rat IgG2b monoclonal antibody 2.43) or depleted of CD4 cells using anti-CD4 rat IgG2b monoclonal antibody GK1.5. Depleting antibodies were given in PBS intraperitoneally two days before tumor challenge and every seven days for the duration of the experiment. First three injections of depleting antibodies were 250 μg per mouse and the later injections were 500 μg per mouse. For treatment with antagonistic antibodies, mice were treated with anti-CD25 antibody (clone PC61, 250 μg, two days before tumor challenge) or anti-CTLA-4 antibody (clone 9D9, 100 μg, seven days before and every three days after tumor challenge). The appropriate T cell sub-sets were depleted by over 95%.

Modeling of peptide/H-2$K^d$ complexes. Models of peptide/H-2$K^d$ complexes were built by adapting a previous method by Collins and colleagues used to identify immunogenic epitopes. Although developed on HLA-A*0201, the approach is generally applicable to class I MHC proteins in general, taking advantage of common class I MHC structural features.

An initial model of each complex was generated by MODELLER and the 'build mutants' functionality implemented in Accelrys Discovery Studio. The protocol uses a heavy-atom representation of the protein and includes homology-derived restraints combined with energy minimization and molecular dynamics/simulated annealing. The structure of the Flu peptide bound to H-2$K^d$ was used as a template. Atoms within 4.5 Å of each altered residue were allowed to repack during the modeling. For each pMHC, one hundred initial models were generated, and the lowest energy model from this first set was subjected to a more exhaustive, second phase of fully atomistic simulated annealing and molecular dynamics. For the second phase, after adding hydrogens, the structure was heated to 1500 K over 200 ps of simulation followed by cooling to 300 K over 800 ps. The annealed structure was then subjected to five independent 10 ns molecular dynamics runs at 300 K, each time beginning with the structure that resulted from the second phase annealing step.

Figure 4:
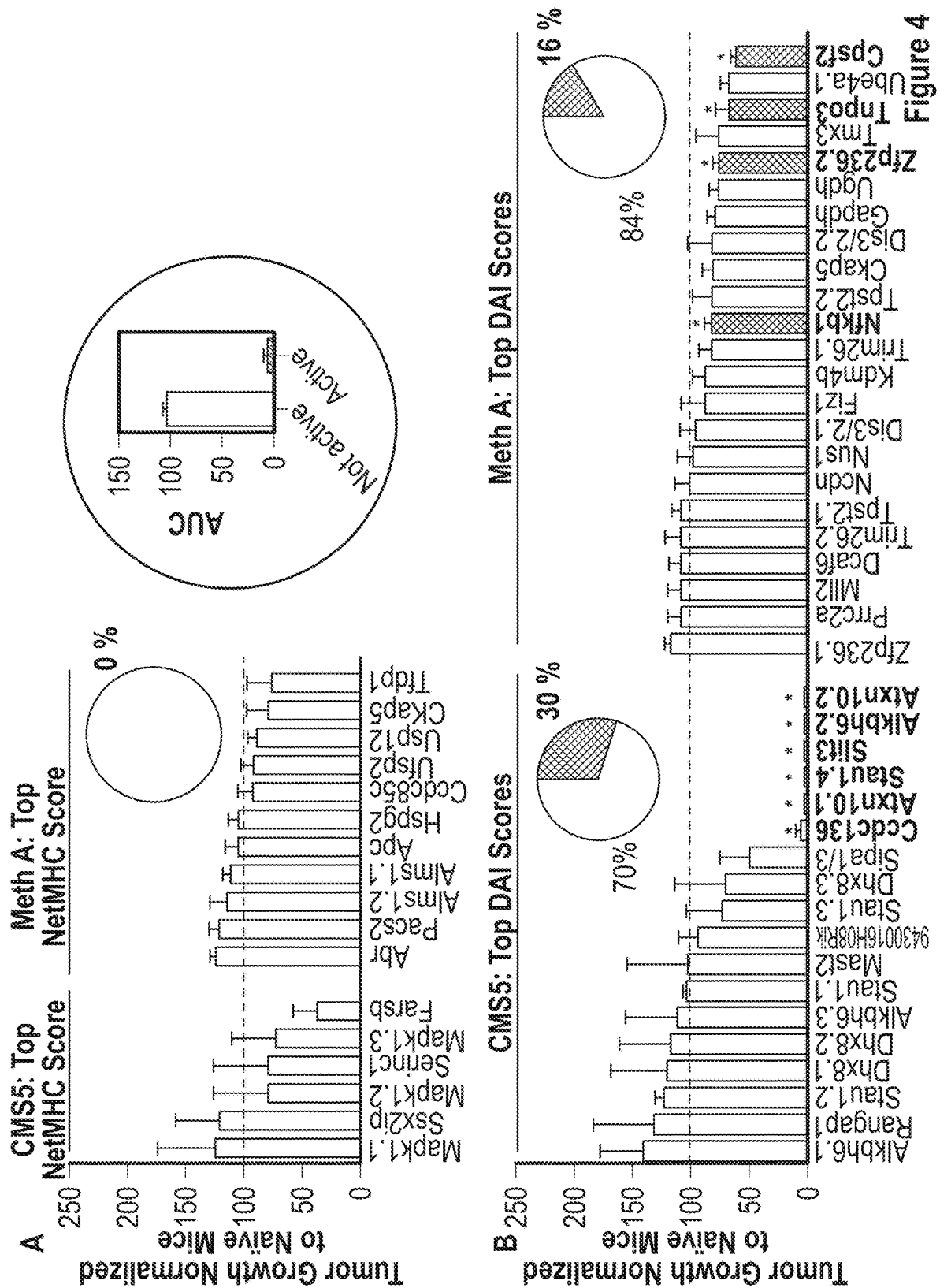
FIG. 4 shows the landscape of protective tumor immunity elicited by tumor-specific peptides. (A) Tumor-protective activity of the mutated epitopes with top DAI scores for CMS5 and Meth A. Mice were immunized with indicated peptides, challenged with live tumor cells, and tumor growth monitored as described in Experimental Procedures. Area under the curve (AUC) for each individual tumor growth curve was calculated and normalized by setting the naïve group to a value of 100, shown by a horizontal line. Bars corresponding to peptides that show statistically significant tumor-protective immunogenicity are filled and indicated by an asterisk (p value between 0.015 and 0.03). (One of the CMS5 neo-epitopes FarsB shows significant protection from tumor growth in this panel; however, this result could not be reproduced un-ambiguously, leading us to assign this as a negative neo-epitope with respect to protection from tumor growth.) The peptides are arranged in order of decreasing activity and not in order of their ranking by DAI scores. See Table 3 for the ranking of peptides by DAI. The pie charts show the percentage of neo-epitopes tested that did not (black) and did (gray) elicit protection from tumor challenge. (B) Examples of tumor growth curves in untreated mice (naïve) and mice immunized with indicated mutant peptides from CMS5. Stau1.2 is a representative neo-epitope that does not elicit protective immunity, while Atxn10.1 and Alkbh6.2 are representative neo-epitopes that do. For Atxn10.1 and Alkbh6.2, the results of immunization with the neo-epitopes as well as the WT counterparts are shown. Each line shows the kinetics of tumor growth in a single mouse. The experiments were carried out three times.
Figure 4:
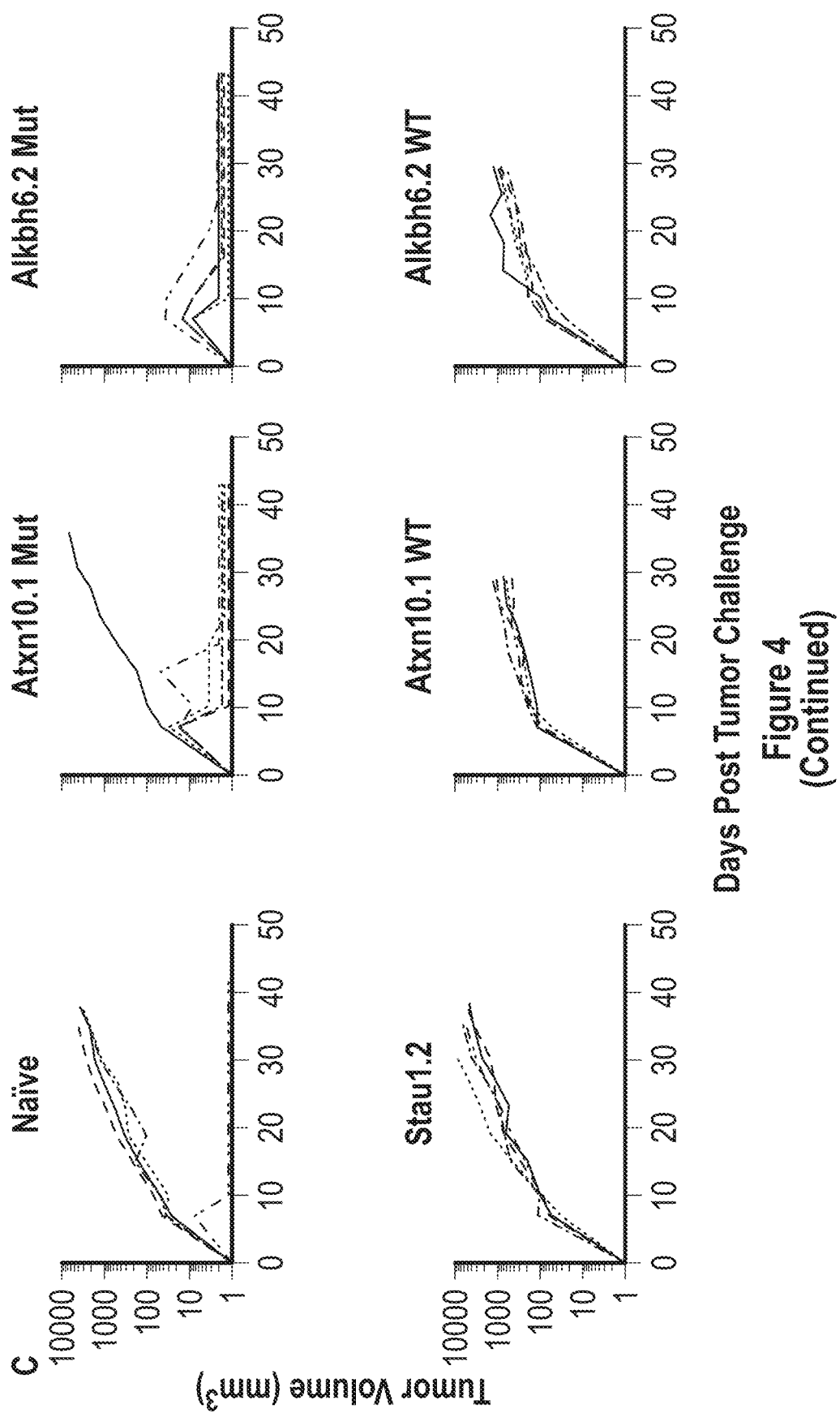

All second phase dynamics calculations were performed using AMBER 12 running on Nvidia GPU accelerators. The ff99SB force field was used with a 2 fs time step. Solvent was treated implicitly using the generalized Born model to accelerate sampling. The SHAKE algorithm was used to constrain all bonds to hydrogens. A 20 kcal/mol harmonic restraint was applied to the $\alpha 1$ and $\alpha 2$ helices (residues 56-85 and 138-175). Two additional 20 kcal/mol distance restraints were applied to hydrogen bonds at the N- and C-terminal ends of the peptide. The first was between the P1 backbone oxygen and the hydroxyl of Tyr 159 of H-2$K^d$. The second was between the P8 backbone oxygen and the ring nitrogen of Trp 147 of H-2$K^d$. As a positive control, the simulated annealing and molecular dynamics steps of the procedure were performed on the structure of an HBV peptide presented by $K^d$. As shown in FIGS. 6B and 4D, the viral peptide was predicted to be relatively rigid in the $K^d$ binding groove.

For the data in FIG. 6B, average peptide structures were calculated from the 50 ns of simulation data for each pMHC, and all common atoms of pairs of mutant and WT peptides superimposed to generate the RMSD. For the data in FIGS. 6C-E and FIG. 9, root mean square fluctuations were computed for the $\alpha$ carbons of the peptides from the 50 ns of simulations.

Statistical analysis. P-values for group comparisons were calculated using a two-tailed non-parametric Mann-Whitney test, using GraphPad Prism 5.0 (GraphPad Software, Inc., La Jolla CA). For tumor rejection assays, Grubb' test was used to remove up to one outlier from each group. Fisher's exact test was used to test association between pairs of categorical parameters. Statistical significance of a Pearson correlation coefficient was computed using two-sided Student's t-test as known in the art.

Figure 3:
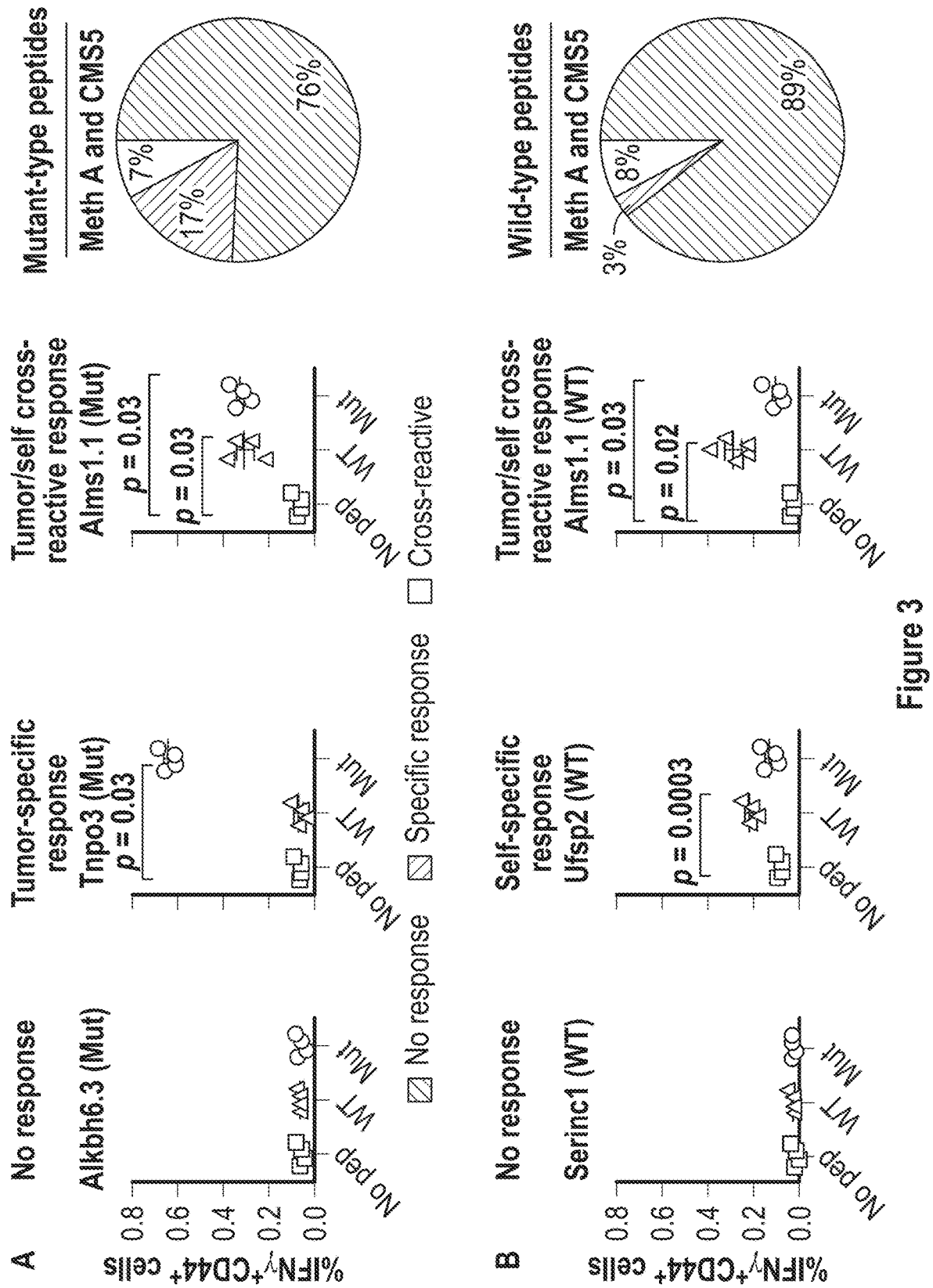
FIG. 3 shows the immunogenicity of epitopes generated by point mutations. (A) Representative examples of mutant peptides that elicited no response, tumor-specific (i.e., mutant peptide specific) response, or tumor/self cross-reactive response. The right pie chart shows the % of type of T cell response elicited by mutated peptides from Meth A (n=39) and CMS5 (n=27). (B) Representative examples of un-mutated counterparts of selected mutant peptides that elicited no response, un-mutated peptide-specific response, or cross-reactive functional CD8 response (as in A). The right pie chart shows the % of type of T cell response elicited by un-mutated peptides from both tumors. (C) Mice were immunized 100 µg of the indicated peptide once (Prime), or twice (Boost) with a 29-day interval. Seven days after the last immunization, draining popliteal LNs were harvested for intracellular cytokine assay. Lymphocytes were stimulated, or without stimulation, with 10 µg/ml cognate peptides for 16 hours and stained for CD4, CD8 and CD44, followed by permeabilization and staining for IFNγ. Shown are the percent CD44+ IFNγ+ cells of total CD8+ cells stimulated with peptides (Pep) and without peptide stimulation (No pep). Error bars represent SEM. Immunogenicity of each peptide was tested in two to four mice each and the experiments were performed between four and six times. See FIG. 9 for FACS gating strategy and representative primary data.
Figure 3:
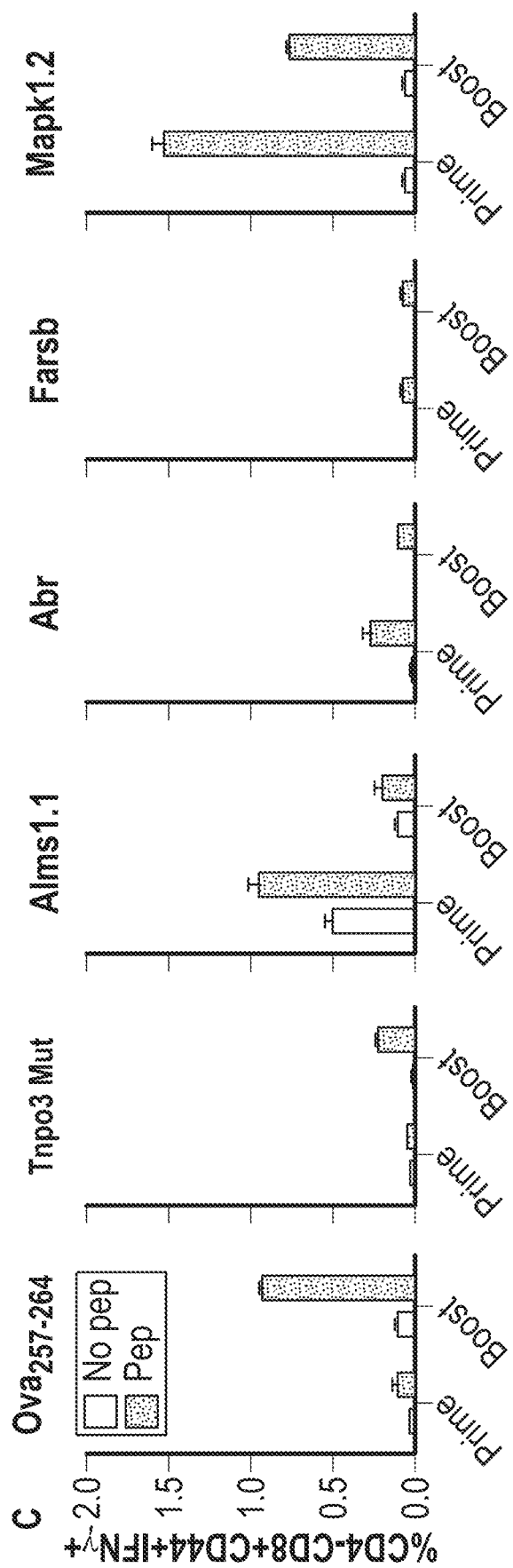

FIGS. 9 and 10 show the FACS gating strategies and representative primary data for FIG. 3 and FIG. 8C respectively.

Results

From transcriptome to immunome. A methylcholanthrene-induced fibrosarcoma, CMS5 (BALB/c, d haplotype) was used as the primary workhorse, and the results were cross-tested to varying degrees with another chemically induced (Meth A) mouse tumor as well as several human cancers. The CMS5 sarcoma is well characterized, as is the primary host in which this tumor first arose. It is a progressively growing tumor, which is lethal in a syngeneic host. CTLs against a CMS5 line have led to the identification of a single immunogenic and tumor-protective neo-epitope.

Transcriptome sequencing was chosen over genome or exome sequencing in order to identify mutations specifically in the genes expressed in CMS5 and Meth A. Broadly speaking, the cDNA sequences obtained were compared with the normal mouse sequences, and single nucleotide variants (SNVs) were identified (Table 1). FIG. 1 shows the bioinformatic pipeline and FIG. 2 and Table 2 show the quality control steps created for this analysis. This pipeline, named Epi-Seq, is accessible at http://dna.engr.uconn.edu/software/Epi-Seq. The SNVs were analyzed for their potential to generate MHC I-restricted epitopes of the murine H-2 K, D or L alleles using the NetMHC algorithm. The complete list of epitopes was filtered based on default NetMHC 3.0 PWM peptide binding score thresholds for weak binders, of 8.72, 8.08, and 8.19 for $K^d$, $D^d$, and $L^d$, respectively. Using these thresholds, CMS5 and Meth A were observed to harbor 112 and 823 potential epitopes respectively (data not shown); the difference in the number of epitopes identified between these two lines is a reflection of the depth to which their transcriptomes were sequenced (Table 1). The putative neo-epitopes are randomly distributed over the entire genome.

TABLE 1

SINGLE NUCLEOTIDE VARIANTS AND PREDICTED EPITOPES OF TUMOR LINES AND PRIMARY TUMORS AS DEDUCED FROM TRANSCRIPTOME SEQUENCING AND BIO-INFORMATIC ANALYSES.

| | Mouse Strain BALB/c Tumor Type | |
|---|---|---|
| | Meth A | CMS5 |
| RNA-Seq Reads (Million) | 105.8 | 23.4 |
| Genome Mapped | 75% | 54% |
| Transcriptome Mapped | 83% | 59% |
| HardMerge Mapped | 65% | 48% |
| After PCR Amplification Filter | 18% | 22% |
| HardMerge and Filtered Mapped Bases (Gb) | 1.15 | 0.24 |
| High-Quality Heterozygous SNVs in CCDS Exons* | 1,528 | 208 |
| Tumor Specific | 1,504 | 191 |
| Non-synonymous | 77.1% | 78.5% |
| Missense | 1,096 | 146 |

TABLE 1-continued

SINGLE NUCLEOTIDE VARIANTS AND PREDICTED EPITOPES OF TUMOR LINES
AND PRIMARY TUMORS AS DEDUCED FROM TRANSCRIPTOME SEQUENCING
AND BIO-INFORMATIC ANALYSES.

|  | Mouse Strain BALB/c Tumor Type | |
|---|---|---|
|  | Meth A | CMS5 |
| Nonsense | 63 | 4 |
| No-stop | 1 | — |
| NetMHC Predicted Epitopes** | 823 | 112 |
| H2 $K^d$-restricted | 203 | 15 |
| H2 $D^d$-restricted | 328 | 58 |
| H2 $L^d$-restricted | 292 | 39 |

*The number of mutations identified depends on the sequencing depth.
**Based on default NetMHC 3.0 PWM peptide binding score thresholds for weak binders, of 8.72, 8.08, and 8.19 for $K^d$, $D^d$, and $L^d$ alleles, respectively.

TABLE 2

MAPPING SNV, AND NETMHC PREDICTED EPITOPE STATISTICS FOR 3
LANES OF METH A RNA-SEQ READS

|  | Number of RNA-Seq lanes | | |
|---|---|---|---|
|  | 1 | 2 | 3 |
| RNA-Seq Reads (Million) | 35.9 | 62.9 | 105.8 |
| Genome Mapped | 75% | 86% | 75% |
| Transcriptome Mapped | 83% | 95% | 83% |
| HardMerge Mapped | 66% | 75% | 65% |
| After PCR Amplification Filter | 27% | 24.89% | 18% |
| HardMerge and Filtered Mapped Bases (Gb) | 0.59 | 0.94 | 1.15 |
| High-Quality Heterozygous SNVs in CCDS Exons | 958 | 1,342 | 1,504 |
| Non-synonymous | 75.9% | 76.5% | 77.1% |
| Missense | 691 | 971 | 1,096 |
| Nonsense | 35 | 55 | 63 |
| No-stop | 1 | 1 | 1 |
| NetMHC Predicted Epitopes | 537 | 729 | 823 |
| H2 $K^d$-restricted | 116 | 182 | 203 |
| H2 $D^d$-restricted | 222 | 280 | 328 |
| H2 $L^d$-restricted | 199 | 267 | 292 |

An attempt was made to determine if the numbers of MHC I-restricted neo-epitopes in these mouse tumors are within the range expected in actual primary human tumors. An analysis of exome sequences of several human melanomas and their comparison with corresponding normal sequences through the bioinformatic pipeline reveals hundreds of putative neo-epitopes per melanoma (Table 3). Similarly, the list of mutations derived from transcriptome sequencing of 14 human prostate cancers and normal tissues, led to identification of a median of 14 putative epitopes (range 2-82) for the common HLA alleles (Table 4). The smaller number of neo-epitopes in prostate cancers is related to the fact that they harbor relatively smaller numbers of mutations as compared to melanomas. The published data for the B16 melanoma line of spontaneous origin also reveal the presence of over one hundred MHC I-restricted neo-epitopes. These measurements indicate that regardless of their murine or human origin, and regardless of etiology, tumors harbor a significant number of candidate MHC I-restricted neo-epitopes.

TABLE 3

TUMOR-SPECIFIC POLYMORPHISMS AND EPITOPES FOR HUMAN MELANOMAS*

| | Somatic mutations reported in Wei et al. 2011 (13) | | | | | | | | | |
|---|---|---|---|---|---|---|---|---|---|---|
| | Synonymous/nonsynonymous in UCSC annotation | | Subset of nonsynonymous mutations (A) within CCDS coding regions | | | | NetMHC predicted epitopes** | | | |
| | | Non- | | Non- | | | | | | |
| Sample | Synonymous | synonymous (A) | Total | synonymous* | Mis-sense | Non-Sense | Total | A0101 | A0201 | A0301 |
| 01T | 160 | 304 | 292 | 291 | 272 | 12 | 473 | 26 | 262 | 185 |
| 05T | 56 | 115 | 106 | 106 | 100 | 6 | 175 | 12 | 116 | 47 |
| 09T | 39 | 83 | 81 | 80 | 76 | 4 | 131 | 5 | 77 | 49 |

TABLE 3-continued

TUMOR-SPECIFIC POLYMORPHISMS AND EPITOPES FOR HUMAN MELANOMAS*

| | Somatic mutations reported in Wei et al. 2011 (13) | | | | | | | | | |
|---|---|---|---|---|---|---|---|---|---|---|
| | Synonymous/nonsynonymous in UCSC annotation | | Subset of nonsynonymous mutations (A) within CCDS coding regions | | | | NetMHC predicted epitopes** | | | |
| Sample | Synonymous | Non-synonymous (A) | Total | Non-synonymous* | Mis-sense | Non-Sense | Total | A0101 | A0201 | A0301 |
| 12T | 427 | 741 | 706 | 705 | 656 | 49 | 1193 | 50 | 657 | 486 |
| 18T | 91 | 190 | 179 | 179 | 168 | 11 | 286 | 15 | 144 | 127 |
| 22T | 69 | 126 | 116 | 115 | 108 | 7 | 181 | 20 | 94 | 6? |
| 24T | 163 | 397 | 381 | 379 | 358 | 21 | 625 | 26 | 263 | 336 |
| 35T | 13 | 34 | 32 | 32 | 31 | 1 | 68 | 1 | 44 | 23 |
| 43T | 68 | 94 | 91 | 91 | 86 | 5 | 175 | 4 | 90 | 81 |
| 51T | 51 | 136 | 126 | 126 | 117 | 9 | 229 | 7 | 148 | 74 |
| 60T | 67 | 129 | 121 | 120 | 112 | 8 | 209 | 14 | 91 | 104 |
| 91T | 99 | 215 | 209 | 209 | 196 | 13 | 329 | 18 | 173 | 135 |
| 93T | 54 | 130 | 125 | 124 | 116 | 8 | 184 | 6 | 105 | 73 |
| 96T | 68 | 118 | 112 | 112 | 103 | 9 | 192 | 10 | 101 | 81 |

*Calculated from mutation data published by Wei et al. 2011 and using the epitope prediction step of the Epi-Seq pipeline summarized in FIG. S1 to call the epitopes based on the mutation data.
**Most common HLA alleles were chosen according to the published frequencies of such alleles.

TABLE 4

TUMOR-SPECIFIC POLYMORPHISMS AND EPITOPES FOR HUMAN PROSTATE CANCERS

| | Somatic mutations reported in Ren et al. 2012 (14) | | | | | | | | | |
|---|---|---|---|---|---|---|---|---|---|---|
| | Synonymous/nonsynonymous in UCSC annotation | | Subset of nonsynonymous mutations within CCDS coding regions | | | | NetMHC predicted epitopes | | | |
| Tumor Sample | Synonymous | Non-synonymous | Total | Heterozygous | Mis-sense | Non-sense | Total | A1101 | A2402 | A0201 |
| 1T | 7 | 10 | 10 | 10 | 9 | 1 | 9 | 4 | 0 | 5 |
| 2T | 4 | 3 | 2 | 2 | 2 | 0 | 4 | 4 | 0 | 0 |
| 3T | 7 | 4 | 3 | 3 | 3 | 0 | 10 | 5 | 1 | 4 |
| 4T | 5 | 3 | 3 | 3 | 3 | 0 | 2 | 2 | 0 | 0 |
| 5T | 4 | 7 | 7 | 7 | 7 | 0 | 18 | 12 | 2 | 4 |
| 6T | 3 | 5 | 5 | 5 | 4 | 1 | 3 | 1 | 0 | 2 |
| 7T | 2 | 3 | 2 | 2 | 2 | 0 | 2 | 1 | 1 | 0 |
| 8T | 20 | 44 | 40 | 40 | 38 | 2 | 82 | 42 | 7 | 33 |
| 9T | 13 | 22 | 18 | 18 | 16 | 2 | 30 | 13 | 0 | 17 |
| 10T | 20 | 32 | 29 | 29 | 28 | 1 | 36 | 20 | 3 | 13 |
| 11T | 6 | 13 | 9 | 9 | 9 | 0 | 17 | 8 | 2 | 7 |
| 12T | 3 | 11 | 10 | 10 | 10 | 0 | 28 | 13 | 5 | 10 |
| 13T | 2 | 5 | 5 | 5 | 5 | 0 | 9 | 2 | 3 | 4 |
| 14T | 19 | 32 | 29 | 29 | 24 | 5 | 53 | 25 | 8 | 20 |

Heterogeneity of neo-epitopes. Meth A cells were cloned, and 30 distinct clones were tested for four SNVs picked at random (Tnpo3, NFkb1, Prp31 and Psg17). Unexpectedly, all but a single SNV was detected in all the clones; a single SNV was detected in 29/30 clones tested. Without being held to theory, this apparent lack of antigenic heterogeneity is attributed to the relatively shallow depth of sequencing. It is also possible that cancer cell lines show less antigenic heterogeneity than primary tumors. Most importantly, these results suggest it is possible to use a relatively shallow sequencing as a methodology to identify the neo-epitopes that are the most broadly distributed among cancer cells.

Immunogenicity of neo-epitopes identified in silico. In order to reduce the complexity of analyses, attention was directed towards the 218 $K^d$-restricted epitopes (for Meth A and CMS5 combined) from a total list of 935 for all three alleles (Table 3). All the mutations used for immunological analyses were confirmed individually by Sanger sequencing.

The neo-epitopes were ranked in descending order of their NetMHC scores for $K^d$-binding. The top 7 neo-epitopes from CMS5 and the top 11 from Meth A are shown in Table 5, which also shows the NetMHC score of the wild type (WT) peptide corresponding to the neo-epitope. Peptides corresponding to these 18 putative neo-epitopes and their WT counterparts were synthesized, and the affinity of all peptides for $K^d$ (IC50 values) was determined experimentally as described in Methods. (NetMHC scores and experimentally determined IC50 values were significantly correlated; r=−0.44, two-tailed t-test P<0.001). Ten of 18 top-ranked neo-epitopes (56%) bound $K^d$ with an affinity of 500 nM or better, and 7/18 (39%) bound with an affinity of 100 nM or better.

TABLE 5

CMS5 AND METH A EPITOPES WITH HIGHEST NEIMHC FWM SCORES.

| Gene | Mut/WT Sequence | SEQ ID NO: | Mut/WT Score | Measured IC50 for $K^d$ (Mut/WT) | ICS | ELISpot | Tumor Rejection |
|---|---|---|---|---|---|---|---|
| CMS5 Epitopes with fewest NetMHC scores ||||||||
| Ssx2ip | CYAK(v/L)KEQL | 6/7 | 14.5/14.1 | 26/3.2 | − | − | − |
| Mapk1.1 | (q/K)YIHSANVL | 8/9 | 13.2/12.4 | 57/0.2 | − | − | − |
| Farsb | HY(v/L}HIIESKPL | 10/11 | 13/13.6 | 423/52 | + | − | − |
| Ncoa3 | (h/Q)YLQYKQEDL | 12/13 | 11.5/11.7 | 2162/54074 | − | − | − |
| Mapk1.2 | (q/K)YIHSANV | 14/15 | 11.4/10.7 | 2135/295 | − | − | − |
| Mapk1.3 | LVQILRGL(q/K)YI | 16/17 | 11.3/11 | 110/333 | − | +++++ | − |
| Serine1 | NYLLSLYVAV(m/V)L | 18/19 | 11/10.2 | 2679/20861 | − | +++++ | − |
| Meth A Epitopes with the highest NetMHC scores ||||||||
| Usp12 | SY(l/R)VVYFPL | 20/21 | 14.2/12.3 | 6835/1155 | − | +++++ | − |
| Tfdp1 | QYSGS(w/R)VVTFV | 22/23 | 14.2/15.3 | −*/603 | − | − | − |
| Ufsp2 | HYINM(i/S)LPI | 24/25 | 14.2/14.5 | 0.23/+++** | + | +++++ | − |
| Apc | AYCETCW(l/V) | 26/27 | 14/8.1 | 23/60 | + | − | − |
| Hspg2 | SY(l/Q)LGSGEARL | 28/29 | 14/14.4 | 2623/79 | − | − | − |
| Ccdc85c | TYIRF(f/L)ETKV | 30/31 | 13.5/13.1 | 6155/118 | − | − | − |
| Pacs2 | HYLS(s/A)ILRL | 32/33 | 13.4/12.7 | 41/1269 | − | − | − |
| Alms1.1 | (l/S)YLDSKSDTTV | 34/35 | 133/15.2 | 79/16 | + | − | − |
| Alms1.2 | YYVPLLKRVP(l/S) | 36/37 | 13.3/7.3 | 421/1485 | − | ++ | − |
| Ckap5 | K(y/D)MSMLEERI | 38/39 | 13.2/1.7 | 17/7686 | + | − | − |
| Abr | GYFVSKAKT(s/R)V | 40/41 | 13.1/12.8 | 958/570 | + | − | − |

Note for IC50:
* − indicates IC50 >70,000 nM,
**+++ − indicates IC50 <0.1 nM

Note for ELISPOT Results:
1-9 spots/$10^6$ CD8 = +,
10-20 spots/$10^6$ CD8 = ++,
21-50 spots/$10^6$ CD8 = +++,
51-100 spots/$10^6$ CD8 = ++++,
>100 spots/$10^6$ CD8 = +++++

All 18 peptides were used to immunize BALB/c mice. The draining lymph nodes (dLNs) of immunized mice were harvested one week after the single immunization, and the cells were stimulated in vitro for 16 h without any added peptide, the mutant peptide used for immunization, or the corresponding wild type peptide. The CD8+ cells were analyzed for activation (CD44+) and effector function (intracellular IFNγ+) (see Materials and Methods regarding the details of FACS analysis.) All possible patterns of immune-reactivity were observed (FIG. 3A): no immune response (12/18), a mutant peptide-specific, i.e., tumor-specific immune response (5/18), and a cross-reactive response between the mutant and corresponding wild type peptides (1/18). Altogether, 6/18 or 33% of the neo-epitope candidates identified in silico actually elicited functional effector T cells in vivo. When analyzed by an IFNγ ELISPOT assay, three additional neo-epitopes showed immunogenicity, bringing the total to 9/18 or 50%.

Of the 10 peptides with a $K^d$-binding affinity of 500 nM or better, 5 or 50% were determined to be immunogenic experimentally. Of the 7 peptides with a $K^d$-binding affinity of 100 nM or better, 4 or 57% were immunogenic. Only one peptide with a $K^d$-binding affinity of 500 nM or worse was immunogenic.

Lack of immunogenicity of WT peptides. While testing for immunogenicity of neo-epitopes, their WT counterparts were similarly tested (FIG. 3B). Surprisingly, as with the mutant neo-epitopes (FIG. 3A), all possible patterns of immune-reactivity were observed (FIG. 3B): no immune response (11/18), a WT peptide-specific immune response (5/18), and a cross-reactive response between the mutant and corresponding wild type peptides (2/18). Altogether, 7/18 or 39% of the WT counterparts of neo-epitope candidates identified in silico elicited functional effector T cells in vivo (Alms1.1, Alms1.2, Abr, Ccdc85c, Farsb, Mapk1.2, Ufsp2, see Table 5).

This was still a surprisingly large proportion of self-reactive peptides in view of the strong role of negative selection in sculpting of the T cell repertoire. The possibility that the WT peptides that are immunogenic are functionally tolerized, even though they show immunogenicity in an ex vivo assay, was tested. Without being held to theory, it was hypothesized that if a small proportion of low affinity auto-reactive T cells escaped negative selection, they may still be clonally expanded to a degree upon immunization with a self peptide, but that such an expansion would prove self-limiting. Hence, naïve mice were immunized with the peptides, followed by a second immunization, and the responses in naïve mice, once-immunized mice, and twice-immunized mice were compared. The ovalbumin-derived $K^b$-binding epitope SIINFEKL (SEQ ID NO: 1) was used as a positive control, and indeed the magnitude of the anti-SIINFEKL CD8 response was amplified by a second immunization (FIG. 3C). This same phenomenon was observed with the mutant neo-epitope Tnpo3. However, second immunization with 4/4 WT peptides tested did not elicit an amplification of the response. Indeed, responses detected after the second immunization were significantly diminished as compared with the response after the first immunization. By this stringent criterion, not a single WT peptide was observed to be immunogenic.

Lack of immuno-protective activity of the strongest $K^d$-binding neo-epitopes. All 18 neo-epitopes (Table 5) were tested for their ability to elicit tumor rejection of CMS5 or Meth A. BALB/c mice were immunized with the individual peptides and were challenged with the appropriate tumor one week after the last immunization. None of the peptides elicited tumor rejection (FIG. 4A). Interestingly, one of the neo-epitopes identified by us Mapk1 (listed as Mapk1.1, 1.2 and 1.3 in Table 4), was also identified by the prior art in the CMS5 sarcoma as a tumor rejection antigen. Immunization with it does not elicit tumor rejection in our hands, just as it did not in the original paper. The authors of the original paper noted that "IL-12 treatment was essential to show antitumor immunity in this system, because mice vaccinated with 9m-pulsed spleen cells in the absence of exogenous IL-12 showed no resistance to CMS5 challenge." This is an un-intended validation of our pipeline and also highlights the fact that we have used a very stringent tumor rejection assay in our analyses.

Differential agretopicity. From the results above, it is evident that the NetMHC score is not a valuable predictor of immunogenicity or tumor rejection. A close examination of the data in Table 5 suggests an underlying possibility: for each entry, both the neo-antigen and its WT counterpart have similar NetMHC scores characteristic of high affinity peptide binding. Moreover, examining the experimental IC50 values, 4/7 WT peptides of CMS5 and 7/11 WT peptides of Meth A have stronger affinity for $K^d$ than the mutant peptides. Thus, unless the mutations alter TCR contacts or the structural properties of the peptides in the $K^d$ binding groove, T cells potentially reactive to the neo-epitopes may have been centrally deleted or peripherally tolerized.

We therefore created a new algorithm wherein the NetMHC scores of the un-mutated counterparts of the predicted mutated epitopes were taken into consideration by subtracting them from the corresponding NetMHC scores of the mutated epitopes. We refer to this new property of an epitope as the Differential Agretopic Index (DAI), and we expect it to reflect the degree to which the peptide-binding determinants of the neo-epitopes differ from those of their WT counterparts. In the search for the rules for immunogenicity of viral or other clearly non-self epitopes, such a parameter is not necessary, nor possible, and has therefore never been sought. The putative epitopes were ranked on basis of the DAI (Table 6). A review of this DAI-ranked list for both tumors shows curiously that all the neo-epitopes in this new ranking are mutated at one of the two primary anchor residues at positions 2 or the C-terminus (we did not identify any neo-epitope with changes at both anchor residues.) Consistent with the $K^d$ preferences gleaned from structural analyses, all of these mutations involve aspartic acid to tyrosine at position 2 or proline/arginine to leucine at the C-terminus. Although the DAI was not crafted for this outcome, it is a perfectly reasonable outcome in hindsight.

TABLE 6

CMS5 AND METH A EPITOPES WITH HIGHEST DAI SCORES

| Gene | Mut/WT Sequence | SEQ ID NO: | Mut/WT Score | DAI | Measured IC50 for $K^d$ (Mut/WT) | ICS | ELISpot | Tumor Rejection |
|---|---|---|---|---|---|---|---|---|
| CMS5 Epitopes | | | | | | | | |
| Dhx8.1 | P(y/D)LTQYAIIML | 42/43 | 9.3/−2.3 | 11.6 | 2192/1653 | − | +++++ | − |
| Alkbh6.1 | D(y/D)VPMEQP | 44/45 | 4.3/−7.3 | 11.6 | 60858/− | − | − | − |
| Dhx8.2 | P(y/D)LTQYAI | 46/47 | 9.9/1.6 | 11.5 | −*/− | − | +++++ | − |
| Dhx8.3 | P(y/D)LTQYAII | 48/49 | 9.3/−2.2 | 11.5 | 244/1418 | + | +++++ | − |
| Alkbh6.2 | D(y/D)VPMEQPR | 50/51 | 6.8/−4.8 | 11.5 | −/51229 | − | ++ | + |
| Dhx8.4 | P(y/D)LTQYAIIM | 52/53 | 6.6/−49 | 11.5 | 6571/6256 | − | +++ | − |
| Alkbh6.3 | D(y/D)VPMEQPRP | 54/53 | 4.8/−6.7 | 11.5 | −/23570 | − | − | − |
| Alkbh6.4 | D(v D)YPMEQPRP | 56/57 | 4.7/−6.8 | 11.5 | 47053/2957 | − | − | − |
| Raagap1 | SEDKIKAI(l/P) | 58/59 | 1.4/−5.4 | 6.8 | −/5103 | − | +++++ | − |
| Stsu1.1 | LKSEEKT(l/P) | 60/61 | 0.6/−6.2 | 6.8 | −/− | − | − | − |
| Stau1.2 | KPALKSEEKT(l/P) | 62/63 | 0.1/−6.7 | 6.8 | −/− | − | − | − |

TABLE 6-continued

CMS5 AND METH A EPITOPES WITH HIGHEST DAI SCORES

| Gene | Mut/WT Sequence | SEQ ID NO: | Mut/WT Score | DAI | Measured IC50 for $K^d$ (Mut/WT) | ICS | ELISpot | Tumor Rejection |
|---|---|---|---|---|---|---|---|---|
| Stau1.3 | PALKSEEKT(1/P) | 64/65 | 1.3/-5.4 | 6.7 | 69546/- | - | - | - |
| Stau1.4 | ALKSEEKT(1/P) | 66/67 | 1.2/-5.5 | 6.7 | -/- | - | - | + |
| 9430016 H08Rik | SWSSRRSLLG(1/R) | 68/69 | 5.9/-0.6 | 6.5 | -/- | - | +++++ | - |
| Slit3 | GFHGCIHEV(1/R) | 70/71 | 4.7/-1.8 | 6.5 | 51640/- | + | +++ | + |
| Atxn10.1 | QVFPGLME(1/R) | 72/73 | 3.4/-3.1 | 6.5 | -/7054 | + | +++ | + |
| Sipa1l3 | TTTPGGRPPY(1/R) | 74/75 | 2.7/-3.8 | 6.5 | -/- | - | ++++ | - |
| Atxn10.2 | VFPGLME(1/R) | 76/77 | 2.4/-4 | 6.5 | -/1107 | - | - | + |
| Ccdc136 | ELQGLLEDE(1/R) | 78/79 | 2.4/-4.1 | 6.3 | -/4537 | - | - | + |
| Mast2 | KLQRQYRSPR(1/R) | 80/81 | 2.2/-4.3 | 6.5 | 10107/8511 | - | - | - |
| Meth A epitopes | | | | | | | | |
| Tnpo3.1 | (sy/LD)MLQALCI | 82/83 | 8.2/-5.2 | 13.4 | 82/146 | + | +++++ | + |
| Tnpo3.2 | (sy/LD)MLQALCIPT | 84/85 | 7.1/-6.3 | 13.4 | 9964/85 | + | +++ | - |
| Tnpo3.3 | (sy/LD)MLQALCIP | 86/87 | 3/-10.4 | 13.4 | 67/111 | + | +++++ | - |
| Tnpo3.4 | (sy/LD)MLQALC | 88/89 | 5.9/-7.4 | 13.3 | 14927/89 | - | - | - |
| Trim26.1 | A(Y/D)ILAALTKL | 90/91 | 12.8/1.2 | 11.6 | 622/1.1 | - | +++++ | - |
| Nus1 | P(y/D)LVLKFGPV | 92/93 | 10.5/-1.1 | 11.6 | 2359/1.9 | - | - | - |
| Tpst2.1 | L(y/D)EAGVTDEV | 94/95 | 10.3/-1.3 | 11.6 | 60/- | - | +++ | - |
| Fiz1 | H(y/D)LQGSNA | 96/97 | 36.3/-1.3 | 11.6 | 2473/- | - | - | - |
| Kdm4b | L(y/D)HTRPTAL | 98/99 | 10/-1.6 | 11.6 | 264/- | - | - | - |
| Dis3l2.1 | I(y/D)GVVARNRAL | 100/101 | 9.3/-2.3 | 11.6 | 143/- | + | + | - |
| Ube4a.1 | A(y/D)AKQFAAI | 102/103 | 9.3/-2.3 | 11.6 | 12/- | + | + | - |
| Ncdn | S(y/D)CEPALNQA | 104/105 | 8.9/-2.7 | 11.6 | 664/- | + | - | - |
| Gapdh | V(y/D)LTCRLEKA | 106/107 | 8.9/-2.7 | 11.6 | 1150/- | - | - | - |
| Ckap5 | K(y/D)MSMLEER | 108/109 | 8.1/-3.5 | 11.6 | 58/- | - | +++ | - |
| Prrc2a | P(y/D)KRLKAEPA | 110/111 | 7.9/-3.7 | 11.6 | 1450/261 | - | - | - |
| Tmx3 | I(y/D)IIEFAHRV | 112/113 | 7.3/-4.3 | 11.6 | 7941/353 | - | - | - |
| Nfkb1 | G(y/D)SVLHLAI | 114/115 | 6.9/-4.6 | 11.6 | 0.26/1615 | + | - | + |
| Dis3l2.2 | I(y/D)GVVARNRA | 116/117 | 6.9/-4.7 | 11.6 | 1342/462 | - | - | - |
| ugdh | U(y/D)YERIHKKML | 118/119 | 6.4/-5.2 | 11.6 | 600/12 | - | - | - |
| M112 | S(y/D)RLFSSRKK | 120/121 | 5.9/-5.7 | 11.6 | 6673/17 | - | + | - |
| Galnt1 | L(y/D)VSKLNGP | 122/123 | 5.6/-6 | 11.6 | 27086/- | - | - | - |
| Tpst2.2 | L(y/D)EAGVTDE | 124/125 | 5.5/-6.1 | 11.6 | -/- | - | +++ | - |
| Cpsf2 | L(y/D)DVDAAF | 126/127 | 5.3/-6.3 | 11.6 | 1410/- | - | +++ | + |
| Zfp236.1 | E(y/D)LDLQTQ | 128/129 | 5.3/-6.3 | 11.6 | 1641/- | - | +++ | + |
| Trim26.2 | A(y/D)ILAALTKLQ | 130/131 | 4.9/-6.7 | 11.6 | 17599/- | - | - | - |
| Zfp236.2 | E(y/D)LDLQTQG | 132/133 | 4.9/-6.7 | 11.6 | 10028/- | - | ++++ | - |

TABLE 6-continued

CMS5 AND METH A EPITOPES WITH HIGHEST DAI SCORES

| Gene | Mut/WT Sequence | SEQ ID NO: | Mut/WT Score | DAI | Measured IC50 for $K^d$ (Mut/WT) | ICS | ELISpot | Tumor Rejection |
|---|---|---|---|---|---|---|---|---|
| Ube4a.2 | A(y/D)AKQFAA | 134/135 | 4.7/−6.9 | 11.6 | 28583/− | − | − | − |
| Dcaf6 | A(y/D)RLEGDRS | 136/137 | 3.7/−7.9 | 11.6 | −/− | − | − | − |

Note
for IC50:
* − indicates IC50 >70,000 nM,
**+++ indicates IC50 <0.1 nM
Note
for ELISPOT Results:
1-9 spots/$10^6$ CD8 = +,
10-20 spots/$10^6$ CD8 = ++,
21-50 spots/$10^6$ CD8 = +++,
51-100 spots/$10^6$ CD8 = ++++,
>100 spots/$10^6$ CD8 = +++++

Figure 8:
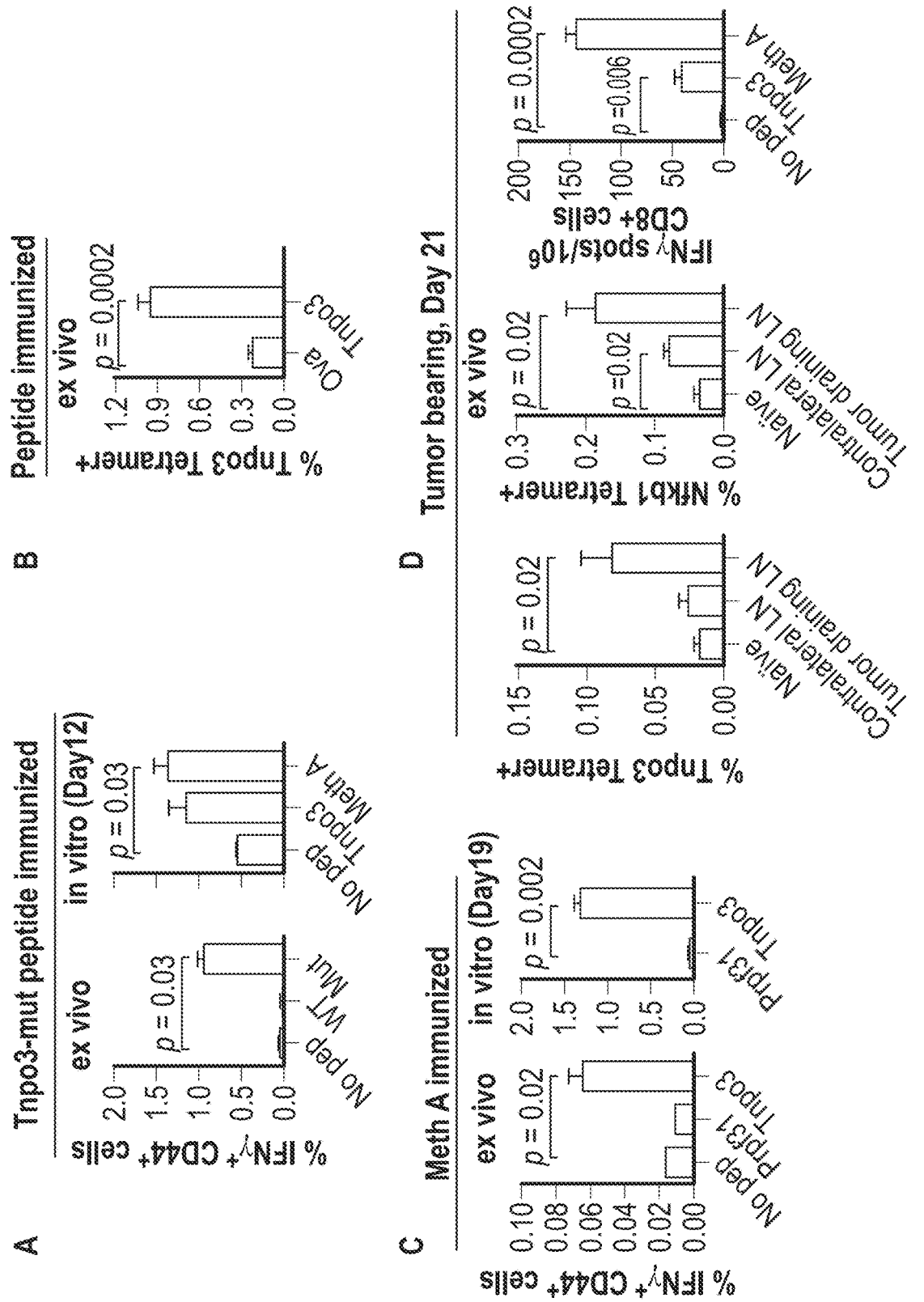
FIG. 8 shows antigen presentation of neo-epitope Tnpo3 and immune response and tumor protection elicited by it. (A) Mice were immunized with mutant Tnpo3 peptide. dLNs were briefly stimulated ex vivo without (No pep) or with WT or mutant Tnpo3 peptides (left panel), or with a weekly in vitro stimulation with 1 µM mutant Tnpo3 peptide (right panel). After 5 d, cells were tested for the responsiveness to mutant Tnpo3-pulsed cells (Tnpo3) or Meth A cells (Meth A). IFNγ+CD44+CD8+ T cells were counted. (B) Mice were immunized twice with ovalbumin peptide (SIINFEKL; SEQ ID NO: 1) or Tnpo3 mutant peptide. Six days after the second immunization, splenocytes from both groups were stained with K$^d$/SYMLQALCI (SEQ ID NO:2)
Figure 8:
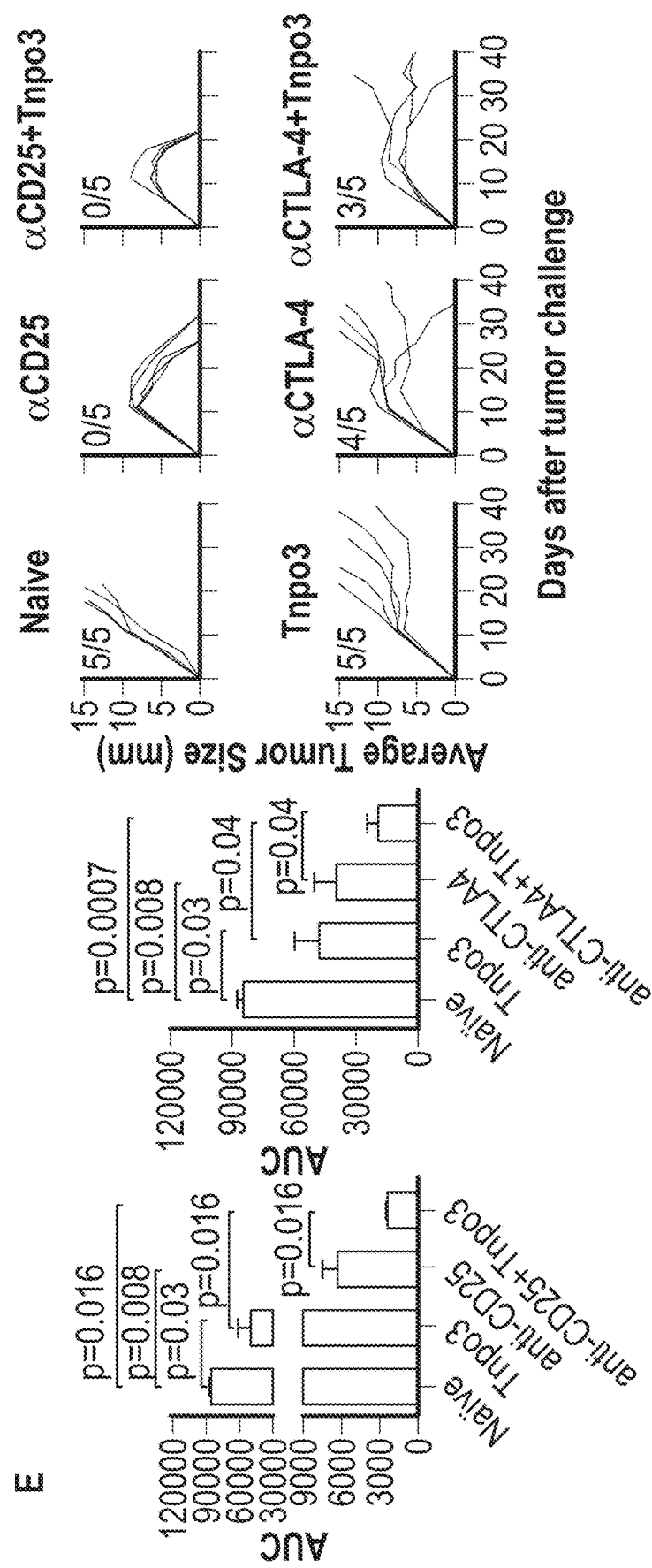

The top DAI-ranking 20 epitopes of CMS5 and 28 epitopes of Meth A were tested in tumor rejection assays. The results (FIG. 4B) show that 6/20 or 30% CMS5 epitopes and 4/28 or 14% Meth A epitopes showed statistically significant tumor protective immunogenicity. The six CMS5 neo-epitopes are particularly impressive in that they elicited near complete or complete protection from a lethal tumor challenge. FIG. 4C shows representative tumor rejection curves of the two protective and one un-protective CMS5 epitope from Table 6. Corresponding WT peptides did not mediate any tumor rejection. (Detailed data on tumor rejection elicited by a Meth A neo-epitope Tnpo3 are shown in FIG. 8.) Statistical comparison of the NetMHC alone versus the DAI algorithms in predicting anti-tumor protective immunity, using one-tailed Fisher's exact test, shows the DAI to be far superior (0/18 vs. 10/48, for NetMHC and DAI respectively, one-sided Fisher's exact test p=0.031).

Although the DAI algorithm yielded a far richer harvest of tumor-protective epitopes than the reliance on the highest NetMHC or MHC-binding scores, most epitopes identified by DAI still fail to elicit tumor protection. Further, the DAI-ranked neo-epitopes (Table 5) that elicit protection from tumor growth are not necessarily the highest ranking in DAI. Clearly, other properties of the putative epitopes (see Discussion) contribute to the tumor rejection activity of individual neo-epitopes. Regardless of its imperfection, the DAI is a statistically significant and novel predictor of tumor-protective immunogenicity, and more importantly, permits a dissection of the other potential criteria for anti-tumor immunogenicity in vivo.

The DAI algorithm also un-covers a new paradox of fundamental significance. All the six neo-epitopes that elicit protection against CMS5 have NetMHC scores between 6.8 and 1.2, which are well below 8.72, the PWM peptide binding score threshold for weak binders for $K^d$ (NetMHC3.0). Consistent with that observation, their measured IC50 values for binding to $K^d$ are >70,000 nM (for all except Slit3, for which is IC50 is approximately 50,000 nM). This observation is surprising because epitopes are typically considered good MHC I-binders if they have an IC50 value of <100 nM, or at least <500 nM. The IC50 values for the CMS5 neo-epitopes are so high (i.e., their binding to $K^d$ is so poor) that these neo-epitopes would never be considered suitable candidates for being epitopes based simply on their $K^d$-binding characteristics. For Meth A as well, all the four neo-epitopes that elicit tumor immunity have a NetMHC below the 8.72 threshold for weak binders for $K^d$; the measured $K^d$-binding affinities of only two of the four Meth A neo-epitopes are <100 nM. In order to explore the possibility that these neo-epitopes may be binding to another allele, $D^d$ or $L^d$, the six tumor-protection eliciting neo-epitopes for CMS5 were tested for binding to these two alleles by direct peptide-binding studies; none of the peptides showed significant binding (unpublished data). Because the requirement for MHC I binding to be <500 nM is so well established. The possibility that the peptides identified as being potent in eliciting protection from tumor challenge (FIG. 6B,C) may do so through non-immunological means was investigated.

CD8 dependence of tumor protection. Mice immunized with five of the six active neo-epitopes of CMS5, (Alkbh6.2, Slit3, Atxn10.1, Atxn 10.2 and cdc136) were tested for immunogenicity; as shown in Table 6, Alkbh6.2, Slit3 and Atxn10.1 elicited modest CD8 T cell response that was un-detectable by the intracellular cytokine assay, and detectable only by the ELISPOT assay (FIG. 5A), while Atxn10.2 and cdc136 did not elicit a detectable response at all. Immunized mice were depleted of CD8 or CD4 cells in the effector phase only (i.e., post-immunization but prior to tumor challenge) and were challenged with CMS5 cells as in FIG. 4. The results (FIG. 5B) show that compared with naïve mice, each mutant peptide elicited potent tumor rejection. WT Depletion of CD8 cells completely abrogated the tumor-rejecting ability of each peptide. Depletion of CD4 cells had no such effect. These data show that the CMS5 neo-epitopes that elicit tumor rejection do so through elicitation of specific CD8+ T cells, and not through non-immunological means. However, the data do not imply that CD4+ T cells do not have a role in tumor rejection; an examination of the kinetics of tumor rejection shows that in the absence of CD4+ cells, tumors actually do begin to grow in almost all the immunized mice but begin to regress by days 7-10.

Conformational stability as an indicator of immunogenicity. The CD8-dependence of neo-epitopes that have low predicted and measured affinity for their restricting allele led us to seek other determinants of immunogenicity. Although the DAI algorithm selects for mutations at primary anchor positions that improve peptide-MHC binding affinity, unless the mutations alter the structural properties of the peptide in the binding groove as discussed above, potentially responding T cells may be centrally or peripherally tolerized. Studies have shown that anchor modification can have a range of effects on MHC-bound peptides, in some cases having no apparent influence, and in others leading to alterations in structural and motional properties.

To examine the consequences of anchor modification, computational modeling was used to examine the structural properties of pairs of mutant and WT peptides bound to $K^d$. An approach recently used to model the structures of peptides bound to HLA-A*0201 was modified using the crystallographic structure of a viral peptide/H-2$K^d$ complex as a template. As described in Materials and Methods, the workflow included homology modeling, simulated annealing, and molecular dynamics simulations to predict structural properties. Because the conformations of peptide backbones in MHC I proteins vary considerably with peptide length, the modeling were restricted to pairs of nonamers in Table 6, matching the length of the peptide in the template structure. This restriction led to non-inclusion in our modeling analyses, of some of the more immunogenic and protective neo-epitopes in Table 6, simply because they are 8- or 10-mers, and not 9-mers. To ascertain how well the modeling procedure was transferable from HLA-A*0201 to H-2$K^d$, the modeling procedure was applied to the complex of the immunodominant and highly immunogenic HBV core peptide with $K^d$, a complex for which the crystallographic structure is known in the art.

Structural differences between the mutant and WT peptides were identified. In each instance, there were differences between the predicted conformations of the mutant and WT peptides bound to H-2$K^d$. In all cases, these differences propagated away from the site of the mutations (example shown in FIG. 6A). These observations were not surprising, as the mutations were all quite drastic, and even conservative mutations at class I MHC-presented peptide anchor residues can influence downstream conformation.

Figure 6:
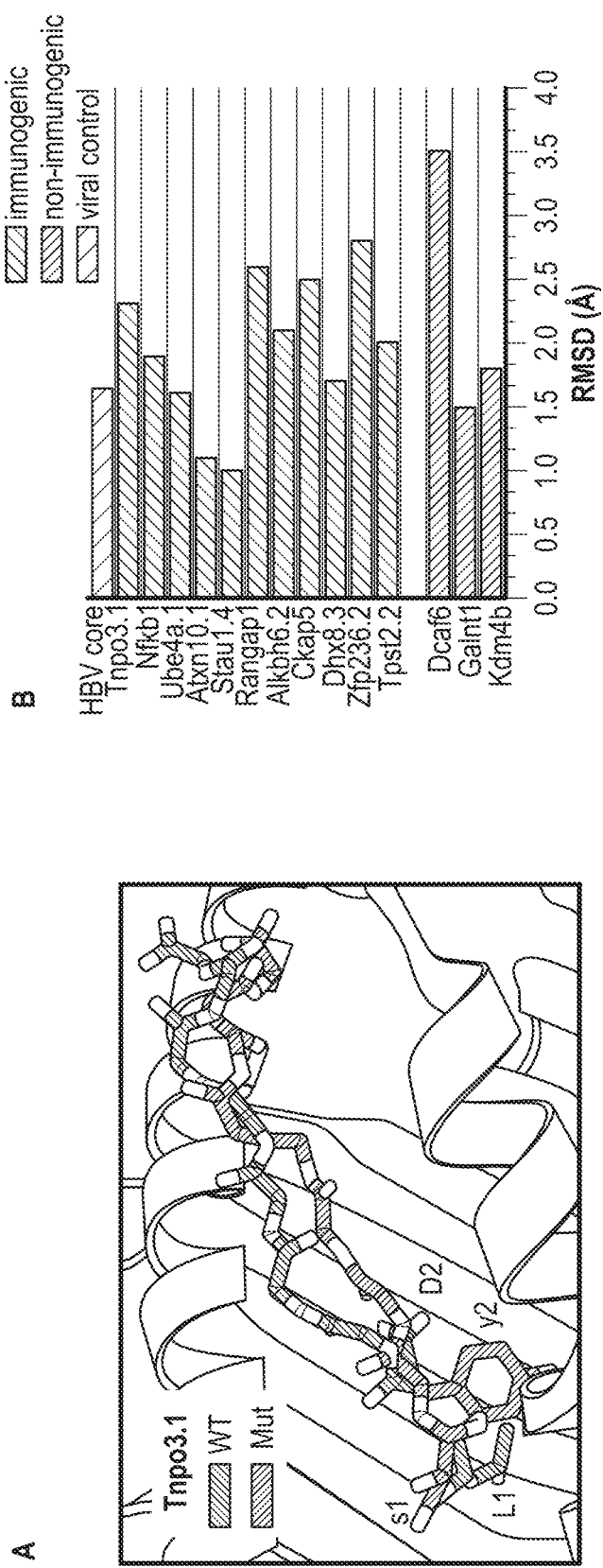
FIG. 6 shows the structural stability as a correlate with immunogenicity. (A) Mutations within neo-epitopes lead to structural alterations across the peptide backbone, as illustrated here with structural snapshots from the simulations of the mutant and WT Tnpo3.1 epitope bound to H-2K$^d$. (B) Summary of structural differences for highly DAI ranked nonamers. Differences were quantified by superimposing average peptide conformations from the molecular dynamics simulations and computing root mean square deviations for all common atoms. Upper and lower bars indicate epitopes that led to either positive or negative immunological responses, respectively. The HBV core bar shows the results for control calculations for an immunogenic HBV core epitope. (C) In addition to altering structure, mutations can increase the conformational stability of the peptides within the H-2K$^d$ peptide binding groove, as shown here for the Tnpo3.1 epitope. The mutant peptide is more conformationally stable, as demonstrated by root mean square fluctuations of peptide α carbons during the molecular dynamics simulations. The numbers in the legend give the average RMSF for the nine amino acids of each peptide; those at the right give the value for only the C-terminal α carbon. Mutated amino acids are indicated by lower case in the x-axis (D) Effects of mutations on the conformational stability of all nonamers, calculated as the difference between the average RMSF of the mutant and the WT peptide. (E) Fluctuations at the peptide C-terminal ends are an improved indicator of immunogenicity. The dashed vertical line shows the average for all mutant nonamers. The yellow bar shows the C-terminal stability of the HBV core epitope control. Error bars give the standard error of the mean.
Figure 6:
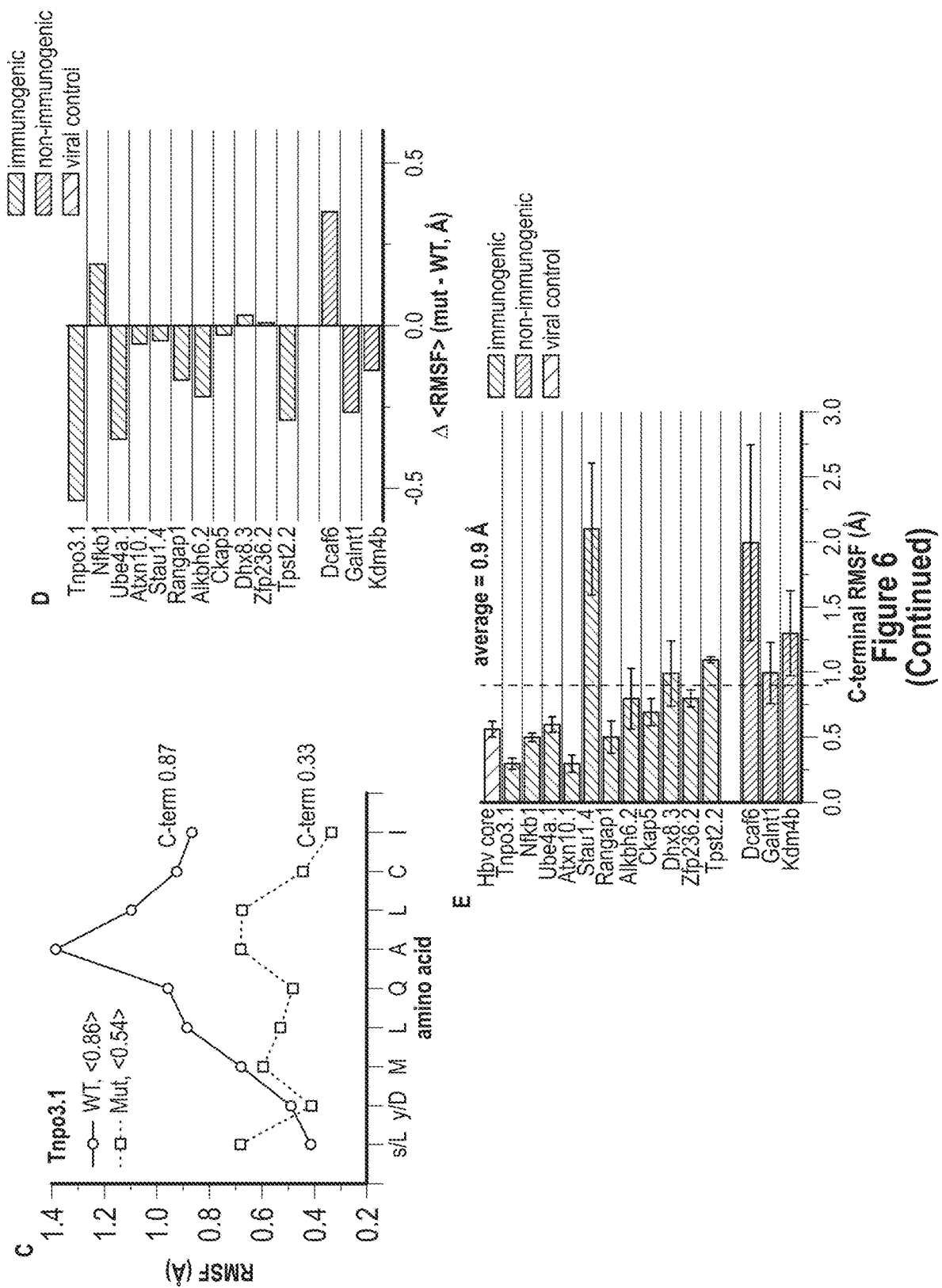
Figure 7:
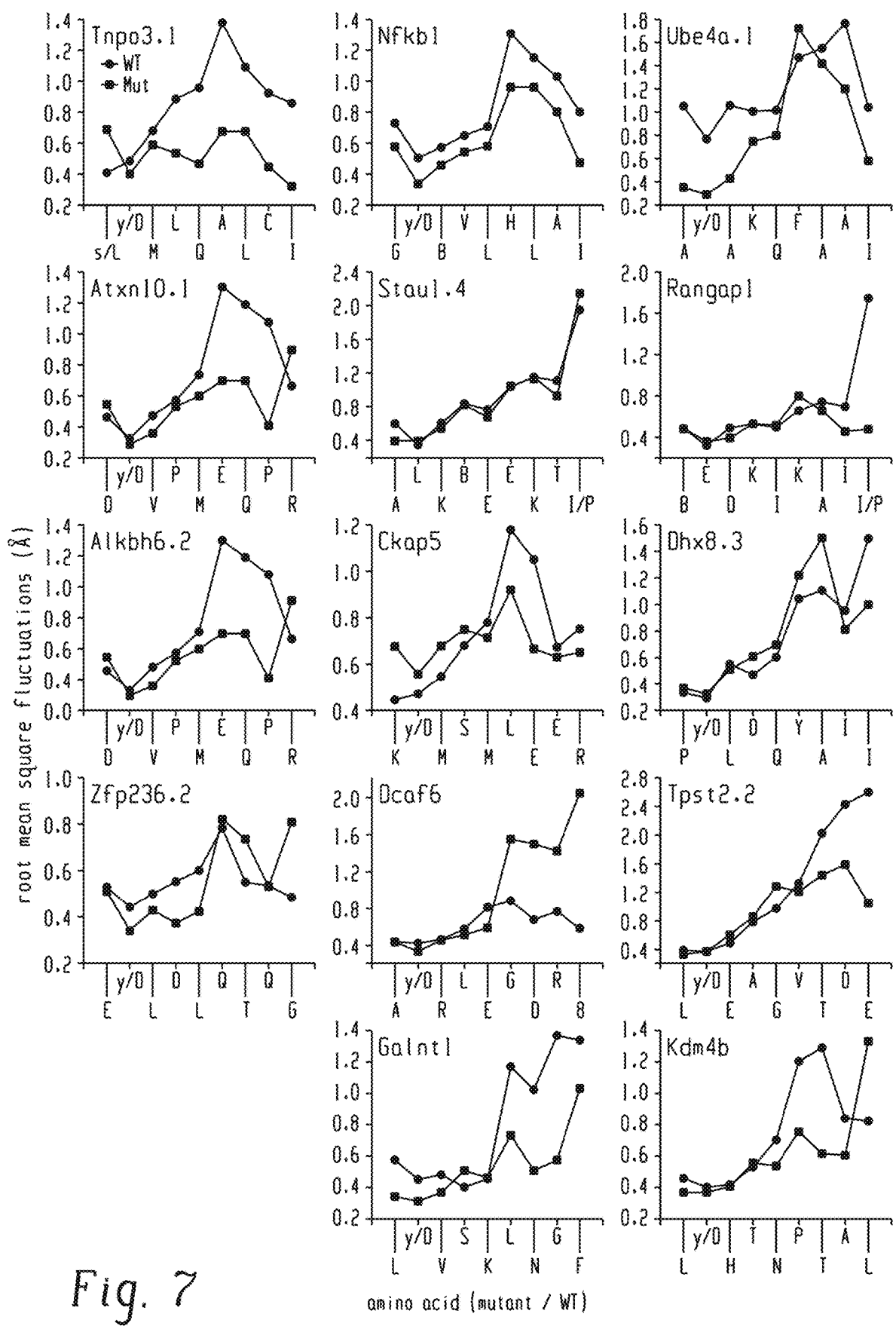
FIG. 7 shows root mean square fluctuations for the alpha carbons of all top DAI ranked nonamers from the structural modeling.

However, although T cell receptors can be exquisitely sensitive to changes in peptide conformation, peptide immunogenicity (defined as having positive ELISPOT or ICS results or leading to tumor rejection) did not correlate with the magnitude of structural differences, expressed as root mean square deviations (RMSD) in Angstroms when all common atoms of each peptide pair were superimposed (FIG. 6B). Examining the modeling data more closely, however, revealed a correlation, albeit imperfect, with conformational stability. In 10 out of 14 cases, the mutant peptides were more rigid, sampling fewer conformations during the molecular dynamics phase of the modeling, expressed as the average root mean square fluctuations (RMSF) of all nine α carbons of each peptide (FIGS. 6C-D and FIG. 7). Of the 10 instances in which the mutant peptides were more rigid, eight of these had positive ICS or ELISPOT results. Of the four instances in which the WT peptides were more rigid, one did not yield any positive immunological outcomes. Altogether, greater structural stability was a predictor of immunogenicity in 9 out of 14, or 65% of the nonameric, high DAI ranking neo-epitopes.

In some instances, though, the differences in the fluctuations between the mutant and WT peptides were very small (for example, Ckap5, Dhx8.3, and Zfp236.2 have differences ≤±0.03 Å). This led us to question the fidelity of the average RMSF as a predictive tool. Examining the data for all peptides more closely, we observed a tendency for high structural instability in the peptide C-terminus, particularly in the WT peptides (FIG. 6C and FIG. 7). Previous studies have shown that weak binding peptides can detach and dissociate from MHC I proteins at the C-terminus, suggesting that in these cases the high structural instability reflects at least partial peptide dissociation. However, some of the mutant peptides also had high instability at the C-terminus. Most notably, all three mutant peptides which failed to elicit an immunological response had high C-terminal instability. To quantitate this, we calculated the average C-terminal RMSF for all mutant peptides. The C-terminal RMSF of the non-immunogenic peptides were all above this average value (FIG. 6E). Only three of the 14 immunogenic peptides had C-terminal RMSF values above the average (Stau1.4, Dhx8.3, and Tpst2.2). Thus, the presence or absence of C-terminal instability was a predictor of immunological outcome in 11 out of 14, or 79% of the nonameric high DAI ranking neo-epitopes. (We note that the HBV control peptide was relatively stable in the $K^d$ binding groove, with an average RMSD of 1.0 Å and an average C-terminal RMSF of 0.57 Å, as would be predicted from an immunogenic viral peptide).

Natural presentation of a neo-epitope. The tumor-protective immunogenicity of the epitope syMLQALCI (SEQ ID NO: 2) (wild type LDMLQALCI; SEQ ID NO: 138), the mutated Transportin 3 (Tnpo3)-derived epitope, the highest ranking (by DAI) epitope of Meth A (Table 6), was investigated in more detail. Tnpo3 is a nuclear import receptor and is not a driver protein for any tumor type reported thus far. The mutant Tnpo3 epitope was shown to elicit strictly tumor-specific CD8+ immune response, as seen by the ability of mutant Tnpo3-immunized mice to show strong tumor-specific CD8+, CD44+, IFNγ+ response to the mutant but not the WT peptide ex vivo or after stimulation in vitro (FIG. 8 A). A Tnpo3-specific immune response was also detectable ex vivo upon staining of cells with a Tnpo3-specific tetramer (FIG. 8B). Conversely, CD8+ CD44+ IFNγ+ cells isolated from mice immunized with Meth A cells, recognize mutant Tnpo3-pulsed cells but not cells pulsed with an irrelevant $K^d$-biding peptide Prpf31 ex vivo as well as after stimulation in vitro (FIG. 8C). Interesting, Meth A tumor-bearing mice (day 21 post-inoculation) harbor a low frequency of T cells recognizing two $K^d$-binding peptides (Tnpo3 and Nfkb1, measured by tetramer staining) in the tumor-draining LNs (FIG. 8D). These observations confirm that the mutant Tnpo3 peptide is naturally presented by Meth A cells and also that immune response to it is elicited upon immunization by whole tumor cells, as well as in tumor-bearing mice. Attempts to identify this mutant peptide by mass spectroscopic analysis of MHC I-eluted peptides from Meth A were un-successful, presumably because of the higher sensitivity of the T cell assays as compared to mass spectroscopy. The structural modeling predicts that the mutant Tnpo3 peptide is substantially more stable across the center of the peptide (FIG. 6).

Enhancement of tumor-protectivity of neo-epitopes by immune modulators. Combination of immunization with mutant neo-epitopes was tested using the Meth A neo-epitope Tnpo3. This neo-epitope is only modestly tumor protective in monotherapy thus allowing more dynamic range for testing of an enhanced effect by combination therapy. Combination of immunization with mutant Tnpo3 with antagonistic antibodies to CD25, which has been shown to target regulatory T cells, showed synergy; the anti-CD25 alone showed complete regression in all mice (p=0.008) and Tnpo3 alone too elicited significant protection (p=0.03). The combination showed more significant protection than either agent alone (p=0.016, FIG. 8E, left panel): although tumors eventually regressed in all mice in both groups, the kinetics of tumor regression was significantly steeper in the combination group. A similar result was obtained with anti-CTLA4 antibody, which releases T cells from checkpoint blockade. Each agent alone elicited statistically significant protection and the combination was significantly more effective than Tnpo3 alone (p=0.04) or anti-CTLA4 antibody alone (p=0.04) (FIG. 8E, right panel). Only a single tumor regressed in the anti-CTLA4 antibody group, and no tumors regressed in the Tnpo3 alone group (although the tumor growth was very significantly retarded); the combination group showed complete regression of two tumors, and a sustained trend towards regression in two additional tumors.

The use of the terms "a" and "an" and "the" and similar referents (especially in the context of the following claims) are to be construed to cover both the singular and the plural, unless otherwise indicated herein or clearly contradicted by context. The terms first, second etc. as used herein are not meant to denote any particular ordering, but simply for convenience to denote a plurality of, for example, layers. The terms "comprising", "having", "including", and "containing" are to be construed as open-ended terms (i.e., meaning "including, but not limited to") unless otherwise noted. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. A method of treating a cancer patient, the method comprising administering a pharmaceutical composition comprising a pharmaceutically acceptable carrier and
   (i) one or more immunologically protective neo-epitope peptides,
   (ii) one or more polypeptides containing immunologically protective neo-epitopes, or
   (iii) one or more polynucleotides encoding the one or more immunologically protective neo-epitopes,
   wherein
      a conformational stability of each of the immunologically protective neo-epitope bound to a major histocompatibility complex class I (MHC I) protein or a major histocompatibility complex class II (MHC II) protein, as determined by molecular modeling or by experiment, is higher than a corresponding wild-type epitope,
      each of the immunologically protective neo-epitopes have a measured IC50 for H-2Kd or human leukocyte antigen (HLA) of greater than 100 nM, and
      each of the immunologically protective neo-epitopes is specific to a tumor from a cancer patient and does not include epitopes from known cancer-causing pathways.

2. The method of claim 1, wherein the conformational stability is determined for the entire immunologically protective neo-epitopes.

3. The method of claim 1, wherein each of the immunologically protective neo-epitopes have a measured IC50 for H-$2K_d$ or human leukocyte antigen (HLA) of greater than 500 nM.

4. The method of claim 1, wherein the MHC protein is an MHC I protein and the immune response is a CD8+ response.

5. The method of claim 1, wherein the pharmaceutical composition comprises 1 to 100 immunologically protective neo-epitope peptides or polynucleotides.

6. The method of claim 1, further comprising an adjuvant, an immune-modulating agent, or a combination of the foregoing.

7. The method of claim 6, wherein the immune-modulating agent is a TLR ligand or an antibody.

8. The method of claim 1, wherein the cancer patient is suffering from a solid or liquid cancer.

9. The method of claim 1, further comprising treating the cancer patient with radiation therapy, chemotherapy, surgery, or a combination thereof.

10. The method of claim 1, wherein the conformation stability is measured by root mean squared fluctuations (RMSF).

11. The method of claim 1, wherein at least a portion of the α-carbons of each immunologically protective neo-epitope bound to the MHC I protein or the MHC II protein has a root mean squared fluctuations (RMSF) of less than 2 Å.

12. The method of claim 1, wherein at least a portion of the α-carbons of each immunologically protective neo-epitope bound to the MHC I protein or the MHC II protein has a root mean squared fluctuations (RMSF) of less than 1.5 Å.

13. The method of claim 1, wherein at least a portion of the α-carbons of each immunologically protective neo-epitope bound to the MHC I protein or the MHC II protein has a root mean squared fluctuations (RMSF) of less than 1.2 Å.

14. The method of claim 1, wherein at least a portion of the α-carbons of each immunologically protective neo-epitope bound to the MHC I protein or the MHC II protein has a root mean squared fluctuations (RMSF) of less than 0.9 Å.

15. The method of claim 1, wherein the conformational stability is determined for the C-terminal portion of the immunologically protective neo-epitopes.

16. The method of claim 1, wherein the conformational stability is determined for the central portion of the immunologically protective neo-epitopes.

17. The method of claim 1, wherein the conformational stability is determined for the N-terminal portion of the immunologically protective neo-epitopes.

18. The method of claim 1, wherein the MHC protein is an MHC II protein, and the immune response is a CD4+ response.

* * * * *